(12) United States Patent
Takemoto et al.

(10) Patent No.: US 8,158,329 B2
(45) Date of Patent: Apr. 17, 2012

(54) COMPOUND AND CHEMICALLY AMPLIFIED RESIST COMPOSITION CONTAINING THE SAME

(75) Inventors: Ichiki Takemoto, Kawanishi (JP); Nobuo Ando, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 335 days.

(21) Appl. No.: 12/631,061

(22) Filed: Dec. 4, 2009

(65) Prior Publication Data

US 2010/0151379 A1   Jun. 17, 2010

(30) Foreign Application Priority Data

Dec. 11, 2008   (JP) .................... 2008-315991

(51) Int. Cl.
  *G03F 7/039*   (2006.01)
  *G03F 7/004*   (2006.01)
  *G03C 1/73*   (2006.01)
  *C07D 311/00*   (2006.01)
  *C07D 311/02*   (2006.01)

(52) U.S. Cl. .............. 430/270.1; 430/326; 430/921; 430/925; 549/406; 549/407; 549/408; 549/409; 549/412; 549/385; 549/388; 549/345; 549/331

(58) Field of Classification Search .................. None
See application file for complete search history.

(56) References Cited

U.S. PATENT DOCUMENTS 5,420,331 A * 5/1995 Ueda et al. .................... 558/268
7,494,763 B2 2/2009 Takemoto et al.

FOREIGN PATENT DOCUMENTS

JP   2006-58739 A   3/2006

* cited by examiner

*Primary Examiner* — Sin J. Lee
(74) *Attorney, Agent, or Firm* — Oblon, Spivak, McClelland, Maier & Neustadt, L.L.P.

(57) ABSTRACT

The present invention provides a compound represented by the formula (I):

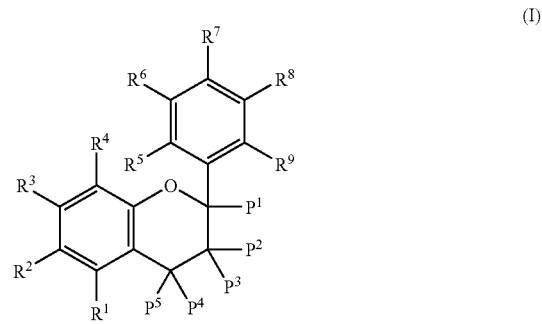

wherein $P^1$, $P^2$, $P^3$, $P^4$ and $P^5$ each independently represents a hydrogen atom etc., and at least one selected from the group consisting of $R^1$, $R^2$, $R^3$, $R^4$, $R^5$, $R^6$, $R^7$, $R^8$ and $R^9$ is the group represented by the formula (II):

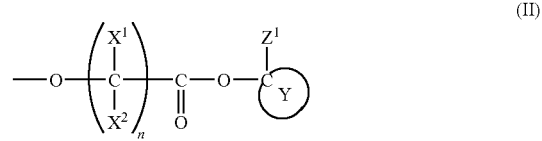

wherein $X^1$ and $X^2$ each independently represent a hydrogen atom etc., n represents an integer of 1 to 4, $Z^1$ represents a C1-C6 alkyl group etc., and ring Y represents an alicyclic hydrocarbon group,
and the others each independently represent a hydrogen atom, a C1-C6 alkyl group or a hydroxyl group, and a chemically amplified resist composition containing the same.

8 Claims, No Drawings

COMPOUND AND CHEMICALLY AMPLIFIED RESIST COMPOSITION CONTAINING THE SAME

This nonprovisional application claims priority under 35 U.S.C. §119(a) on Patent Application No. 2008-315991 filed in JAPAN on Dec. 11, 2008, the entire contents of which are hereby incorporated by reference.

FIELD OF THE INVENTION

The present invention relates to a novel compound and a chemically amplified resist composition containing the same.

BACKGROUND OF THE INVENTION

A chemically amplified resist composition is used for semiconductor microfabrication.

In semiconductor microfabrication, it is desirable to form patterns having high resolution, high sensitivity and good line-edge roughness, and it is expected for a chemically amplified resist composition to give such patterns.

JP 2006-58739 A discloses a chemically amplified resist composition containing a polyhydric phenol compound wherein at least one hydroxyl group bonded to a phenyl group is protected by a 1-ethoxyethyl group.

U.S. Pat. No. 7,494,763 B2 also discloses a chemically amplified resist composition containing a polyhydric phenol compound wherein at least one hydroxyl group bonded to a phenyl group is protected by a (2-ethyl-2-adamantyloxycarbonyl)methyl group.

SUMMARY OF THE INVENTION

An object of the present invention is to provide a novel compound capable of providing a chemically amplified resist composition giving patterns having good resolution and good line edge roughness.

The other object of the present invention is to provide a chemically amplified resist composition containing the same.

These and other objects of the present invention will be apparent from the following description.

The present invention relates to the followings:

<1> A compound represented by the formula (I):

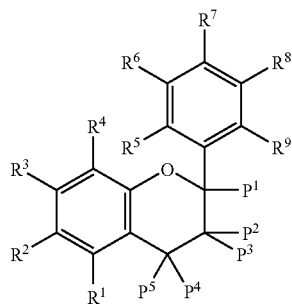

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and least one selected from the group consisting of $R^1$, $R^2$, $R^3$, $R^4$, $R^5$, $R^6$, $R^7$, $R^8$, and $R^9$ is the group represented by the formula (II):

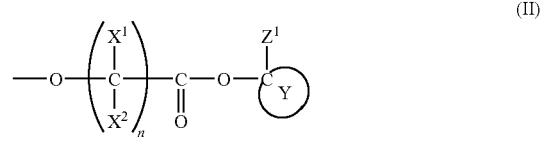

wherein $X^1$ and $X^2$ each independently represent a hydrogen atom or a C1-C4 alkyl group, n represents an integer of 1 to 4, $Z^1$ represents a C1-C6 alkyl group or a C3-C12 cycloalkyl group, and ring Y represents an alicyclic hydrocarbon group, and the others each independently represent a hydrogen atom, a C1-C6 alkyl group or a hydroxyl group;

<2> The compound according to <1>, wherein $X^1$ and $X^2$ are hydrogen atoms and n is 1;

<3> The compound according to claim 1 or <2>, wherein the molecular weight of the compound represented by the formula (I) is 500 to 5,000;

<4> A chemically amplified resist composition comprising a compound represented by the formula (I):

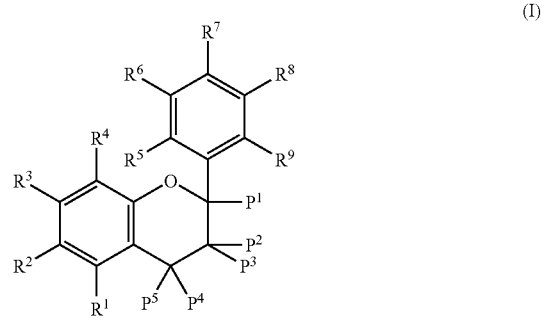

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and $R^1$, $R^2$, $R^3$, $R^4$, $R^5$, $R^6$, $R^7$, $R^8$ and $R^9$ each independently represent a hydrogen atom, a C1-C6 alkyl group, a hydroxyl group or a group represented by the formula (II):

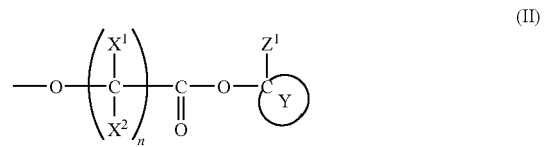

wherein $X^1$ and $X^2$ each independently represent a hydrogen atom or a C1-C4 alkyl group, n represents an integer of 1 to 4, $Z^1$ represents a C1-C6 alkyl group or a C3-C12 cycloalkyl group, and ring Y represents an alicyclic hydrocarbon group, and at least one selected from the group consisting of $R^1$, $R^2$, $R^3$, $R^4$, $R^5$, $R^6$, $R^7$, $R^8$ and $R^9$ is the group represented by the formula (II), and an acid generator;

<5> The chemically amplified resist composition according to <4>, wherein the composition contains at least two kinds of the compound represented by the formula (I);

<6> The chemically amplified resist composition according to <4> or <5>, wherein the composition further contains at least one compound selected from a compound represented by the formula (III):

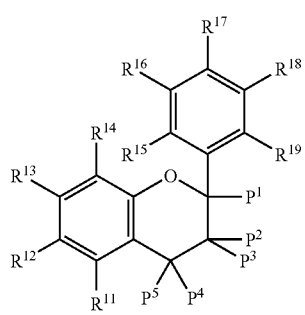

(III)

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and $R^{11}$, $R^{12}$, $R^{13}$, $R^{14}$, $R^{15}$, $R^{16}$, $R^{17}$, $R^{18}$ and $R^{19}$ each independently represent a hydrogen atom, a C1-C6 alkyl group or a hydroxyl group, and at least one selected from the group consisting of $R^{11}$, $R^{12}$, $R^{13}$, $R^{14}$, $R^{15}$, $R^{16}$, $R^{17}$, $R^{18}$ and $R^{19}$ is a hydroxyl group;

<7> The chemically amplified resist composition according to anyone of <4> to <6>, wherein the acid generator is a salt represented by the formula (V):

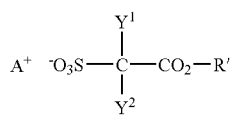

(V)

wherein $A^+$ represents an organic counter ion, $Y^1$ and $Y^2$ each independently represent a fluorine atom or a C1-C6 perfluoroalkyl group, R' represents a C1-C30 hydrocarbon group which may have one or more substituents selected from the group consisting of a C1-C6 alkoxy group, a C1-C4 perfluoroalkyl group, a C1-C6 hydroxyalkyl group, a hydroxyl group and a cyano group, and in which one or more —$CH_2$— may be replaced by —CO— or —O—;

<8> A process for production of a compound represented by the formula (I):

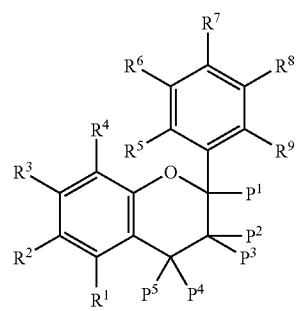

(I)

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and $R^1$, $R^2$, $R^3$, $R^4$, $R^5$, $R^6$, $R^7$, $R^8$ and $R^9$ each independently represent a hydrogen atom, a C1-C6 alkyl group, a hydroxyl group or a group represented by the formula (II):

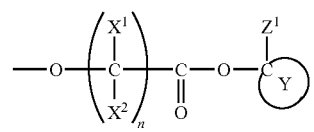

(II)

wherein $X^1$ and $X^2$ each independently represent a hydrogen atom or a C1-C4 alkyl group, n represents an integer of 1 to 4, $Z^1$ represents a C1-C6 alkyl group or a C3-C12 cycloalkyl group, and ring Y represents an alicyclic hydrocarbon group, and at least one selected from the group consisting of $R^1$, $R^2$, $R^3$, $R^4$, $R^5$, $R^6$, $R^7$, $R^8$ and $R^9$ is the group represented by the formula (II), which comprises reacting a compound represented by the formula (III):

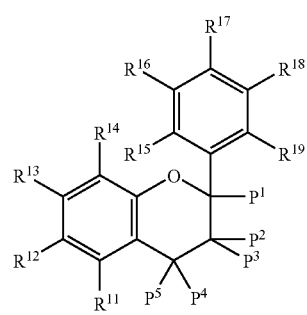

(III)

wherein $P^1$, $P^2$, $P^3$, $P^4$ and $P^5$ are the same as defined above, and at least one selected from the group consisting of $R^{11}$, $R^{12}$, $R^{13}$, $R^{14}$, $R^{15}$, $R^{16}$, $R^{17}$, $R^{18}$, $R^{19}$ is a hydroxyl group and the others each independently represent a hydrogen atom, a C1-C6 alkyl group or a hydroxyl group, with a compound represented by the formula (IV):

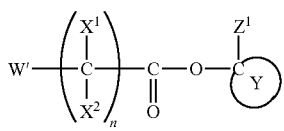

(IV)

wherein $X^1$, $X^2$, n, $Z^1$ and Y are the same as defined above, and W' represents a chlorine atom, a bromine atom, an iodine atom, a methanesulfonyloxy group or a p-toluenesulfonyloxy group.

DESCRIPTION OF PREFERRED EMBODIMENTS

First, the present compound represented by the formula (I) (hereinafter, simply referred to as the compound (I)) will be illustrated.

In the compound (I), $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group.

Examples of the C1-C4 alkyl group include a methyl group, an ethyl group, a propyl group, an isopropyl group, a butyl group, an isobutyl group, a sec-butyl group and a tert-butyl group, and a methyl group and an ethyl group are preferable. Examples of the C2-C4 alkenyl group include a vinyl group, a 1-propenyl group, a 2-propenyl group, an isopropenyl group, a 1-butenyl group, a 2-methyl-2-propenyl group and a 3-butenyl group, and a vinyl group and a 2-propenyl group are preferable. Examples of the C2-C4 alkynyl group include an ethynyl group, a 2-propynyl group and a 3-butynyl group. Examples of the C3-C8 cycloalkyl group include a cyclopropyl group, a cyclobutyl group, a cyclopentyl group, a cyclohexyl group, a cycloheptyl group and a cyclooctyl group, and a cyclopentyl group and a cyclohexyl group are preferable. Examples of the C6-C12 aryl group include a phenyl group, a tolyl group, a naphthyl group, a biphenyl group and an anthryl group, and a phenyl group and a tolyl group are preferable. Examples of the C7-C12 aralkyl group include a benzyl group, a phenylethyl group, a 6-phenylhexyl group, a 4,4-dimethyl-4-phenylbutyl group, a 1-naphthylmethyl group, a 2-naphthylmethyl group and a 3-(2-naphthyl)propyl group, and a benzyl group and a phenylethyl group are preferable.

$P^1$, $P^2$ and $P^3$ each independently preferably represent a hydrogen atom, a methyl group or an ethyl group. $P^3$ is more preferably a hydrogen atom.

$P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded. Examples of the C3-C12 divalent acyclic hydrocarbon group formed by bonding $P^1$ and $P^2$ or $P^4$ and $P^5$ include a trimethylene, tetramethylene, pentamethylene group. When $P^1$ and $P^2$ are bonded each other to form a C3-C12 divalent acyclic hydrocarbon group which forms a ring together with the carbon atom to which they are bonded, a trimethylene group and a tetramethylene group are preferable. When $P^4$ and $P^5$ are bonded each other to form a C3-C12 divalent acyclic hydrocarbon group which forms a ring together with the carbon atom to which they are bonded, a tetramethylene group and a pentamethylene group are preferable.

In the compound (I), at least one selected from the group consisting $R^1$, $R^2$, $R^3$, $R^4$, $R^5$, $R^6$, $R^7$, $R^8$ and $R^9$ is a group represented by the formula (II):

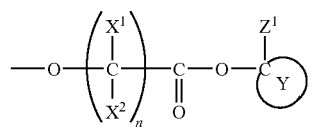

(II)

(hereinafter, simply referred to as the group (II)), and the others each independently represent a hydrogen atom, a C1-C6 alkyl group or a hydroxyl group.

In the group (II), $X^1$ and $X^2$ each independently represent a hydrogen atom or a C1-C4 alkyl group. Examples of the C1-C4 alkyl group include a methyl group, an ethyl group, a propyl group, an isopropyl group, a butyl group, an isobutyl group, a sec-butyl group and a tert-butyl group, and a methyl group and an ethyl group are preferable. $X^1$ and $X^2$ each independently preferably represent a hydrogen atom, a methyl group or an ethyl group. $X^1$ and $X^2$ are preferably same groups and more preferably hydrogen atoms. In the group (II), n represents an integer of 1 to 4, and n is preferably 1 or 2, and more preferably 1. The group (II) wherein $X^1$ and $X^2$ are hydrogen atoms and n is 1 is preferable.

$Z^1$ represents a C1-C6 alkyl group or a C3-C12 cycloalkyl group, and the C1-C6 alkyl group is preferable. Examples of the C1-C6 alkyl group include a methyl group, an ethyl group, a propyl group, an isopropyl group, a butyl group, an isobutyl group, a sec-butyl group, a tert-butyl group, a pentyl group, a 3-methylbutyl group and a hexyl group, and a methyl group, an ethyl group and an isopropyl group are preferable. Examples of the C3-C12 cycloalkyl group include a cyclopropyl group, a cyclobutyl group, a cyclopentyl group, a cyclohexyl group, a cycloheptyl group and a cyclooctyl group.

The ring Y represents an alicyclic hydrocarbon group. The alicyclic hydrocarbon group may have monocycle or bicycle or more, and the alicyclic hydrocarbon group having bicycle or more is preferable. The alicyclic hydrocarbon group preferably has 3 to 14 carbon atoms.

Examples of the alicyclic hydrocarbon group include the followings.

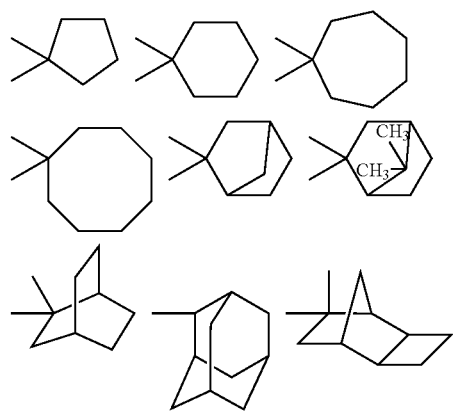

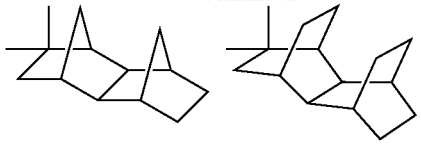

In the above formulae, one straight line with an open end shows a bond extended from the adjacent —O—, and the other straight line with an open end shows a bond extended from the adjacent group $Z^1$. Preferable examples thereof include the followings:

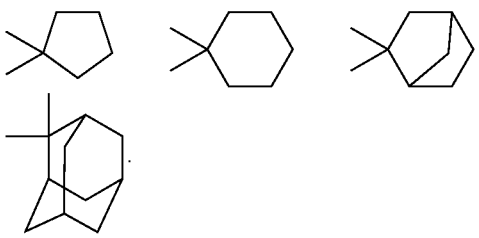

and more preferable examples thereof include the followings:

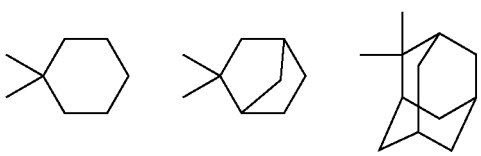

and especially preferable examples thereof include the followings:

In the above formulae, one straight line with an open end shows a bond extended from the adjacent —O—, and the other straight line with an open end shows a bond extended from the adjacent group $Z^1$.

Examples of the group represented by the following formula:

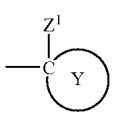

include the following groups.

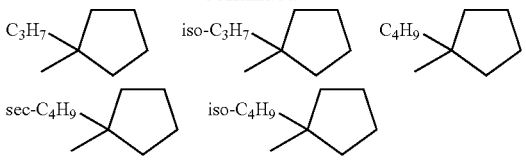
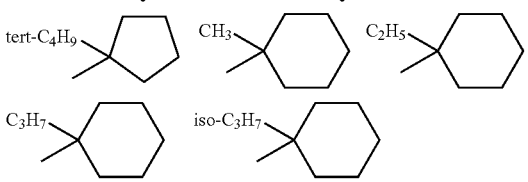
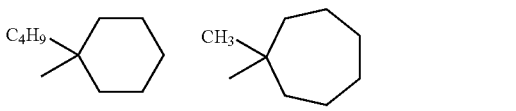
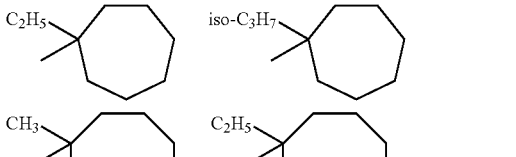
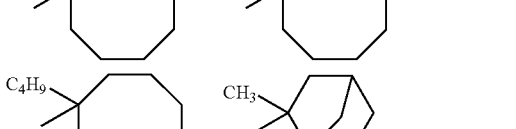
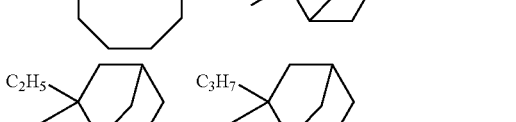
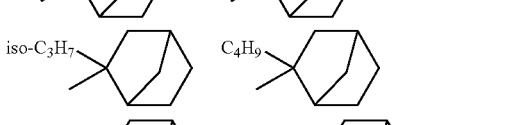
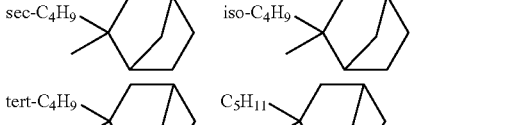
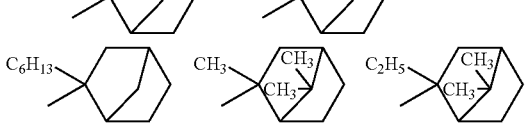
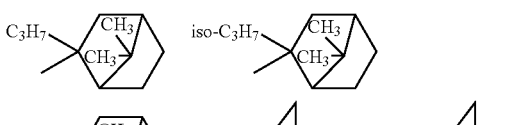
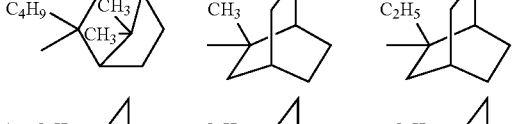
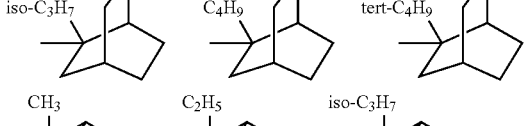
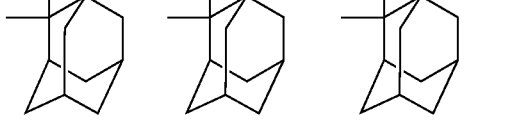

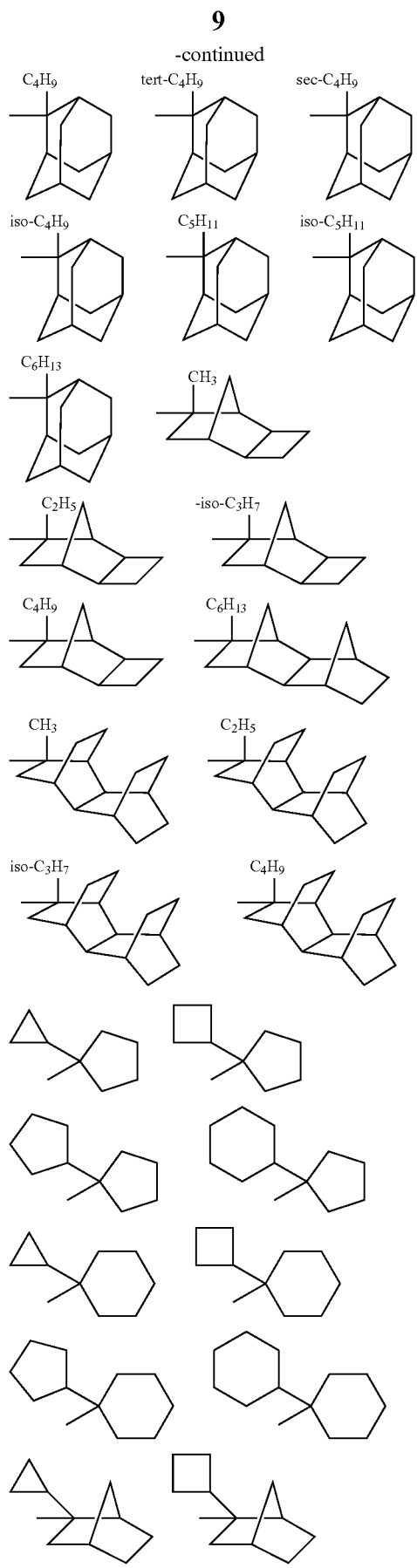
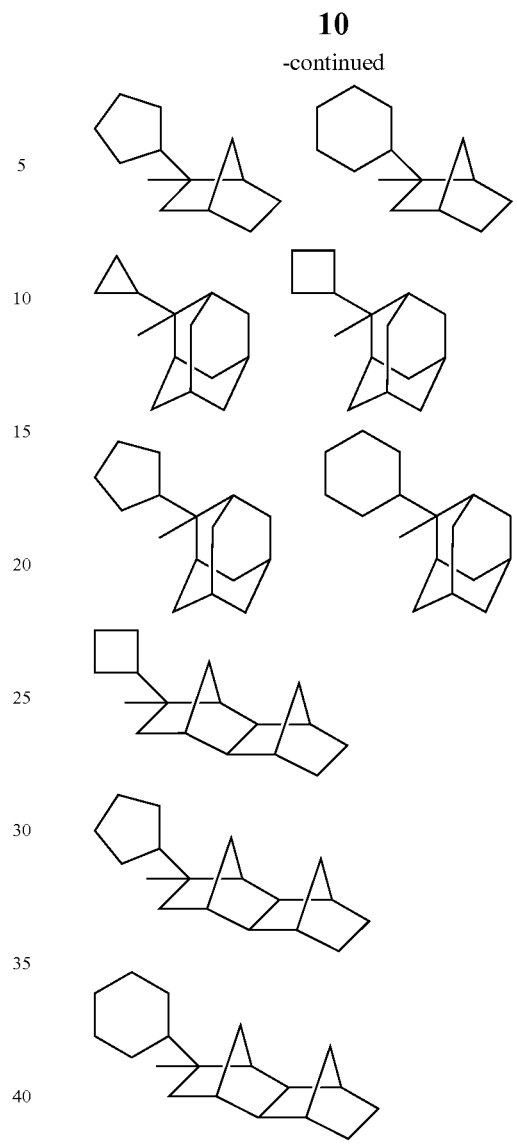
In the above formulae, a straight line with an open end shows a bond extended from the adjacent —O—.
Preferable examples thereof include the followings.
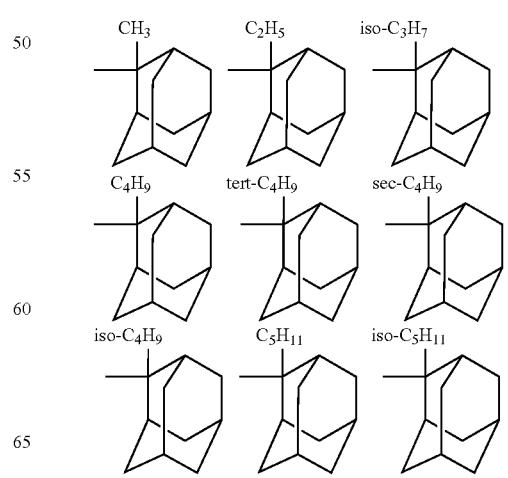

-continued

C₆H₁₃ [adamantane structure]

In the above formulae, a straight line with an open end shows a bond extended from the adjacent —O—.

Examples of the compound (I) include a compound wherein any one of $R^3$, $R^7$ and $R^9$ is the group (II) and the other two groups are hydroxyl groups (hereinafter, simply referred to as the compound (a1));

a compound wherein any two of $R^3$, $R^7$ and $R^9$ are the groups (II) and the other one group is a hydroxyl group (hereinafter, simply referred to as the compound (a2));

a compound wherein $R^3$, $R^7$ and $R^9$ are the groups (II) (hereinafter, simply referred to as the compound (a3));

a compound wherein any one of $R^3$, $R^7$ and $R^9$ is the group (II) and the other two groups are hydroxyl groups and $R^1$, $R^2$, $R^4$, $R^5$, $R^6$ and $R^8$ are hydrogen atoms (hereinafter, simply referred to as the compound (a4));

a compound wherein any two of $R^3$, $R^7$ and $R^9$ are the groups (II) and the other one group is a hydroxyl group and $R^1$, $R^2$, $R^3$, $R^4$, $R^5$, $R^6$ and $R^8$ are hydrogen atoms (hereinafter, simply referred to as the compound (a5));

a compound wherein $R^3$, $R^7$ and $R^9$ are the groups (II) and $R^1$, $R^2$, $R^4$, $R^5$, $R^6$ and $R^8$ are hydrogen atoms (hereinafter, simply referred to as the compound (a6));

a compound wherein any one of $R^3$, $R^7$ and $R^9$ is the group (II) and the other two groups are hydroxyl groups and $P^1$, $P^4$ and $P^5$ each independently represents a C1-C4 alkyl group and $P^2$ and $P^3$ are hydrogen atoms (hereinafter, simply referred to as the compound (a7));

a compound wherein any two of $R^3$, $R^7$ and $R^9$ are the groups (II) and the other one group is a hydroxyl group and $P^1$, $P^4$ and $P^5$ each independently represents a C1-C4 alkyl group and $P^2$ and $P^3$ are hydrogen atoms (hereinafter, simply referred to as the compound (a8));

a compound wherein $R^3$, $R^7$ and $R^9$ are the groups (II) and $P^1$, $P^4$ and $P^5$ each independently represents a C1-C4 alkyl group and $P^2$ and $P^3$ are hydrogen atoms (hereinafter, simply referred to as the compound (a9));

a compound wherein any one of $R^3$, $R^7$ and $R^9$ is the group (II) and the other two groups are hydroxyl groups and $R^1$, $R^2$, $R^3$, $R^4$, $R^5$, $R^6$ and $R^8$ are hydrogen atoms and $P^1$, $P^4$ and $P^5$ each independently represents a C1-C4 alkyl group and $P^2$ and $P^3$ are hydrogen atoms (hereinafter, simply referred to as the compound (a10));

a compound wherein any two of $R^3$, $R^7$ and $R^9$ are the groups (II) and the other one group is a hydroxyl group and $R^1$, $R^2$, $R^3$, $R^4$, $R^5$, $R^6$ and $R^8$ are hydrogen atoms and $P^1$, $P^4$ and $P^5$ each independently represents a C1-C4 alkyl group and $P^2$ and $P^3$ are hydrogen atoms (hereinafter, simply referred to as the compound (a11));

a compound wherein $R^3$, $R^7$ and $R^9$ are the groups (II) and $R^1$, $R^2$, $R^4$, $R^5$, $R^6$ and $R^8$ are hydrogen atoms and $P^1$, $P^4$ and $P^5$ each independently represents a C1-C4 alkyl group and $P^2$ and $P^3$ are hydrogen atoms (hereinafter, simply referred to as the compound (a12));

a compound wherein any one of $R^3$, $R^7$ and $R^9$ is the group (II) and the other two groups are hydroxyl groups and $P^1$, $P^4$ and $P^5$ are methyl groups and $P^2$ and $P^3$ are hydrogen atoms (hereinafter, simply referred to as the compound (a13));

a compound wherein any two of $R^3$, $R^7$ and $R^9$ are the groups (II) and the other one group is a hydroxyl group and $P^1$, $P^4$ and $P^5$ are methyl groups and $P^2$ and $P^3$ are hydrogen atoms (hereinafter, simply referred to as the compound (a14));

a compound wherein $R^3$, $R^7$ and $R^9$ are the groups (II) and $P^1$, $P^4$ and $P^5$ are methyl groups and $P^2$ and $P^3$ are hydrogen atoms (hereinafter, simply referred to as the compound (a15));

a compound wherein any one of $R^3$, $R^7$ and $R^9$ is the group (II) and the other two groups are hydroxyl groups and $R^1$, $R^2$, $R^4$, $R^5$, $R^6$ and $R^8$ are hydrogen atoms and $P^1$, $P^4$ and $P^5$ are methyl groups and $P^2$ and $P^3$ are hydrogen atoms (hereinafter, simply referred to as the compound (a16));

a compound wherein any two of $R^3$, $R^7$ and $R^9$ are the groups (II) and the other one group is a hydroxyl group and $R^1$, $R^2$, $R^4$, $R^5$, $R^6$ and $R^8$ are hydrogen atoms and $P^1$, $P^4$ and $P^5$ are methyl groups and $P^2$ and $P^3$ are hydrogen atoms (hereinafter, simply referred to as the compound (a17));

a compound wherein $R^3$, $R^7$ and $R^9$ are the groups (II) and $R^1$, $R^2$, $R^4$, $R^5$, $R^6$ and $R^8$ are hydrogen atoms and $P^1$, $P^4$ and $P^5$ are methyl groups and $P^2$ and $P^3$ are hydrogen atoms (hereinafter, simply referred to as the compound (a18));

a compound wherein any one of $R^3$, $R^4$, $R^7$, $R^8$ and $R^9$ is the group (II) and the other four groups are hydroxyl groups (hereinafter, simply referred to as the compound (a19));

a compound wherein any two of $R^3$, $R^4$, $R^7$, $R^8$ and $R^9$ are the groups (II) and the other three groups are hydroxyl groups (hereinafter, simply referred to as the compound (a20));

a compound wherein any three of $R^3$, $R^4$, $R^7$, $R^8$ and $R^9$ are the groups (II) and the other two groups are hydroxyl groups (hereinafter, simply referred to as the compound (a21));

a compound wherein any four of $R^3$, $R^4$, $R^7$, $R^8$ and $R^9$ are the groups (II) and the other one group is a hydroxyl group (hereinafter, simply referred to as the compound (a22));

a compound wherein $R^3$, $R^4$, $R^7$, $R^8$ and $R^9$ are the groups (II) (hereinafter, simply referred to as the compound (a23));

a compound wherein any one of $R^3$, $R^4$, $R^7$, $R^8$ and $R^9$ is the group (II) and the other four groups are hydroxyl groups and $R^1$, $R^2$, $R^5$ and $R^6$ and $R^8$ are hydrogen atoms (hereinafter, simply referred to as the compound (a24));

a compound wherein any two of $R^3$, $R^4$, $R^7$, $R^8$ and $R^9$ are the groups (II) and the other three groups are hydroxyl groups and $R^1$, $R^2$, $R^5$ and $R^6$ are hydrogen atoms (hereinafter, simply referred to as the compound (a25));

a compound wherein any three of $R^3$, $R^4$, $R^7$, $R^8$ and $R^9$ are the groups (II) and the other two groups are hydroxyl groups and $R^1$, $R^2$, $R^5$ and $R^6$ are hydrogen atoms (hereinafter, simply referred to as the compound (a26));

a compound wherein any four of $R^3$, $R^4$, $R^7$, $R^8$ and $R^9$ are the groups (II) and the other one group is a hydroxyl groups and $R^1$, $R^2$, $R^5$ and $R^6$ are hydrogen atoms (hereinafter, simply referred to as the compound (a27));

a compound wherein $R^3$, $R^4$, $R^7$, $R^8$ and $R^9$ are the groups (II) and $R^1$, $R^2$, $R^5$ and $R^6$ are hydrogen atoms (hereinafter, simply referred to as the compound (a28));

a compound wherein any one of $R^3$, $R^4$, $R^7$, $R^8$ and $R^9$ is the group (II) and the other four groups are hydroxyl groups and $P^1$, $P^4$ and $P^5$ each independently represents a C1-C4 alkyl group and $P^2$ and $P^3$ are hydrogen atoms (hereinafter, simply referred to as the compound (a29));

a compound wherein any two of $R^3$, $R^4$, $R^7$, $R^8$ and $R^9$ are the groups (II) and the other three groups are hydroxyl groups and $P^1$, $P^4$ and $P^5$ each independently represents a C1-C4 alkyl group and $P^2$ and $P^3$ are hydrogen atoms (hereinafter, simply referred to as the compound (a30));

a compound wherein any three of $R^3$, $R^4$, $R^7$, $R^8$ and $R^9$ are the groups (II) and the other two groups are hydroxyl groups and $P^1$, $P^4$ and $P^5$ each independently represents a C1-C4 alkyl group and $P^2$ and $P^3$ are hydrogen atoms (hereinafter, simply referred to as the compound (a31));

a compound wherein any four of $R^3$, $R^4$, $R^7$, $R^8$ and $R^9$ are the groups (II) and the other one group is a hydroxyl groups and $P^1$, $P^4$ and $P^5$ each independently represents a C1-C4 alkyl group and $P^2$ and $P^3$ are hydrogen atoms (hereinafter, simply referred to as the compound (a32));

a compound wherein $R^3$, $R^4$, $R^7$, $R^8$ and $R^9$ are the groups (II) and $P^1$, $P^4$ and $P^5$ each independently represents a C1-C4 alkyl group and $P^2$ and $P^3$ are hydrogen atoms (hereinafter, simply referred to as the compound (a33));

a compound wherein any one of $R^3$, $R^4$, $R^7$, $R^8$ and $R^9$ is the group (II) and the other four groups are hydroxyl groups and $P^1$, $P^4$ and $P^5$ are methyl groups and $P^2$ and $P^3$ are hydrogen atoms (hereinafter, simply referred to as the compound (a34));

a compound wherein any two of $R^3$, $R^4$, $R^7$, $R^8$ and $R^9$ are the groups (II) and the other three groups hydroxyl groups and $P^1$, $P^4$ and $P^5$ are methyl groups and $P^2$ and $P^3$ are hydrogen atoms (hereinafter, simply referred to as the compound (a35));

a compound wherein any three of $R^3$, $R^4$, $R^7$, $R^8$ and $R^9$ are the groups (II) and the other two groups hydroxyl groups and $P^1$, $P^4$ and $P^5$ are methyl groups and $P^2$ and $P^3$ are hydrogen atoms (hereinafter, simply referred to as the compound (a36));

a compound wherein any four of $R^3$, $R^4$, $R^7$, $R^8$ and $R^9$ are the groups (II) and the other one group is a hydroxyl groups and $P^1$, $P^4$ and $P^5$ are methyl groups and $P^2$ and $P^3$ are hydrogen atoms (hereinafter, simply referred to as the compound (a37));

a compound wherein $R^3$, $R^4$, $R^7$, $R^8$ and $R^9$ are the groups (II) and $P^1$, $P^4$ and $P^5$ are methyl groups and $P^2$ and $P^3$ are hydrogen atoms (hereinafter, simply referred to as the compound (a38));

a compound wherein any one of $R^3$, $R^4$, $R^7$, $R^8$ and $R^9$ is the group (II) and the other four groups are hydroxyl groups and $R^1$, $R^2$, $R^5$ and $R^6$ are hydrogen atoms and $P^1$, $P^4$ and $P^5$ are methyl groups and $P^2$ and $P^3$ are hydrogen atoms (hereinafter, simply referred to as the compound (a39));

a compound wherein any two of $R^3$, $R^4$, $R^7$, $R^8$ and $R^9$ are the groups (II) and the other three groups hydroxyl groups and $R^1$, $R^2$, $R^5$ and $R^6$ are hydrogen atoms and $P^1$, $P^4$ and $P^5$ are methyl groups and $P^2$ and $P^3$ are hydrogen atoms (hereinafter, simply referred to as the compound (a40));

a compound wherein any three of $R^3$, $R^4$, $R^7$, $R^8$ and $R^9$ are the groups (II) and the other two groups hydroxyl groups and $R^1$, $R^2$, $R^5$ and $R^6$ are hydrogen atoms and $P^1$, $P^4$ and $P^5$ are methyl groups and $P^2$ and $P^3$ are hydrogen atoms (hereinafter, simply referred to as the compound (a41));

a compound wherein any four of $R^3$, $R^4$, $R^7$, $R^8$ and $R^9$ are the groups (II) and the other one group is a hydroxyl groups and $R^1$, $R^2$, $R^5$ and $R^6$ are hydrogen atoms and $P^1$, $P^4$ and $P^5$ are methyl groups and $P^2$ and $P^3$ are hydrogen atoms (hereinafter, simply referred to as the compound (a42));

a compound wherein $R^3$, $R^4$, $R^7$, $R^8$ and $R^9$ are the groups (II) and $R^1$, $R^2$, $R^5$ and $R^6$ are hydrogen atoms and $P^1$, $P^4$ and $P^5$ are methyl groups and $P^2$ and $P^3$ are hydrogen atoms (hereinafter, simply referred to as the compound (a43));

a compound wherein any one of $R^3$, $R^7$ and $R^9$ is the group (II) and the other two groups are hydroxyl groups and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a44));

a compound wherein any two of $R^3$, $R^7$ and $R^9$ are the groups (II) and the other one group is a hydroxyl group and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a45));

a compound wherein $R^3$, $R^7$ and $R^9$ are the groups (II) and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a46));

a compound wherein any one of $R^3$, $R^7$ and $R^9$ is the group (II) and the other two groups are hydroxyl groups and $R^4$ and $R^8$ are methyl groups and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a47));

a compound wherein any two of $R^3$, $R^7$ and $R^9$ are the groups (II) and the other one group is a hydroxyl group and $R^4$ and $R^8$ are methyl groups and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a48));

a compound wherein $R^3$, $R^7$ and $R^9$ are the groups (II) and $R^4$ and $R^8$ are methyl groups and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a49));

a compound wherein any one of $R^3$, $R^7$ and $R^9$ is the group (II) and the other two groups are hydroxyl groups and $R^4$ and $R^8$ are methyl groups and $R^1$, $R^2$, $R^5$ and $R^6$ are hydrogen atoms and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a50));

a compound wherein any two of $R^3$, $R^7$ and $R^9$ are the groups (II) and the other one group is a hydroxyl group and $R^4$ and $R^8$ are methyl groups and $R^1$, $R^2$, $R^5$ and $R^6$ are hydrogen atoms and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a51)); and a compound wherein $R^3$, $R^7$ and $R^9$ are the groups (II) and $R^4$ and $R^8$ are methyl groups and $R^1$, $R^2$, $R^5$ and $R^6$ are hydrogen atoms and $P^1$ and $P^2$ are bonded each other to form a tetramethylene group which forms a ring together with the carbon atom to which they are bonded and $P^4$ and $P^5$ are bonded each other to form a pentamethylene group which forms a ring together with the carbon atom to which they are bonded and $P^3$ is a hydrogen atom (hereinafter, simply referred to as the compound (a52)).

Preferable examples of the compound (I) include the compound (a1) and the compound (a2), and more preferable examples of the compound (I) include the compound (a4), the compound (a5), the compound (a7), the compound (a8), the compound (a10), the compound (a11), the compound (a13), the compound (a14), the compound (a16), the compound (a17), the compound (a44), the compound (a45), the compound (a47), the compound (a48), the compound (a50) and the compound (a51).

The molecular weight of the compound (I) is usually 500 to 5,000, preferably 550 to 4,500 and more preferably 600 to 4,000.

The compound (I) can be produced by a reaction of a compound represented by the formula (III):

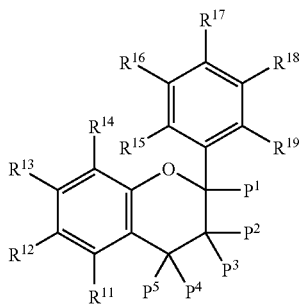

(III)

wherein $P^1$, $P^2$, $P^3$, $P^4$ and $P^5$ are the same as defined above, and at least one selected from the group consisting of $R^{11}$, $R^{12}$, $R^{13}$, $R^{14}$, $R^{15}$, $R^{16}$, $R^{17}$, $R^{18}$ and $R^{19}$ is a hydroxyl group and the others each independently represent a hydrogen atom, a C1-C6 alkyl group or a hydroxyl group (hereinafter, simply referred to as the compound (III)), with a compound represented by the formula (IV):

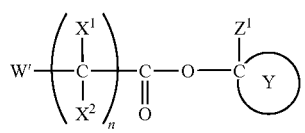

(IV)

wherein $X^1$, $X^2$, n, $Z^1$ and Y are the same as defined above, and W' represents a chlorine atom, a bromine atom, an iodine atom, a methanesulfonyloxy group or a p-toluenesulfonyloxy group (hereinafter, simply referred to as the compound (IV)).

The compound (III) can be produced according to the method described in JP 05-32654 A, JP 09-31044 A or Mendeleev Communications, 194-197 (2003). The compound (IV) can be produced according to the method described in JP 2004-26798 A.

Examples of the compound (III) include the followings.

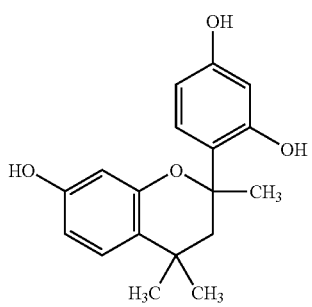

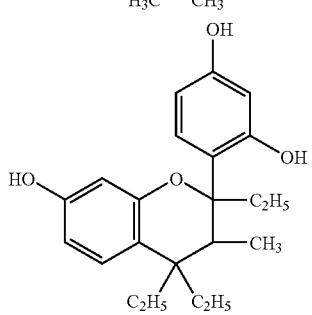

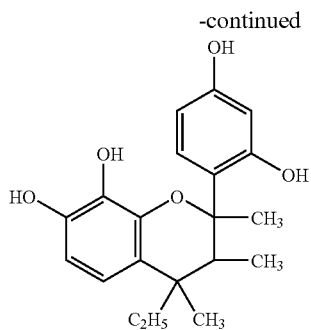

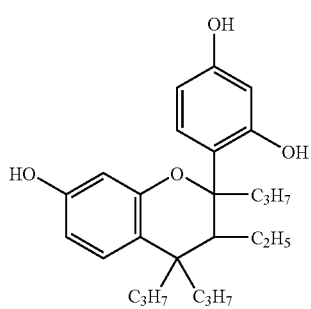

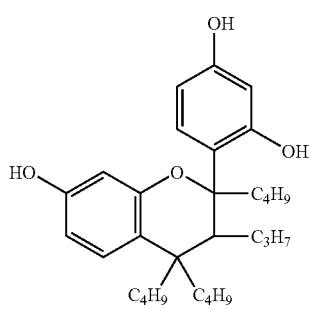

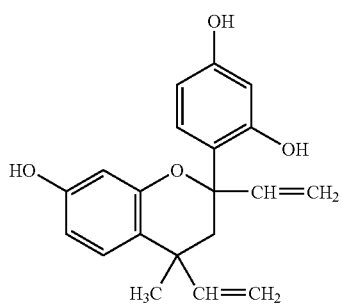

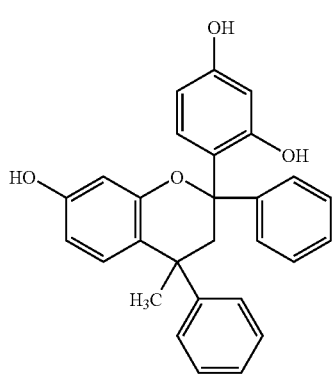

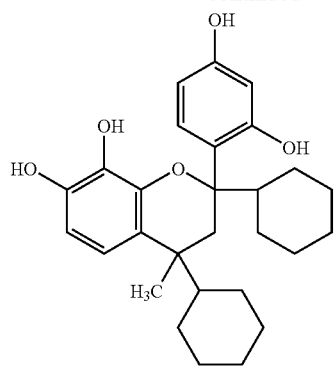
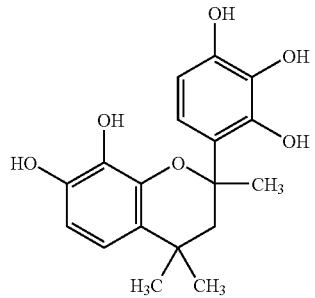
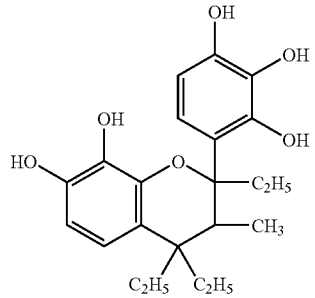
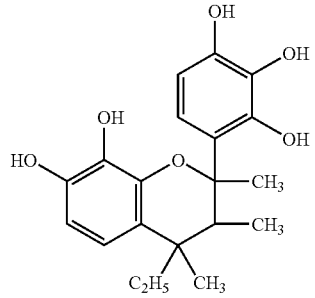
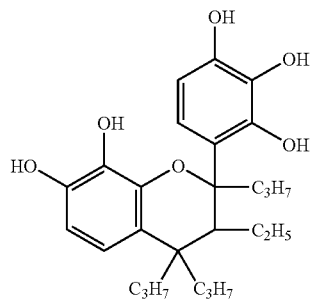
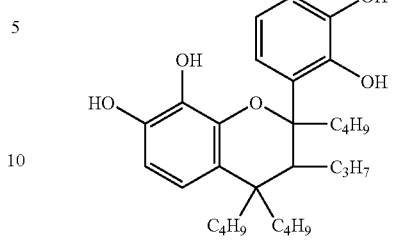
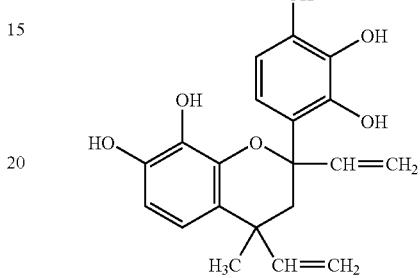
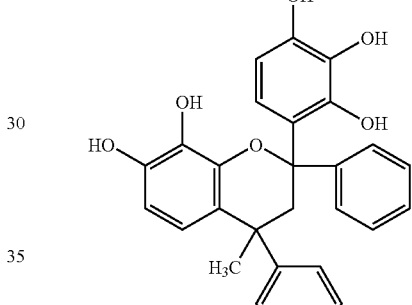
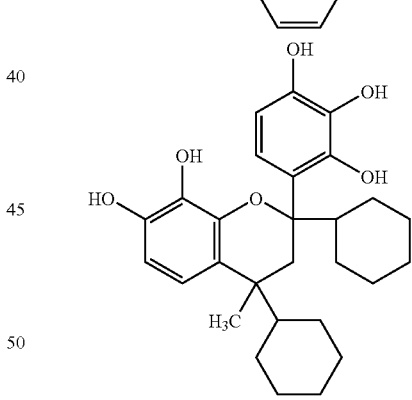
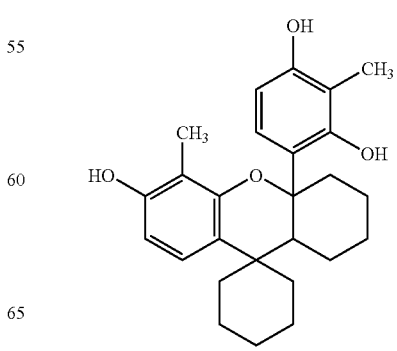

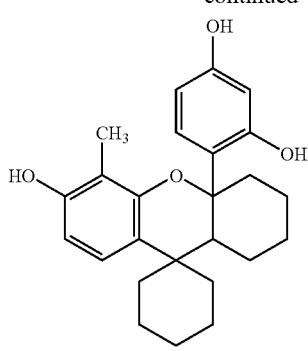

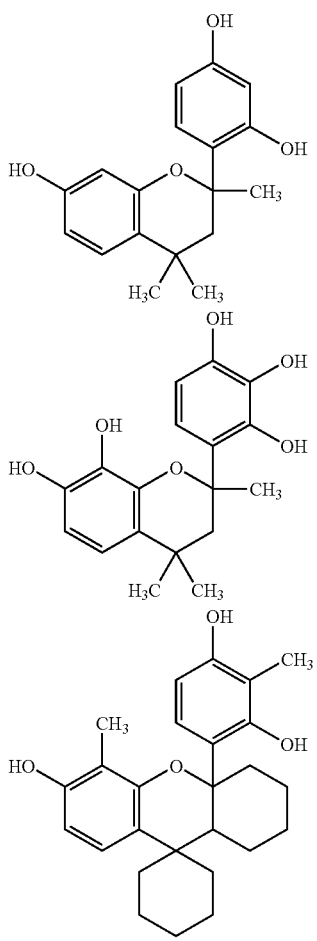

The following compounds are preferable as the compound (III).

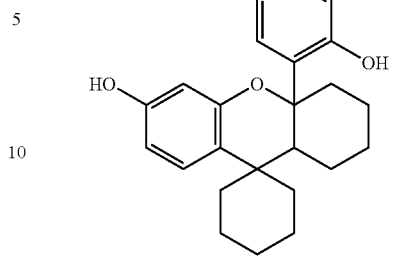

As the compound (IV), commercially available one may be used and one produced by a known method may be used.

The reaction of the compound (III) and the compound (IV) is usually conducted in an inert solvent such as toluene, tetrahydrofuran, N,N-dimethylformamide and dimethylsulfoxide. The reaction temperature is usually −30 to 200° C., preferably 0 to 150° C.

The used amount of the compound (IV) is usually 1 to 9 moles and preferably 1 to 4 moles per 1 mole of the compound (III).

The reaction is preferably carried out in the presence of a base. Examples of the base include an organic base such as triethylamine, pyridine, sodium methoxide, sodium ethoxide and potassium tert-butoxide; an inorganic base such as sodium hydride, potassium carbonate and sodium hydroxide. These bases may be used alone and a mixture thereof may be used. The used amount of the base is usually 1 to 9 moles and preferably 1 to 4 moles per 1 mole of the compound (III).

The reaction may be conducted in the presence of a phase transfer catalyst such as tetrabutylammonium bromide. The reaction may also be conducted in the presence of an iodide compound such as potassium iodide.

After completion of the reaction, the compound (I) can be isolated, for example, by conducting extraction of the reaction mixture and then concentrating the organic layer obtained. The compound (I) isolated may be further purified by a conventional purification means such as column chromatography.

Next, the present chemically amplified resist composition will be illustrated.

The compound (I) itself is insoluble or poorly soluble in an aqueous alkali solution and becomes soluble in an aqueous alkali solution by the action of an acid.

The present chemically amplified resist composition contains the compound (I) and an acid generator.

The acid generator generates an acid with the action of radiation, and the acid generated by irradiation to the present resist composition catalytically acts against the compound (I), cleaves the group capable of being cleaved by the acid, and the compound (I) becomes soluble in an alkali aqueous solution.

The present resist composition preferably contains at least two kinds of the compound (I).

The present resist composition preferably contains at least one selected from the group consisting of the compound (a1), the compound (a2) and the compound (a3), and more preferably contains at least two selected from the group consisting of the compound (a1), the compound (a2) and the compound (a3).

Preferable examples of the resist composition include
a composition containing at least two selected from the group consisting of the compound (a4), the compound (a5) and the compound (a6);
a composition containing at least two selected from the group consisting of the compound (a7), the compound (a8) and the compound (a9);
a composition containing at least two selected from the group consisting of the compound (a10), the compound (a11) and the compound (a12);
a composition containing at least two selected from the group consisting of the compound (a13), the compound (a14) and the compound (a15);
a composition containing at least two selected from the group consisting of the compound (a16), the compound (a17) and the compound (a18);
a composition containing at least two selected from the group consisting of the compound (a44), the compound (a45) and the compound (a46);
a composition containing at least two selected from the group consisting of the compound (a47), the compound (a48) and the compound (a49); and
a composition containing at least two selected from the group consisting of the compound (a50), the compound (a51) and the compound (a52).

The acid generator in the resist composition of the present invention can be selected from various compounds generating an acid by irradiation with radiation on the acid generator itself or a resist composition containing the acid generator. Examples of the acid generator include an onium salt, a halogenated alkyltriazine compound, a disulfone compound, a diazomethane compound having a sulfonyl group, a sulfonate compound and an imide compound having a sulfonyloxy group. Examples of the acid generator include an acid generator described in JP 2003-5374 A. The onium salt is preferable.

Examples of the preferable acid generator include a salt represented by the formula (V):

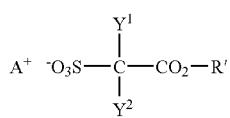

wherein $A^+$ represents an organic counter ion, $Y^1$ and $Y^2$ each independently represent a fluorine atom or a C1-C6 perfluoroalkyl group, R' represents a C1-C30 hydrocarbon group which may have one or more substituents selected from the group consisting of a C1-C6 alkoxy group, a C1-C4 perfluoroalkyl group, a C1-C6 hydroxyalkyl group, a hydroxyl group and a cyano group, and in which one or more —CH$_2$— may be replace by —CO— or —O— (hereinafter, simply referred to as Salt (V)).

Examples of the C1-C6 perfluoroalkyl group represented by $Y^1$ and $Y^2$ include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Y^1$ and $Y^2$ each independently is preferably a fluorine atom or a trifluoromethyl group, and $Y^1$ and $Y^2$ are more preferably fluorine atoms.

Examples of the C1-C30 hydrocarbon group include a linear or branched chain C1-C30 hydrocarbon group such as a methyl group, an ethyl group, a propyl group, an isopropyl group, a butyl group, an isobutyl group, a sec-butyl group, a tert-butyl group, a pentyl group and a hexyl group, and a C3-C30 monocyclic or polycyclic hydrocarbon group such as a hydrocarbon group having a cyclobutane ring, a hydrocarbon group having a cyclopentane ring, a hydrocarbon group having a cyclohexane ring, a hydrocarbon group having a cyclooctane ring, a hydrocarbon group having an adamantane ring, a hydrocarbon group having a benzene ring and a hydrocarbon group having a norbornane ring. The C3-C30 monocyclic or polycyclic hydrocarbon group may have an alicyclic structure or structures and may have an aromatic group or groups. The C3-C30 monocyclic or polycyclic hydrocarbon group may have a carbon-carbon double bond or bonds.

The C1-C30 hydrocarbon group may have one or more substituents selected from the group consisting of a C1-C6 alkoxy group, a C1-C4 perfluoroalkyl group, a C1-C6 hydroxyalkyl group, a hydroxyl group and a cyano group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the C1-C4 perfluoroalkyl group include a trifluoromethyl group, a pentafluoroethyl group, a heptafluoropropyl group and a nonafluorobutyl group. Examples of the C1-C6 hydroxyalkyl group include a hydroxymethyl group, a 2-hydroxyethyl group, a 3-hydroxypropyl group, a 4-hydroxybutyl group and a 6-hydroxyhexyl group.

Specific examples of the anion part of Salt (V) include the followings.

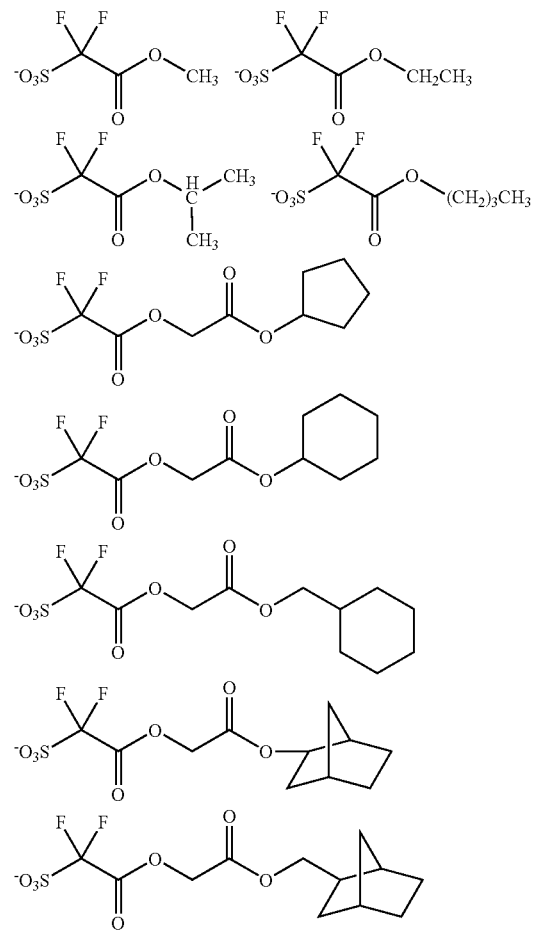

-continued
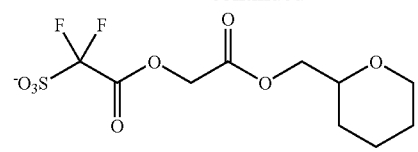
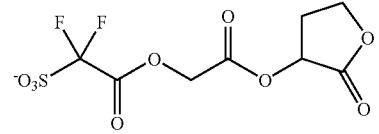
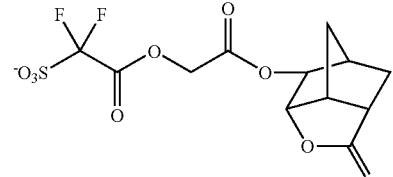
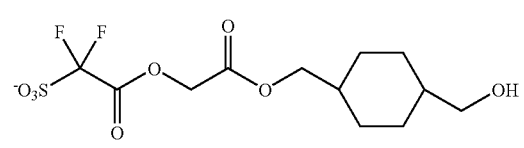
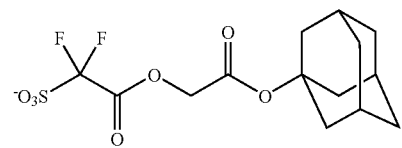
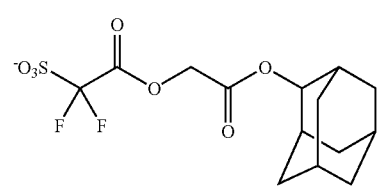
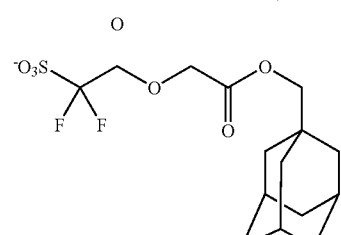
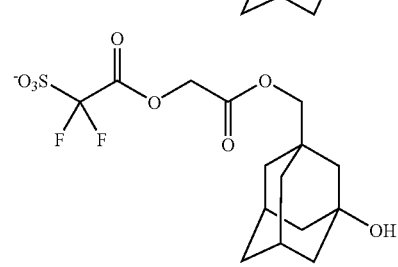
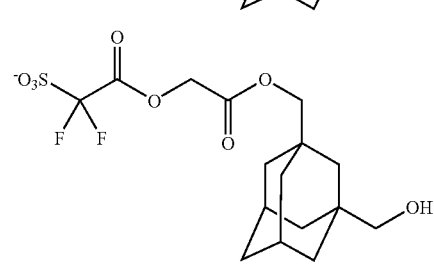
-continued
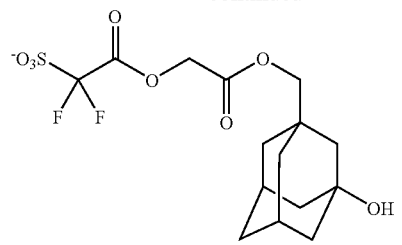
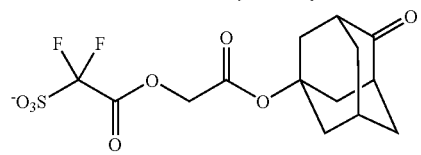
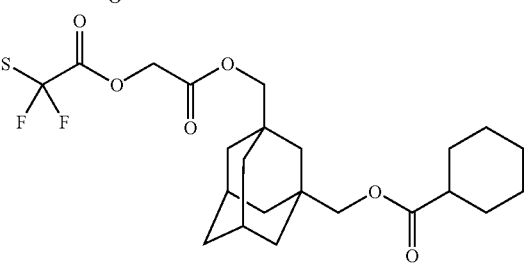
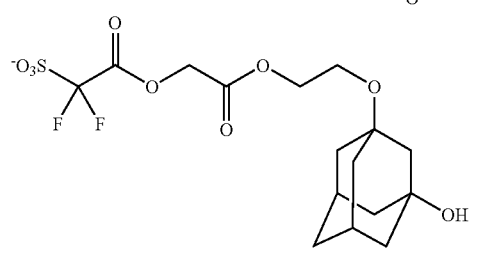
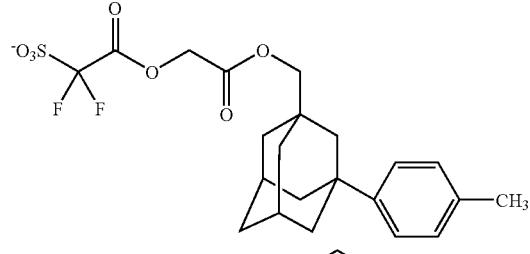
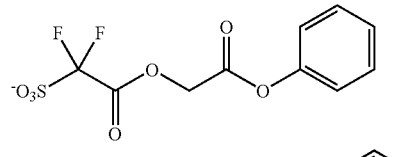
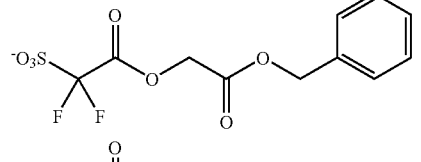
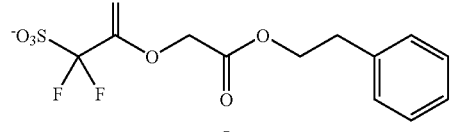
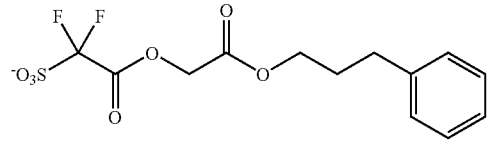

25
-continued
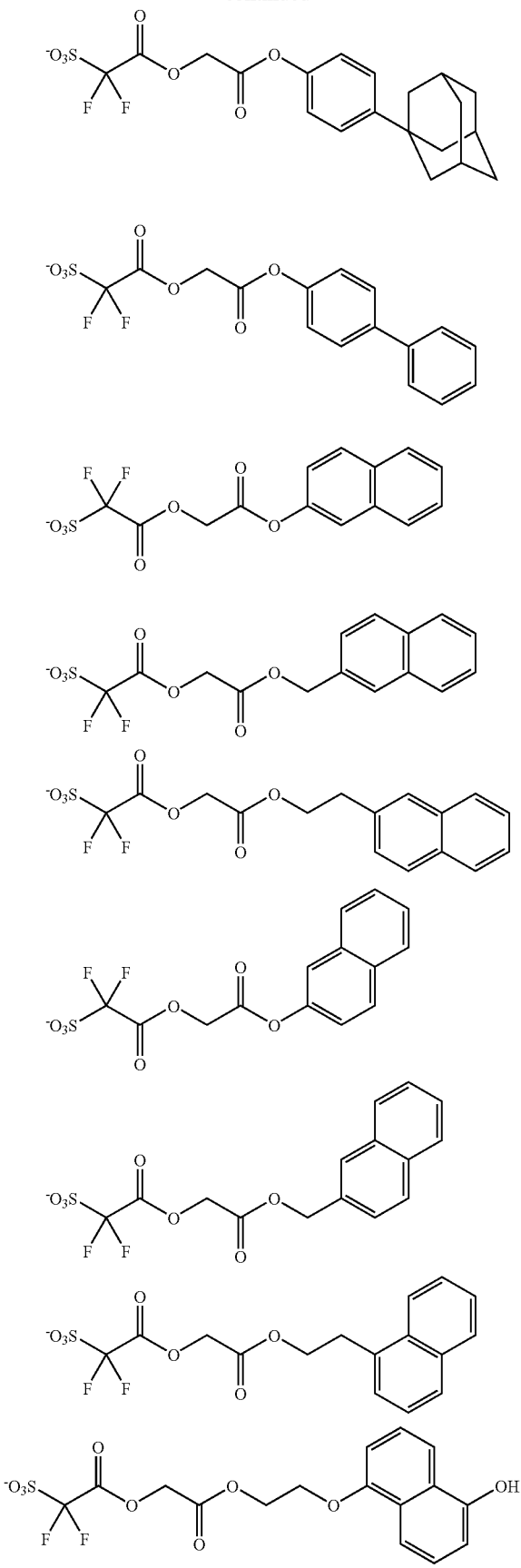
26
-continued
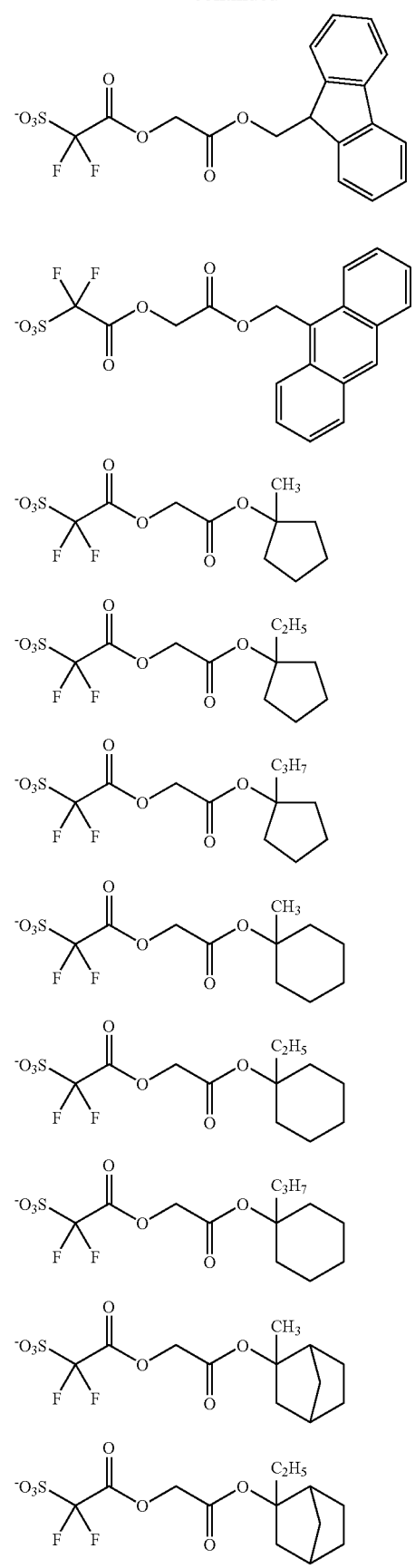

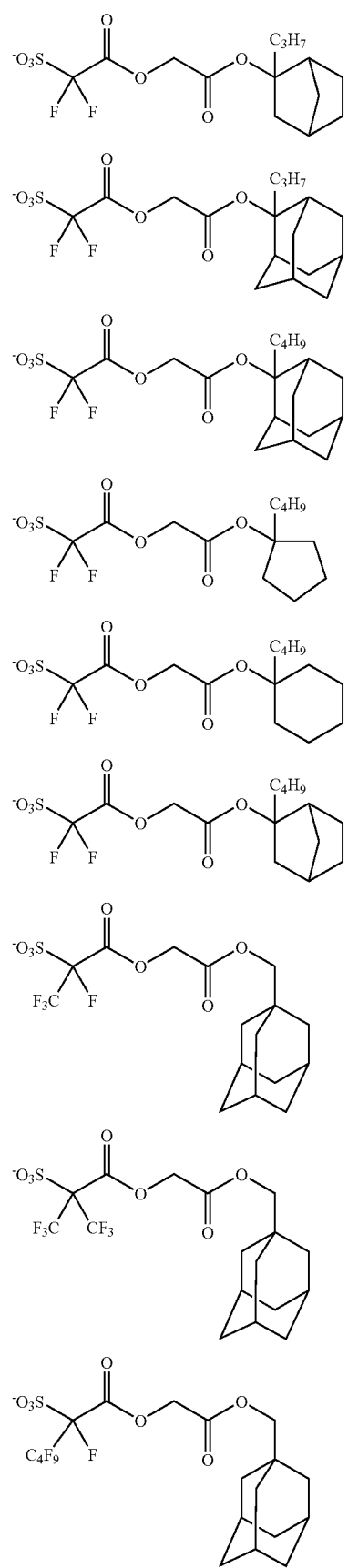
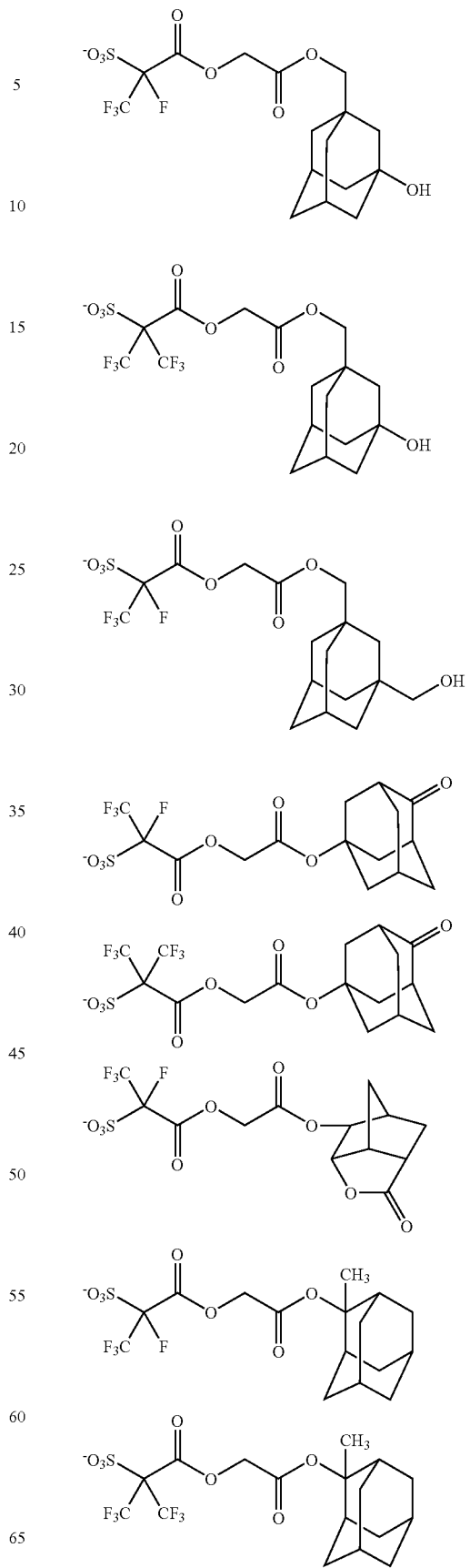

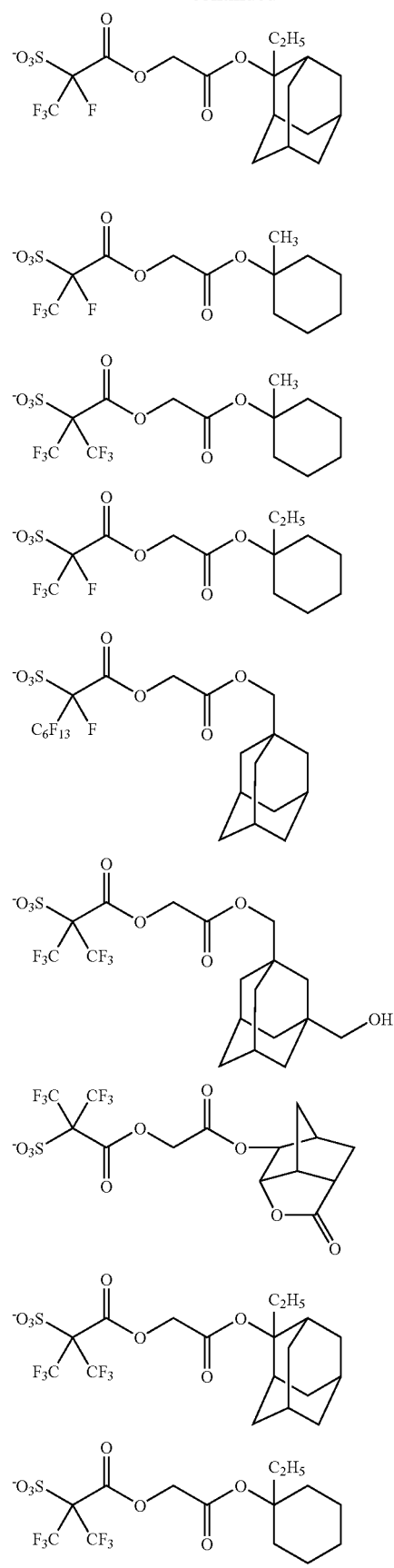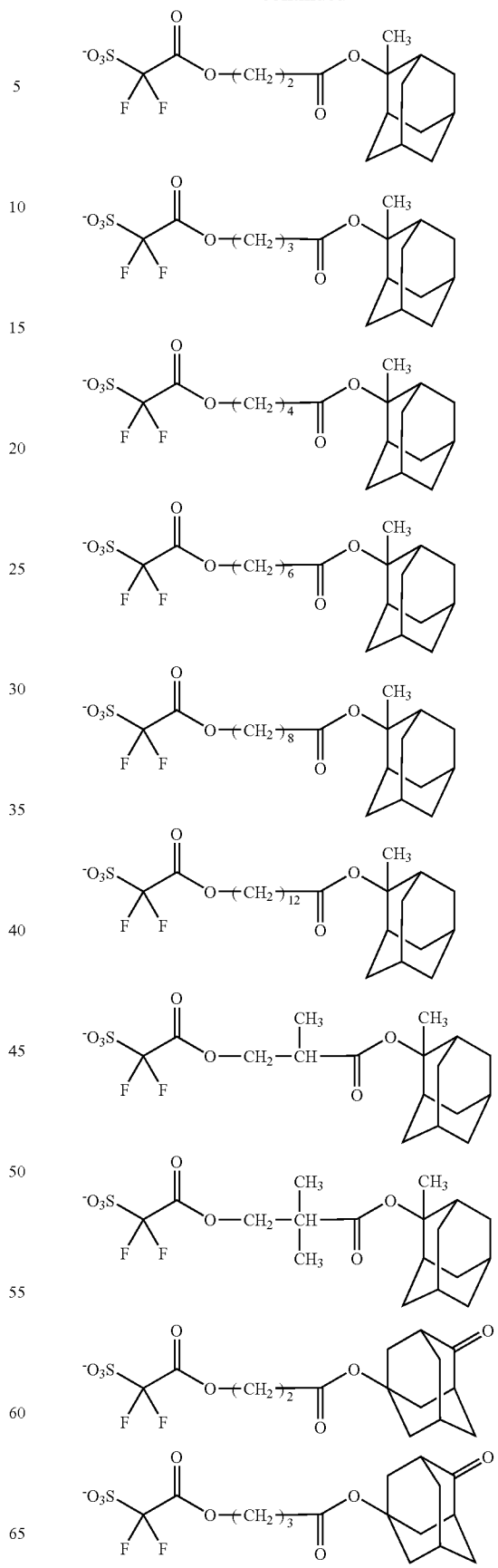

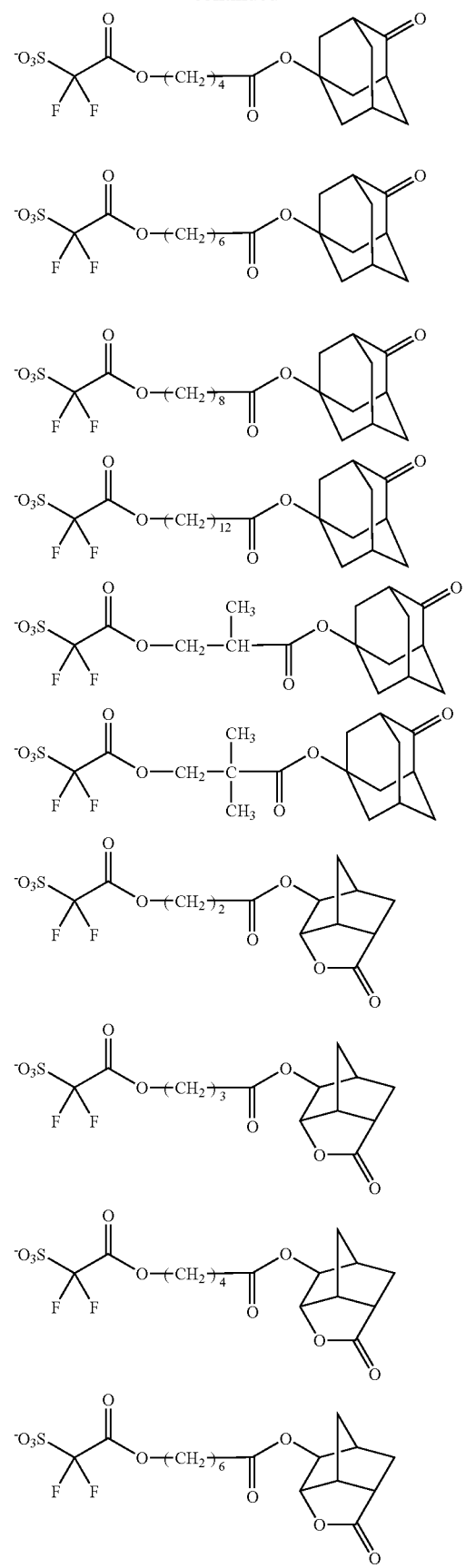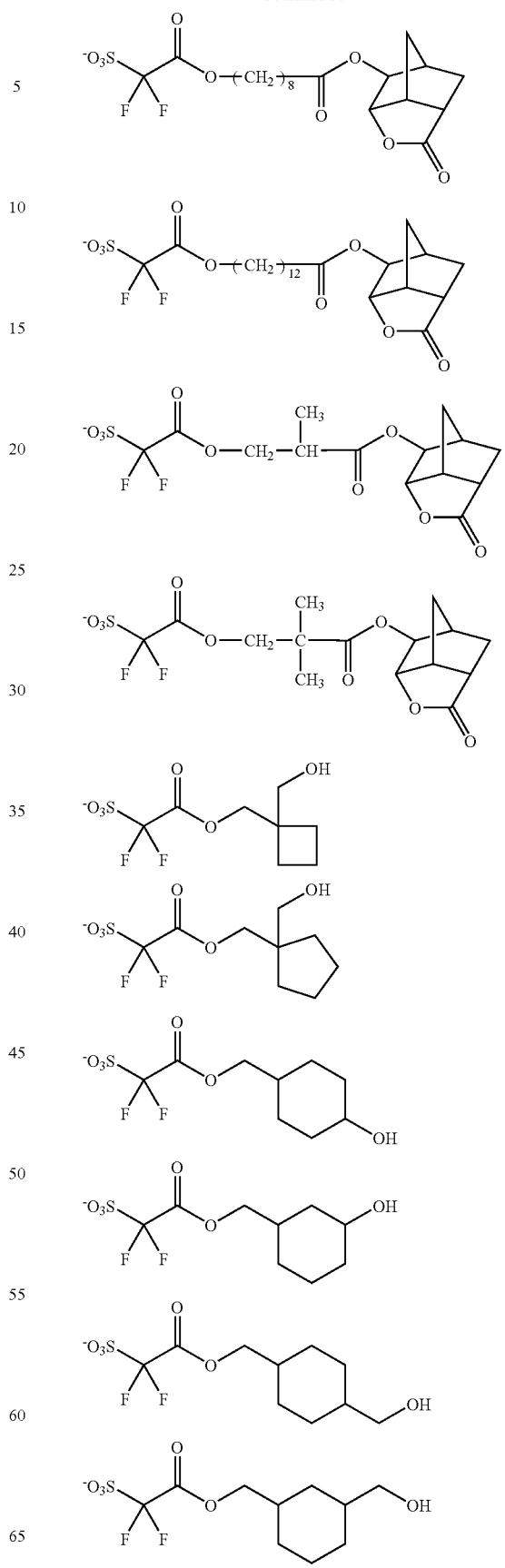

33
-continued
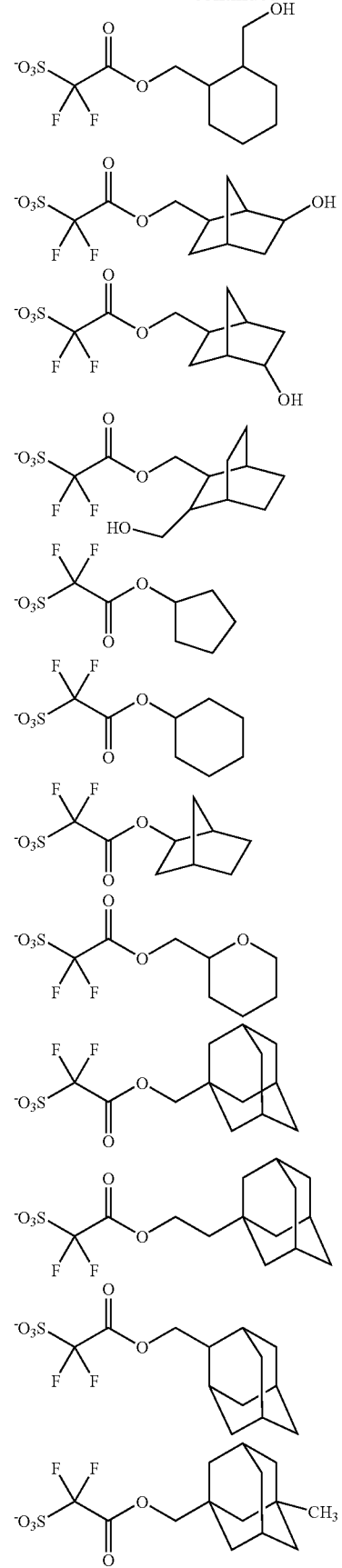
34
-continued
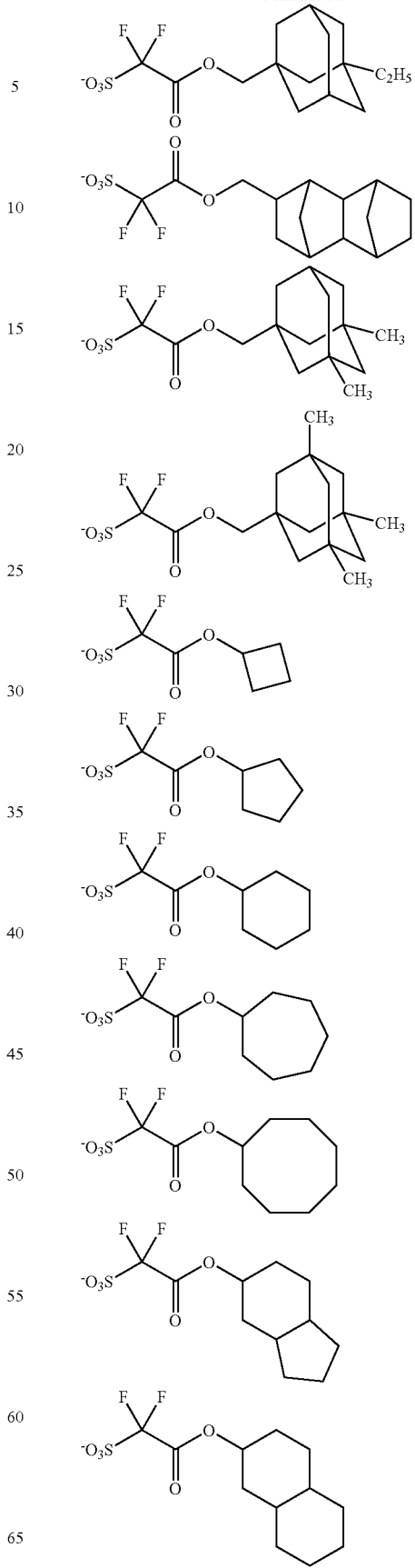

-continued
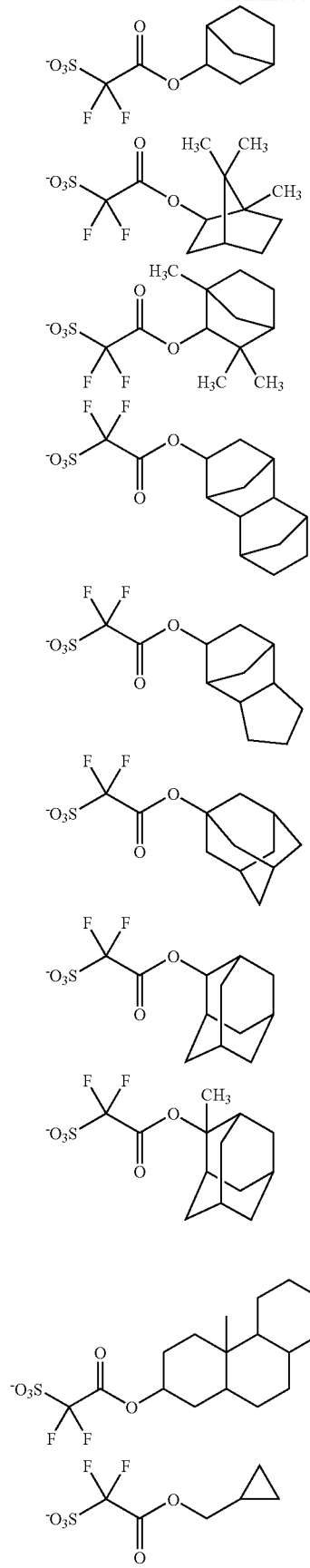
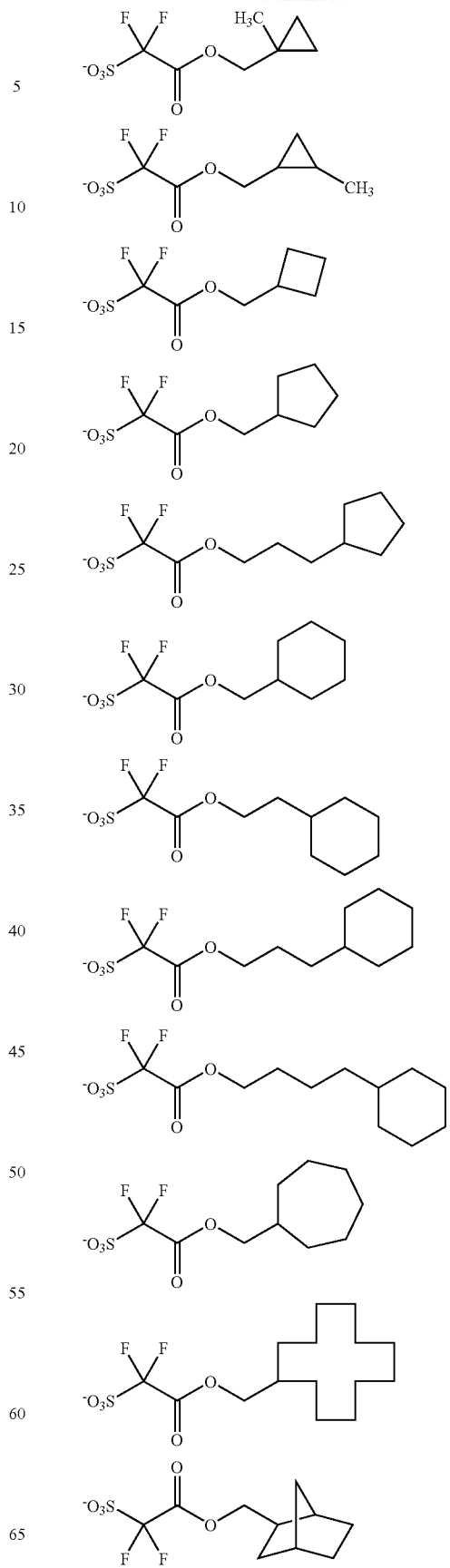

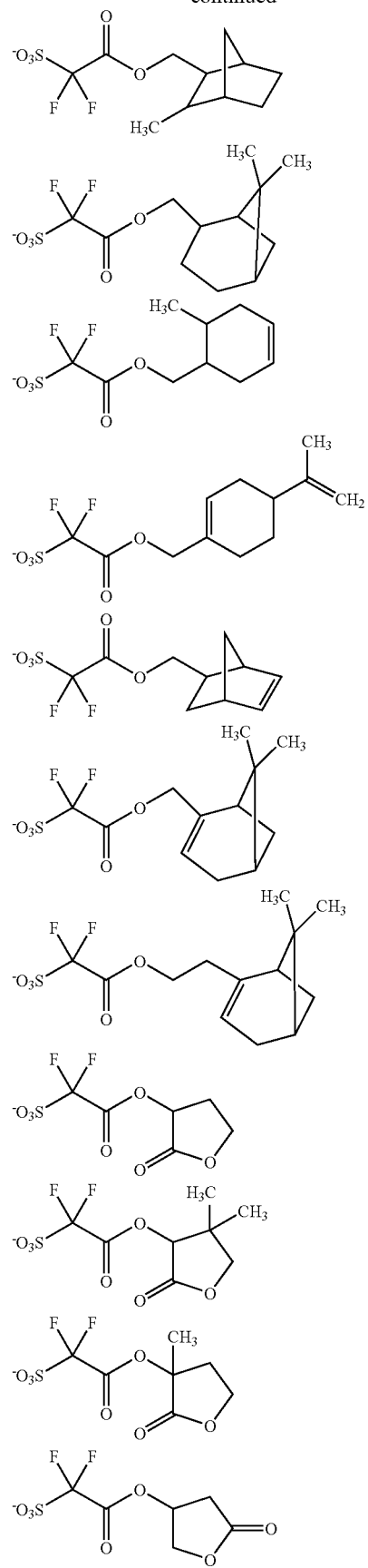
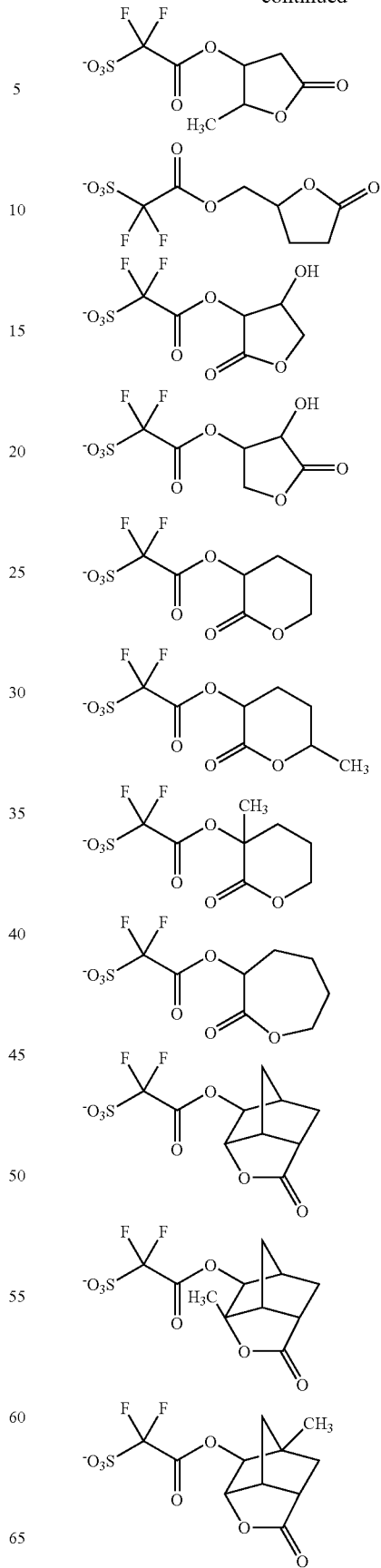

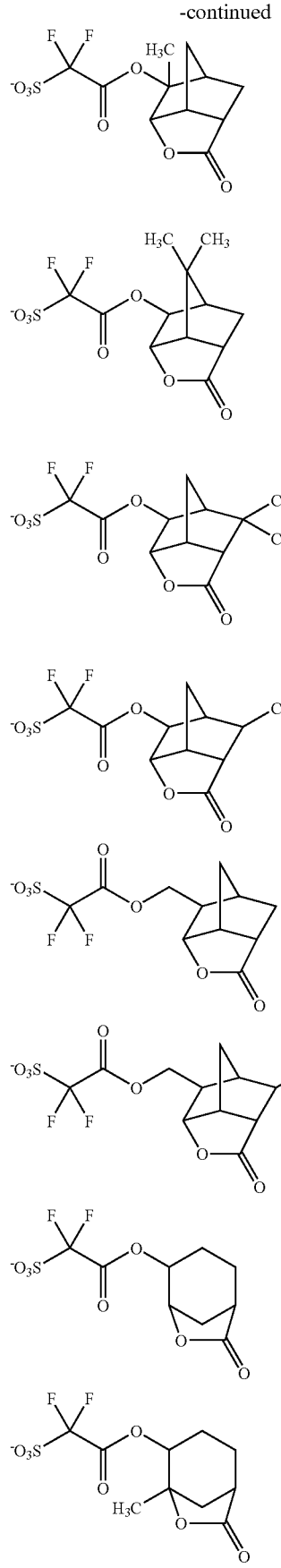
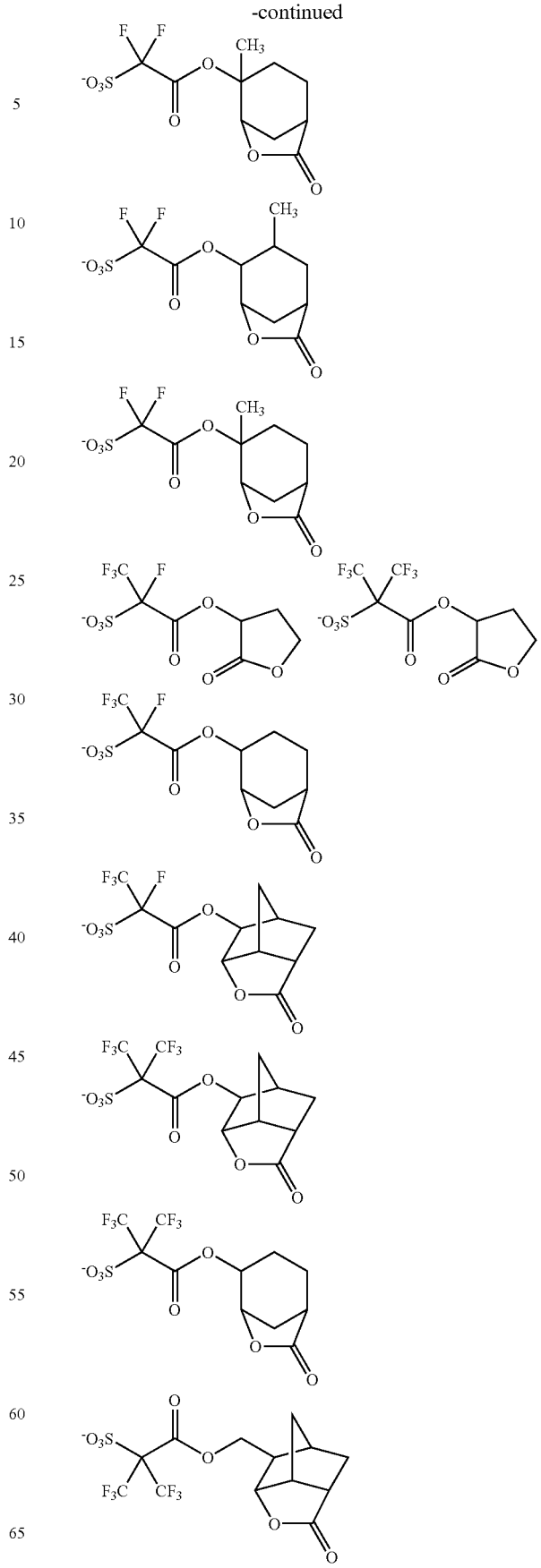

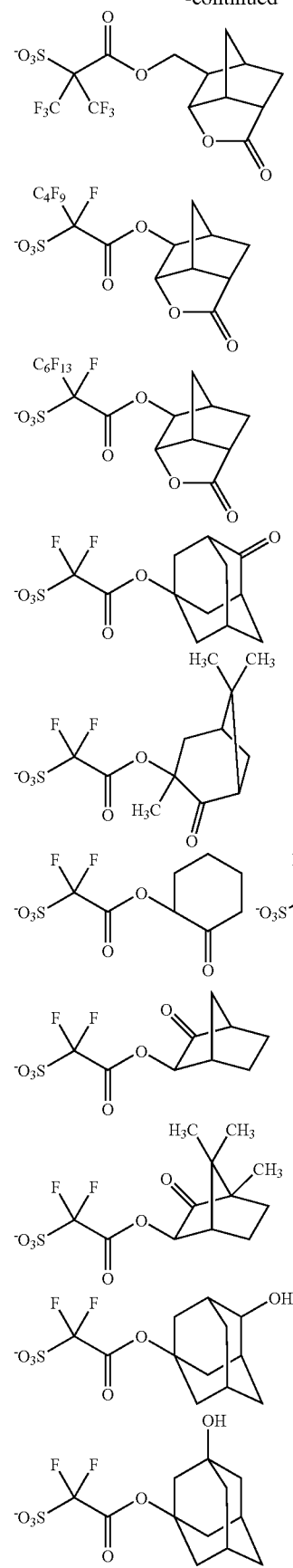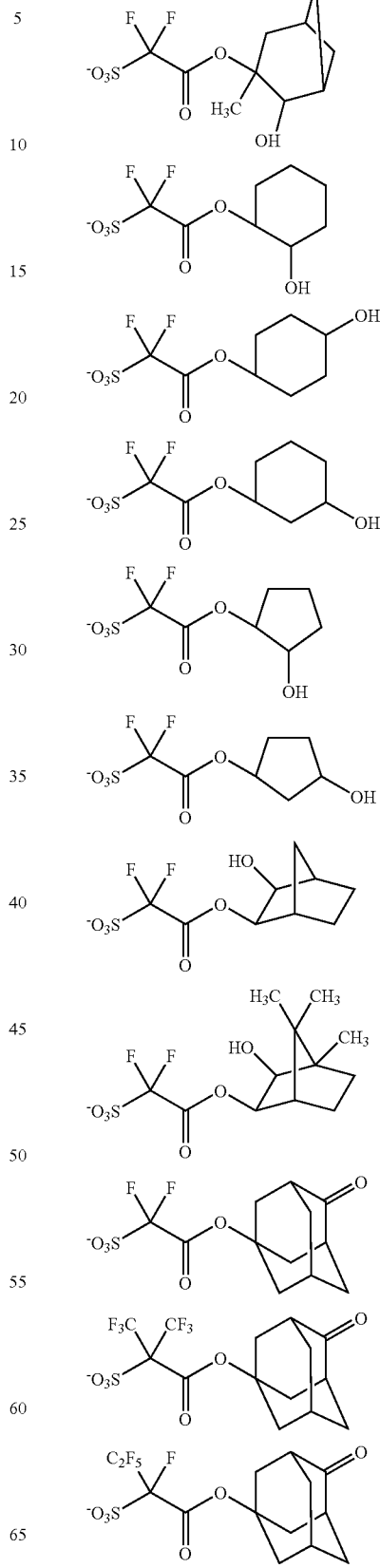

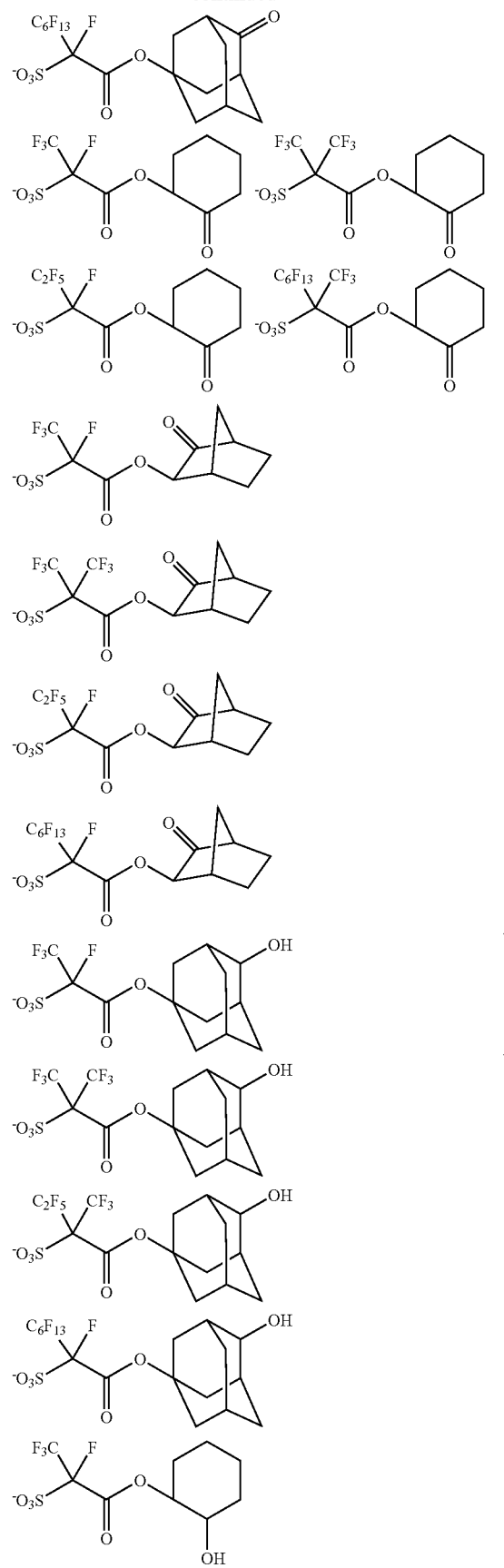
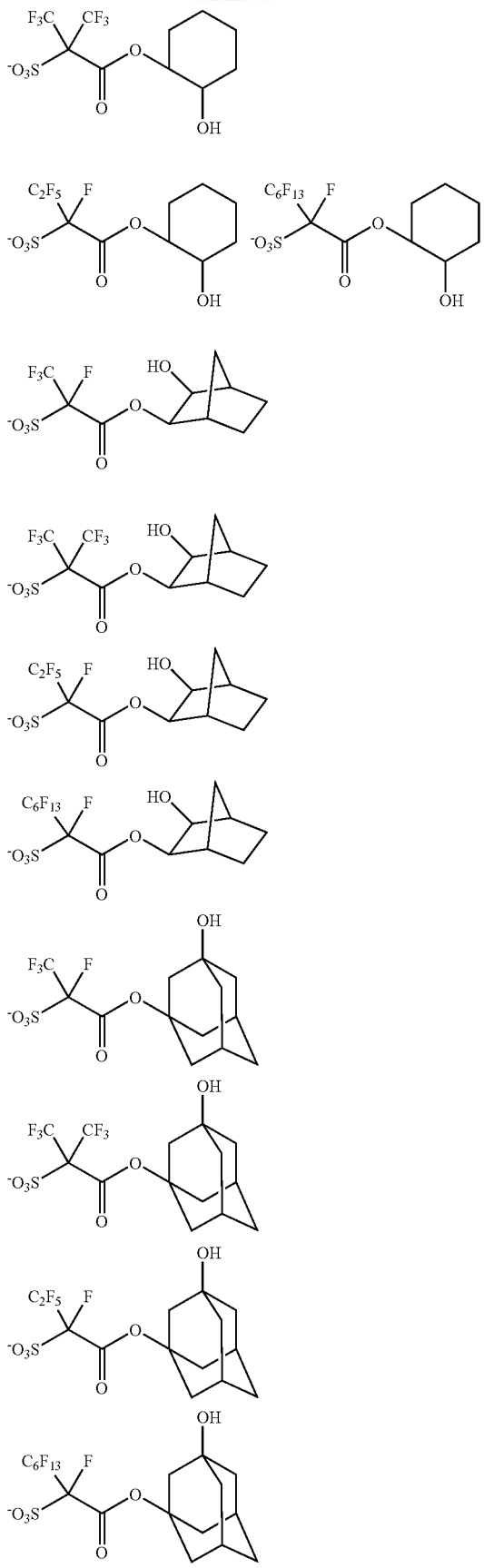

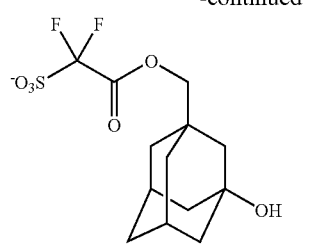
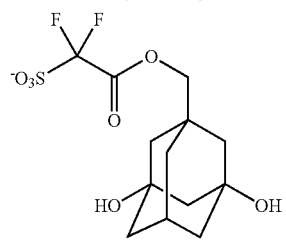
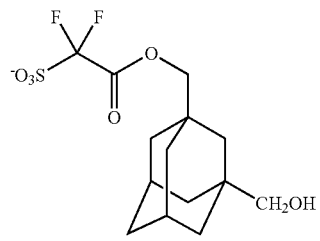
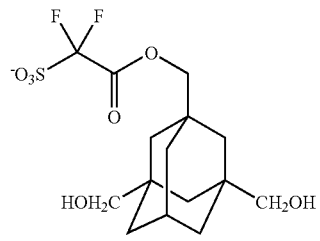
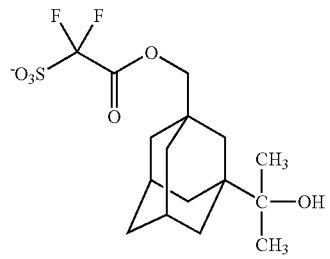
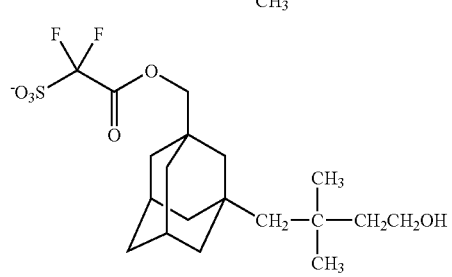
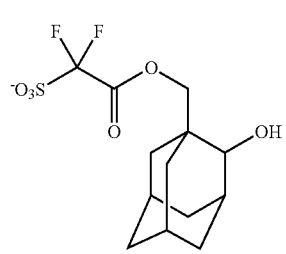
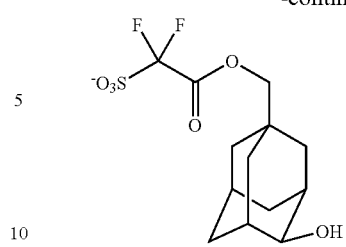
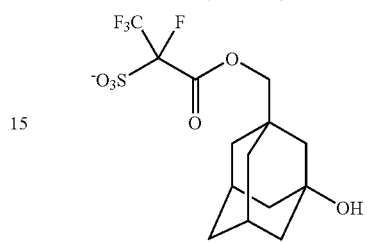
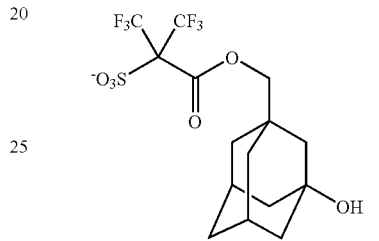
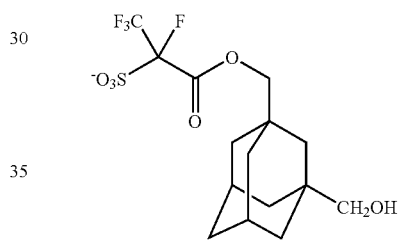
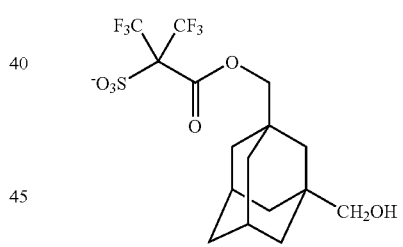
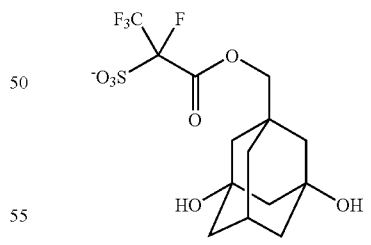
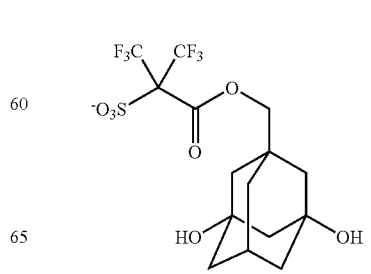

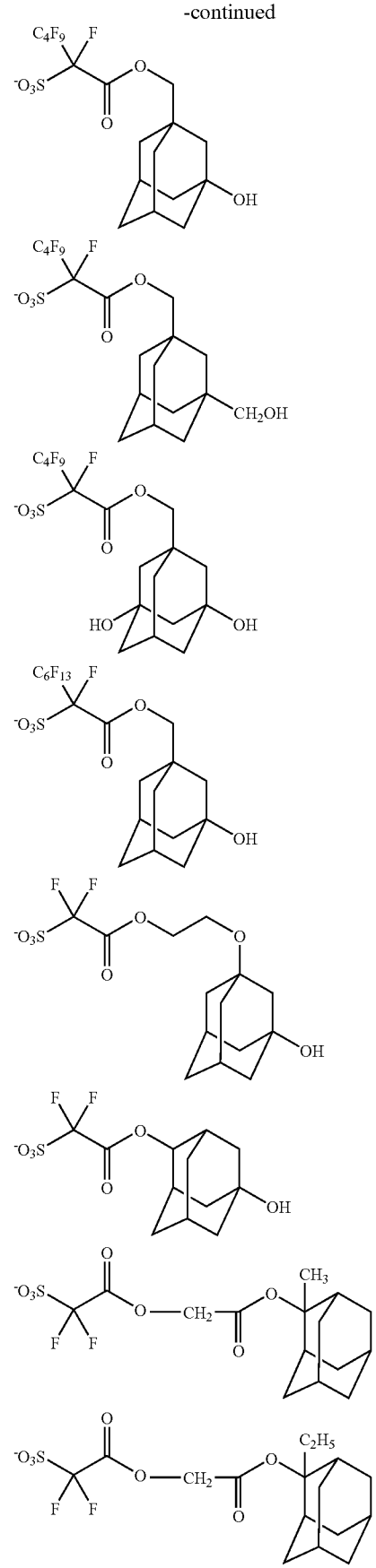
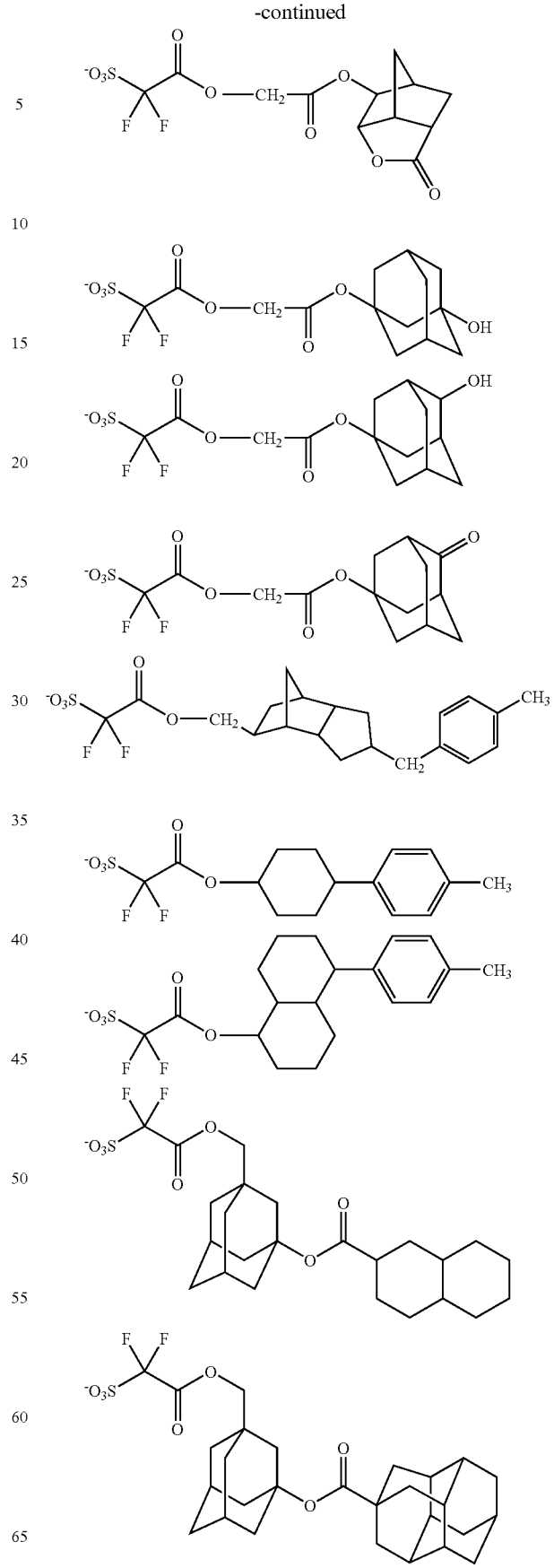

49
-continued
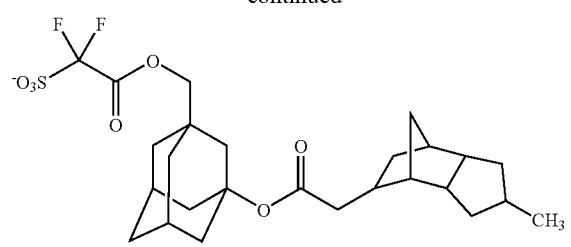
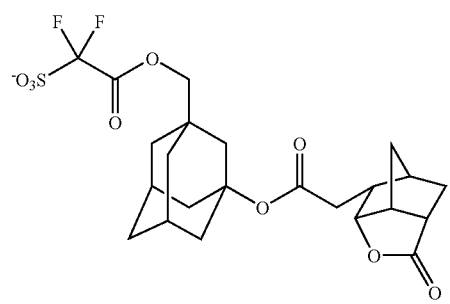
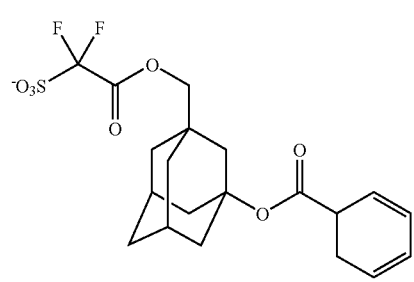
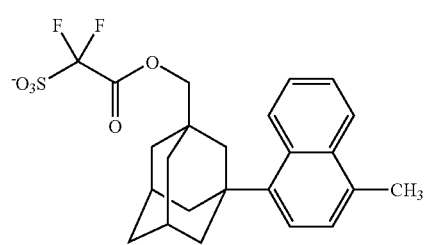
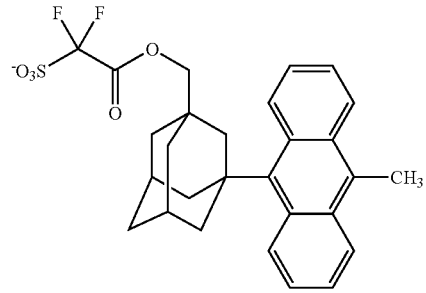
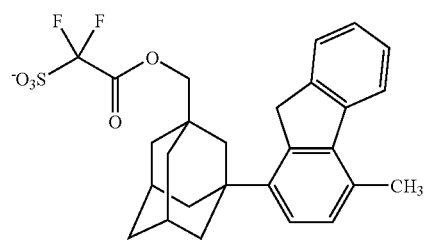
50
-continued
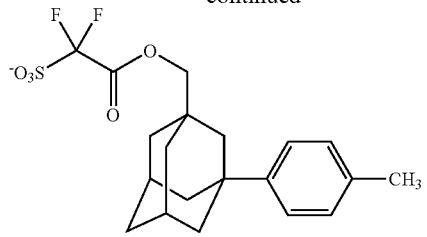
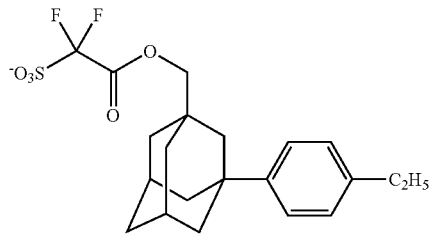
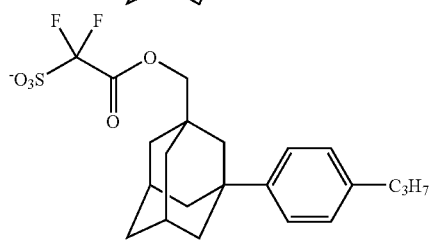
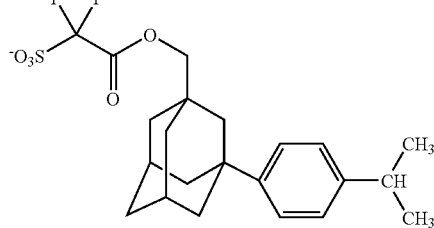
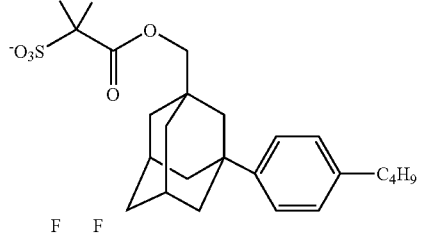
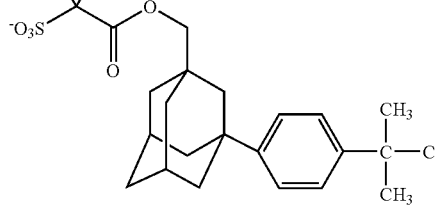
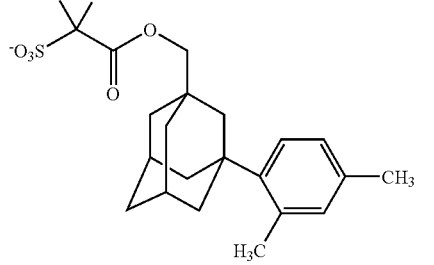

51
-continued
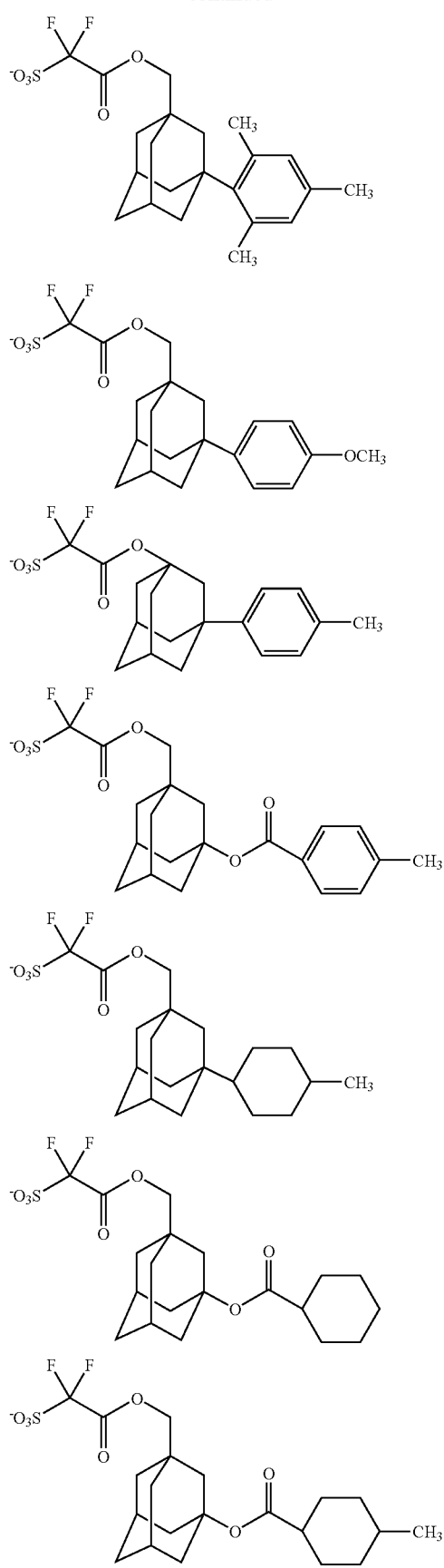
52
-continued
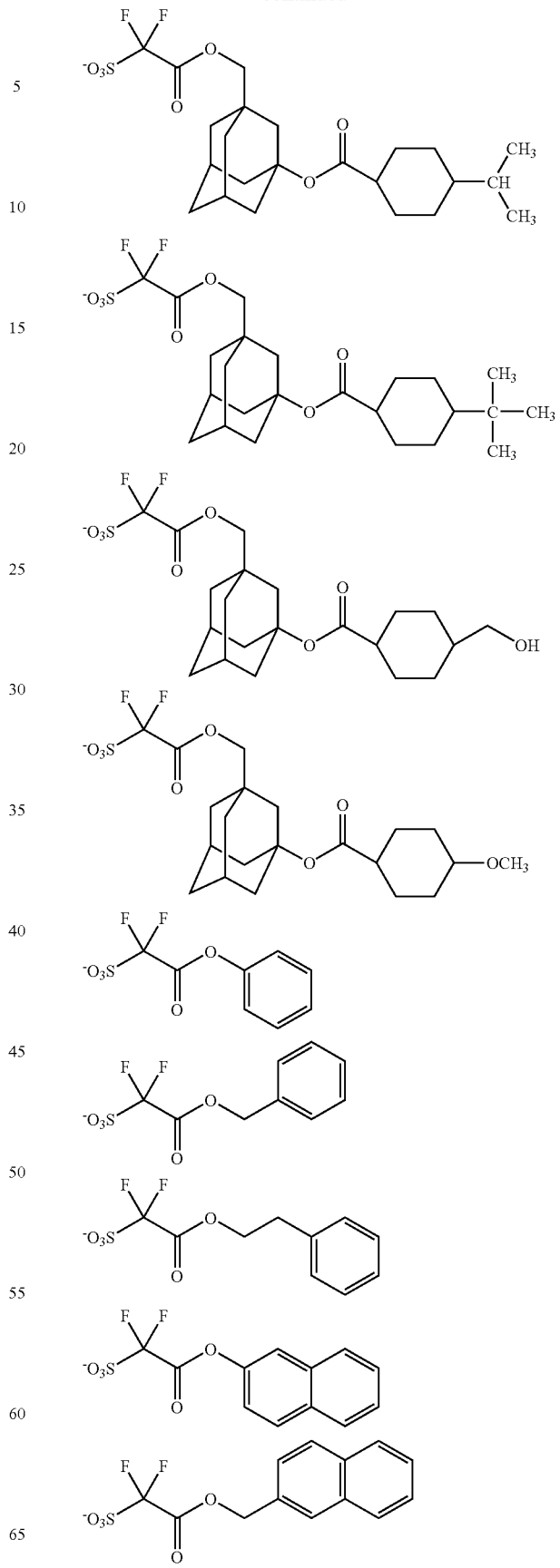

53
-continued
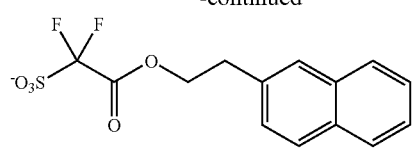
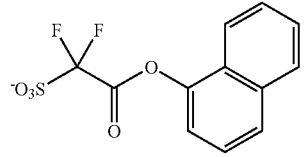
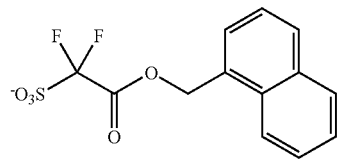
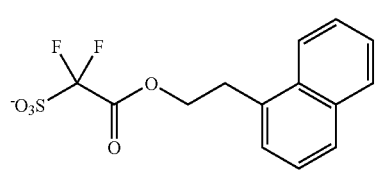
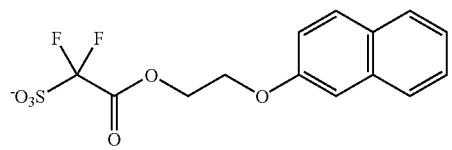
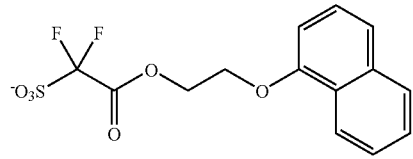
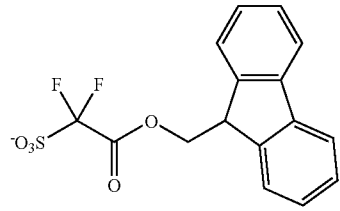
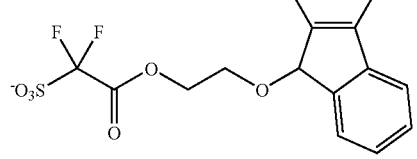
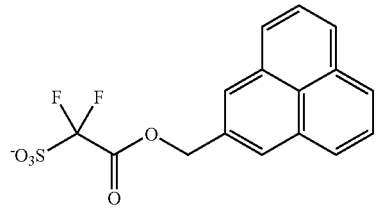
54
-continued
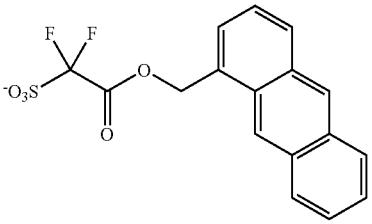
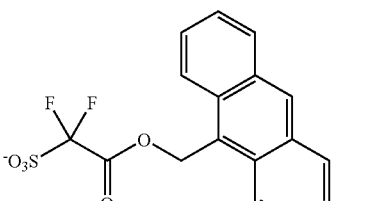
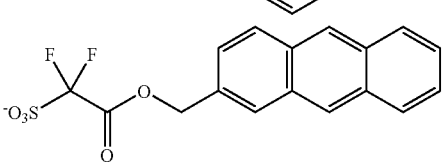
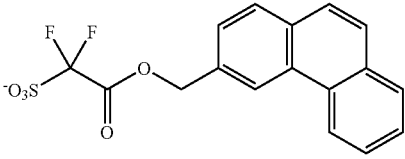
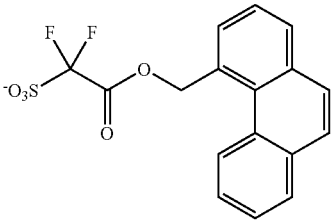
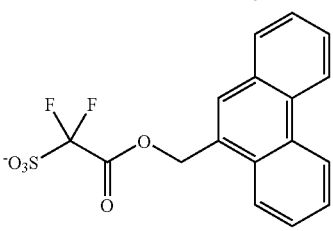
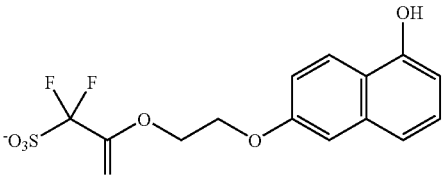
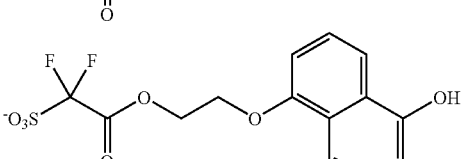
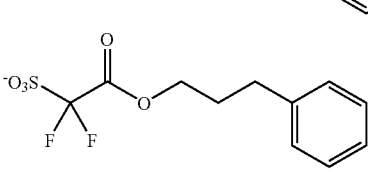

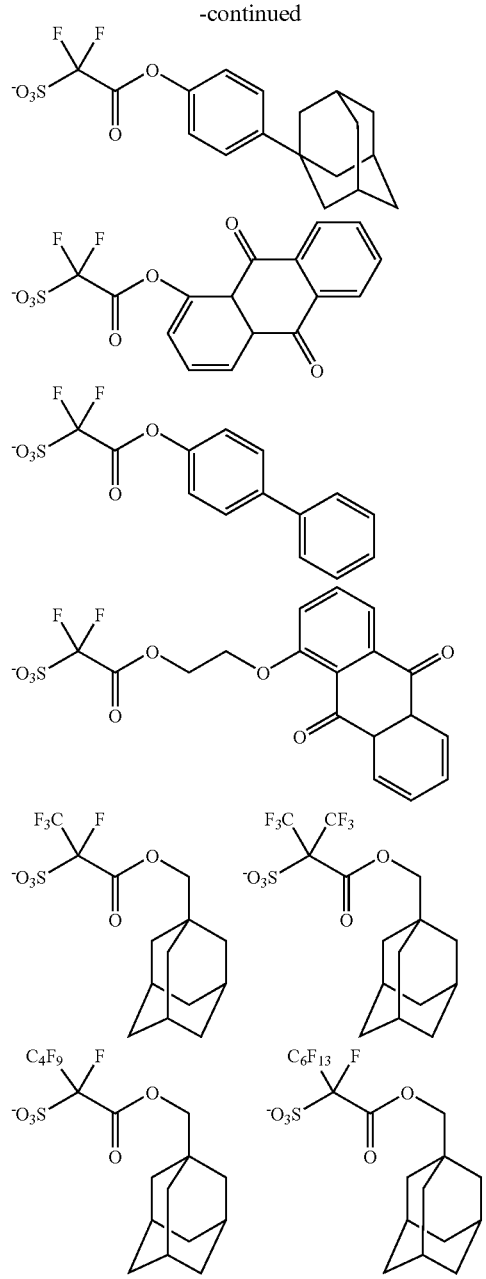

Among Salt (V), a salt represented by the formula (VI):

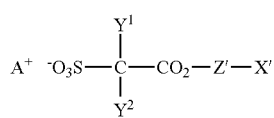

wherein $Y^1$, $Y^2$ and $A^+$ are the same meanings as defined above, $Z'$ represents a single bond or a C1-C4 alkylene group, and $X'$ represents a C3-C30 monocyclic or polycyclic hydrocarbon group having a hydroxyl group or a carbonyl group, and one or more hydrogen atoms in the monocyclic or polycyclic hydrocarbon group may be replaced by a C1-C6 alkoxy group, a C1-C4 perfluoroalkyl group, a C1-C6 hydroxyalkyl group, a hydroxyl group or a cyano group (hereinafter, simply referred to as Salt (VI)) is preferable.

Examples of the C1-C6 alkoxy group, the C1-C4 perfluoroalkyl group and the C1-C6 hydroxyalkyl group in X' include the same groups as described above, respectively.

Examples of the C1-C4 alkylene group in Z' include a methylene group, an ethylene group, a trimethylene group and a tetramethylene group. Z' is preferably a single bond, a methylene group or an ethylene group, and is more preferable a single bond or a methylene group.

Examples of X' include a C4-C8 cycloalkyl group such as a cyclobutyl group, a cyclopentyl group, a cyclohexyl group and a cyclooctyl group, an adamantyl group, and a norbornyl group, in all of which one or more hydrogen atoms may be replaced by the C1-C6 alkoxy group, the C1-C4 perfluoroalkyl group, the C1-C6 hydroxyalkyl group, a hydroxyl group or a cyano group.

Specific examples of X' include a 2-oxocyclopentyl group, a 2-oxocyclohexyl group, a 3-oxocyclopentyl group, a 3-oxocyclohexyl group, a 4-oxocyclohexyl group, a 2-hydroxycyclopentyl group, a 2-hydroxycyclohexyl group, a 3-hydroxycyclopentyl group, a 3-hydroxycyclohexyl group, a 4-hydroxycyclohexyl group, a 4-oxo-2-adamantyl group, a 3-hydroxy-1-adamantyl group, a 4-hydroxy-1-adamantyl group, a 5-oxonorbornan-2-yl group, a 1,7,7-trimethyl-2-oxonorbornan-2-yl group, a 3,6,6-trimethyl-2-oxo-bicyclo[3.1.1]heptan-3-yl group, a 2-hydroxy-norbornan-3-yl group, a 1,7,7-trimethyl-2-hydroxynorbornan-3-yl group, a 3,6,6-trimethyl-2-hydroxybicyclo[3.1.1]heptan-3-yl group, and the following groups (in the following formulae, straight line with an open end shows a bond which is extended from an adjacent group).

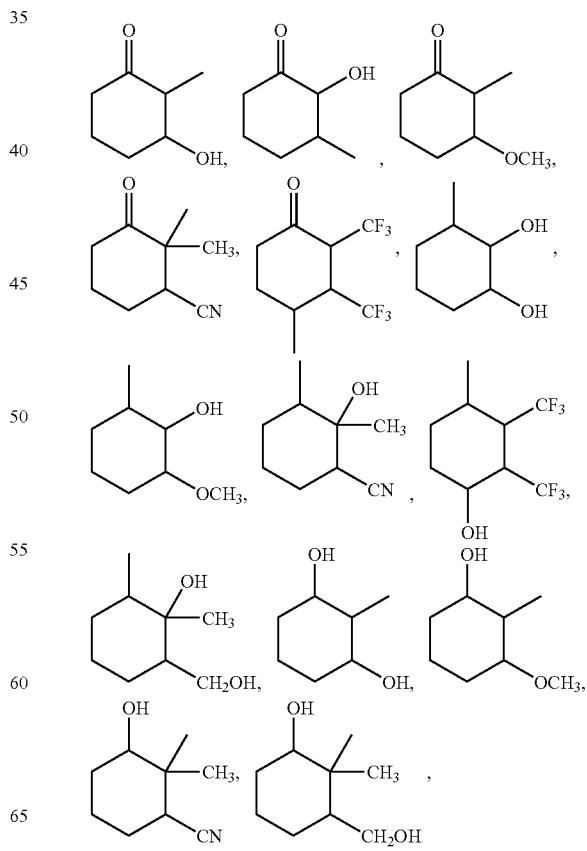

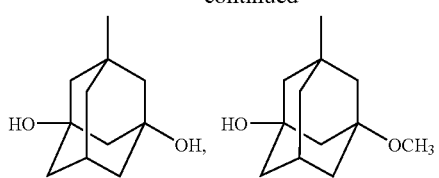
Specific examples of the anion part of Salt (VI) include the followings.
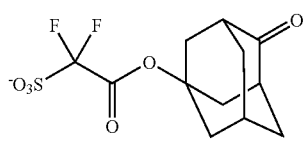
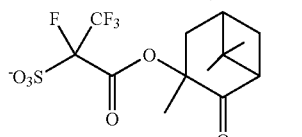
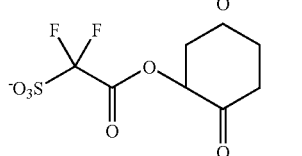
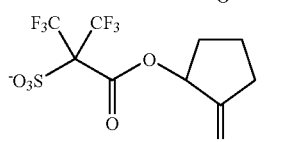
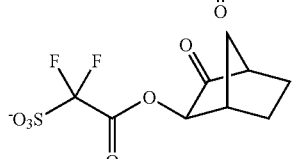
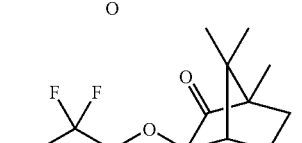
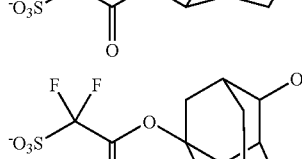
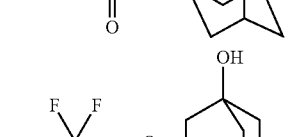
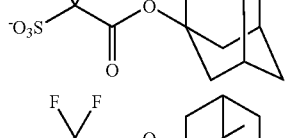
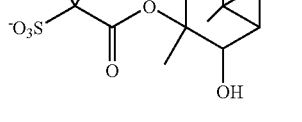
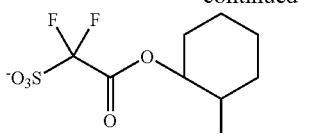
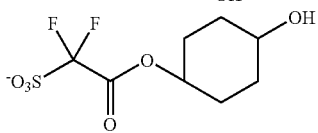
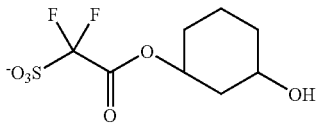
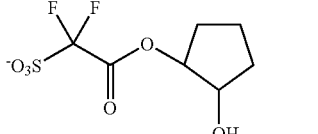
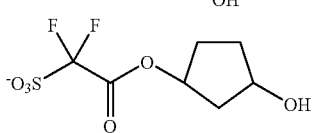
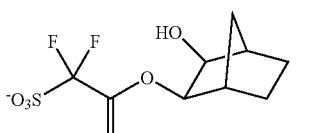
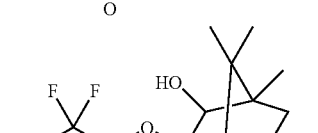
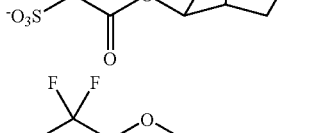
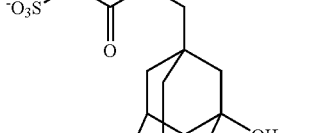
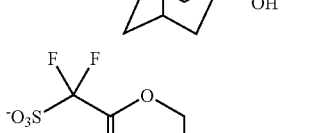
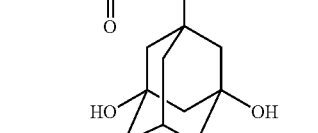
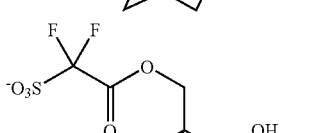
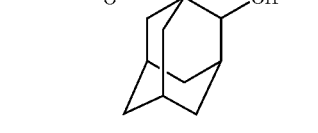

-continued

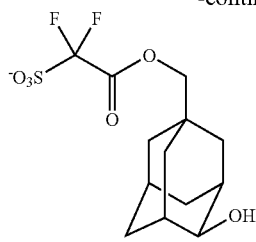

Other examples of the acid generator include a salt represented by the formula (VIII):

$$A^{+-}O_3S-R''$$  (VIII)

wherein R'' represents a linear or branched chain C1-C6 perfluoroalkyl group and $A^+$ is the same as defined above (hereinafter, simply referred to as Salt (VIII)).

In Salt (VIII), examples of the linear or branched chain C1-C6 perfluoroalkyl group include a trifluoromethyl group, a pentafluoroethyl group, a heptafluoropropyl group, a nonafluorobutyl group and a tridecafluorohexyl group.

Specific examples of the anion part of Salt (VIII) include the followings.

$CF_3-SO_3^-$ $CF_3CF_2CF_2-SO_3^-$ $CF_3CF_2CF_2CF_2-SO_3^-$ $CF_3CF_2CF_2CF_2CF_2CF_2-SO_3^-$

In Salt (V), Salt (VI) and Salt (VIII), $A^+$ represents an organic counter ion. Examples of the organic counter ion include a cation represented by the formula (IXz):

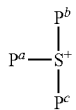

(IXz)

wherein $P^a$, $P^b$ and $P^c$ each independently represent a C1-C30 linear or branched chain alkyl group which may have one or more substituents selected from the group consisting of a hydroxyl group, a C3-C12 cyclic hydrocarbon group and a C1-C12 alkoxy group, or a C3-C30 cyclic hydrocarbon group which may have one or more substituents selected from the group consisting of a hydroxyl group and a C1-C12 alkoxy group (hereinafter, simply referred to as the cation (IXz)), a cation represented by the formula (IXb):

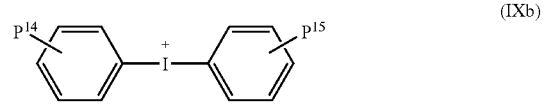

(IXb)

wherein $P^{14}$ and $P^{15}$ each independently represent a hydrogen atom, a hydroxyl group, a C1-C12 alkyl group or a C1-C12 alkoxy group (hereinafter, simply referred to as the cation (IXb)), a cation represented by the formula (IXc):

(IXc)

wherein $P^{16}$ and $P^{17}$ each independently represent a C1-C12 alkyl group or a C3-C12 cycloalkyl group, or $P^{16}$ and $P^{17}$ are bonded to form a C3-C12 divalent acyclic hydrocarbon group which forms a ring together with the adjacent $S^+$, and one or more —$CH_2$— in the divalent acyclic hydrocarbon group may be replaced by —CO—, —O— or —S—, $P^{18}$ represents a hydrogen atom, $P^{19}$ represents a C1-C12 alkyl group, a C3-C12 cycloalkyl group or an aromatic group which may have one or more substituents, or $P^{18}$ and $P^{19}$ are bonded to form a divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S— (hereinafter, simply referred to as the cation (IXc)); and a cation represented by the formula (IXd):

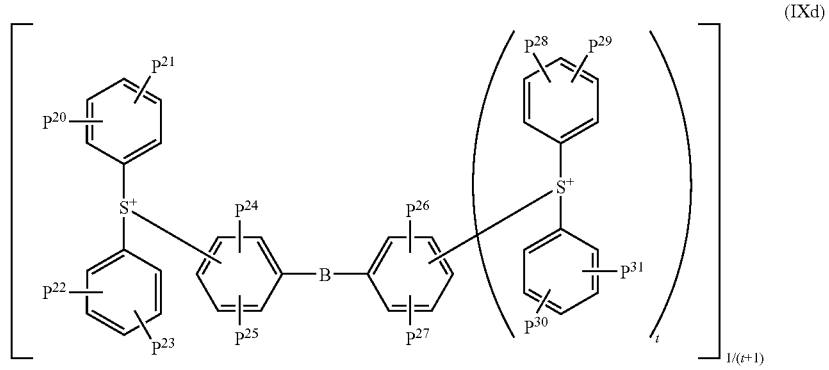

(IXd)

wherein $P^{20}$, $P^{21}$, $P^{22}$, $P^{23}$, $P^{24}$, $P^{25}$, $P^{26}$, $P^{27}$, $P^{28}$, $P^{29}$, $P^{30}$ and $P^{31}$ each independently represent a hydrogen atom, a hydroxyl group, a C1-C12 alkyl group or a C1-C12 alkoxy group, B represents a sulfur atom or an oxygen atom and t represents 0 or 1 (hereinafter, simply referred to as the cation (IXd)).

Examples of the C1-C12 alkoxy group in the cations (IXz), (IXb) and (IXd) include a methoxy group, an ethoxy group, a propoxy group, an isopropoxy group, a butoxy group, an isobutoxy group, a sec-butoxy group, a tert-butoxy group, a pentyloxy group, a hexyloxy group, a octyloxy group and a 2-ethylhexyloxy group.

Examples of the C3-C12 cyclic hydrocarbon group in the cation (IXz) include a cyclopentyl group, a cyclohexyl group, a 1-adamantyl group, a 2-adamantyl group, a phenyl group, a 2-methylphenyl group, a 4-methylphenyl group, a 1-naphthyl group and a 2-naphthyl group.

Examples of the C1-C30 alkyl group which may have one or more substituents selected from the group consisting of a hydroxyl group, a C3-C12 cyclic hydrocarbon group and a C1-C12 alkoxy group in the cation (IXz) include a methyl group, an ethyl group, a propyl group, an isopropyl group, a butyl group, an isobutyl group, a sec-butyl group, a tert-butyl group, a pentyl group, a hexyl group, a octyl group, a 2-ethylhexyl group and a benzyl group.

Examples of the C3-C30 cyclic hydrocarbon group which may have one or more substituents selected from the group consisting of a hydroxyl group and a C1-C12 alkoxy group in the cation (IXz) include a cyclopentyl group, a cyclohexyl group, a 1-adamantyl group, a 2-adamantyl group, a bicyclohexyl group, a phenyl group, a 2-methylphenyl group, a 4-methylphenyl group, a 4-ethylphenyl group, a 4-isopropylphenyl group, a 4-tert-butylphenyl group, a 2,4-dimethylphenyl group, a 2,4,6-trimethylphenyl group, a 4-hexylphenyl group, a 4-octylphenyl group, a 1-naphthyl group, a 2-naphthyl group, a fluorenyl group, a 4-phenylphenyl group, a 4-hydroxyphenyl group, a 4-methoxyphenyl group, a 4-tert-butoxyphenyl group and a 4-hexyloxyphenyl group.

Examples of the C1-C12 alkyl group in the cations (IXb), (IXc) and (IXd) include a methyl group, an ethyl group, a propyl group, an isopropyl group, a butyl group, an isobutyl group, a sec-butyl group, a tert-butyl group, a pentyl group, a hexyl group, a octyl group and a 2-ethylhexyl group.

Examples of the C3-C12 cycloalkyl group in the cation (IXc) include a cyclopropyl group, a cyclobutyl group, a cyclopentyl group, a cyclohexyl group, a cycloheptyl group, a cyclooctyl group and a cyclodecyl group. Examples of the C3-C12 divalent acyclic hydrocarbon group formed by bonding $P^{16}$ and $P^{17}$ include a trimethylene group, a tetramethylene group and a pentamethylene group. Examples of the ring group formed together with the adjacent $S^+$ and the divalent acyclic hydrocarbon group include a tetramethylenesulfonio group, a pentamethylenesulfonio group and oxybisethylenesulfonio group.

Examples of the aromatic group in the cation (IXc) include a phenyl group, a tolyl group, a xylyl group, a 4-butylphenyl group, a 4-isobutylphenyl group, a 4-tert-butylphenyl group, a 4-cyclohexylphenyl group, a 4-phenylphenyl group, a 1-naphthyl group and a 2-naphthyl group. The aromatic group may have one or more substituents, and examples of the substituents include a C1-C6 alkoxy group such as a methoxy group, an ethoxy group, a propoxy group, a butoxy group, a tert-butoxy group and a hexyloxy group; a C2-C12 acyloxy group such as an acetyloxy group and a 1-adamantylcarbonyloxy group; and a nitro group.

Examples of the divalent acyclic hydrocarbon group formed by bonding $P^{18}$ and $P^{19}$ include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

Examples of the cation (IXz) include the followings:

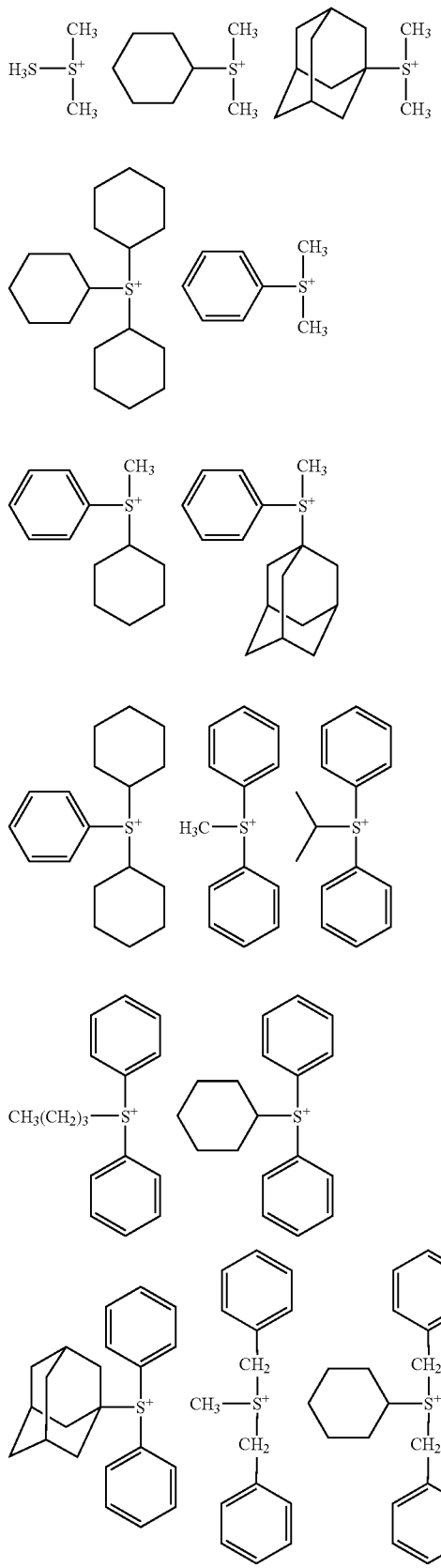

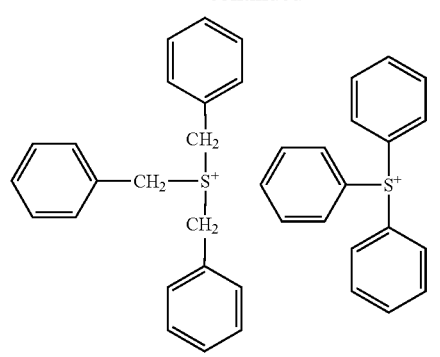
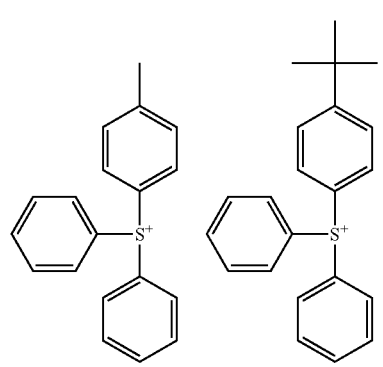
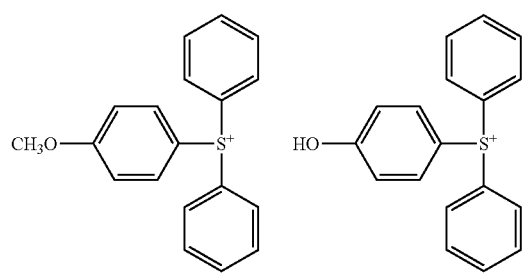
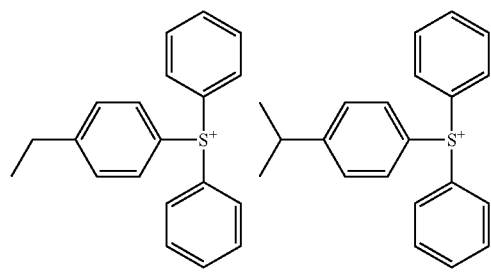
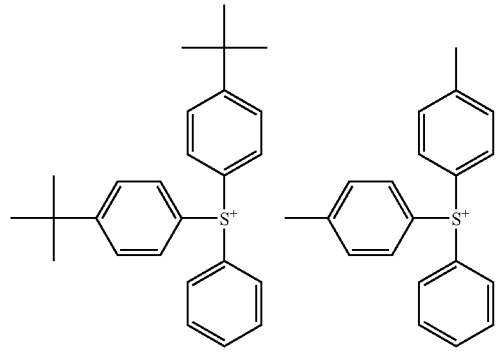
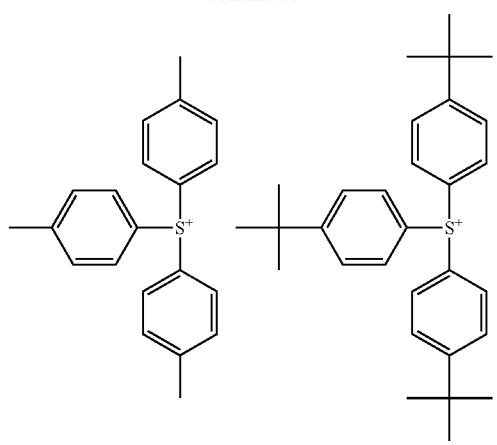
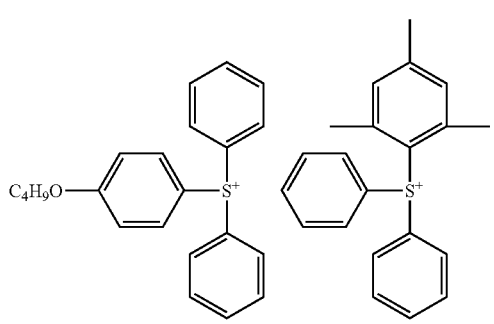
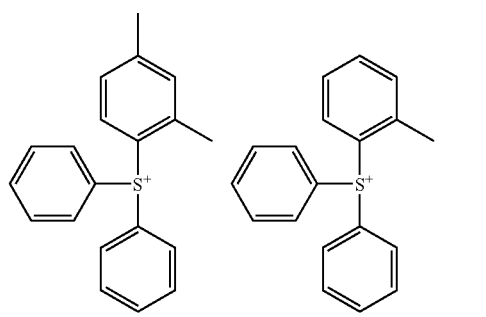
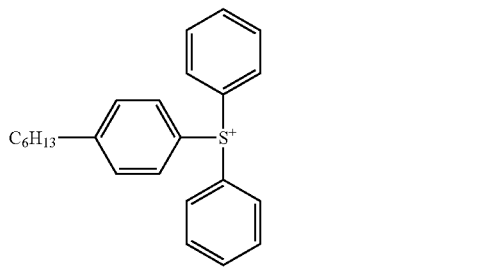
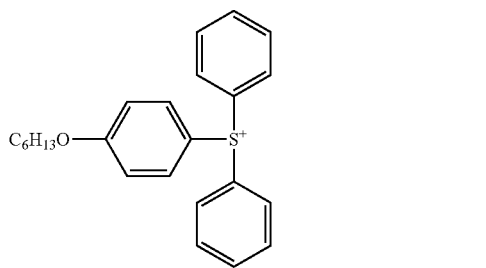

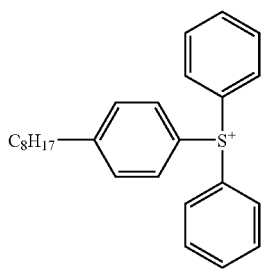
Specific examples of the cation (IXb) include the following:
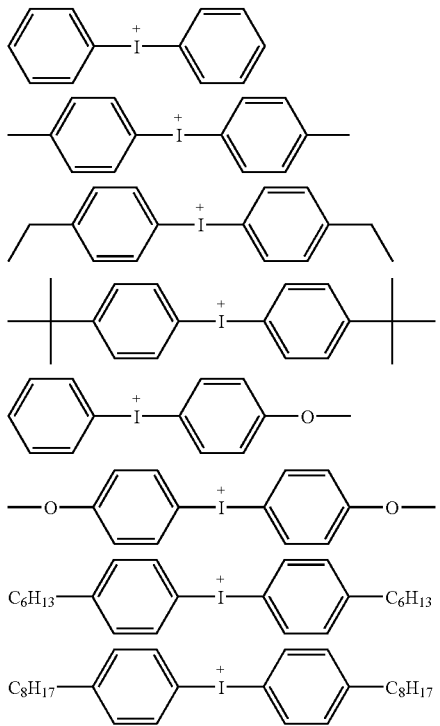
Specific examples of the cation (IXc) include the following:
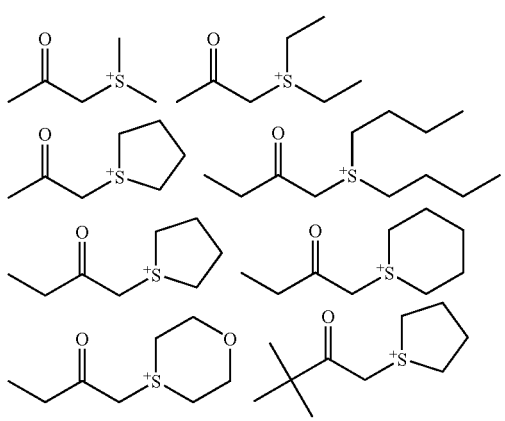
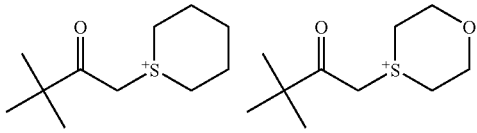
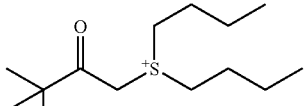
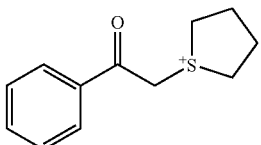
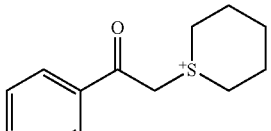
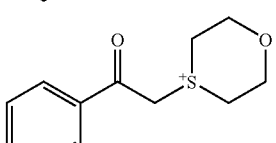
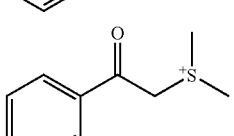
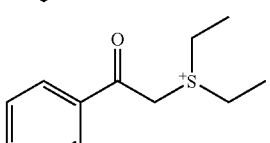
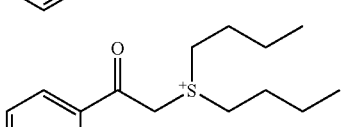
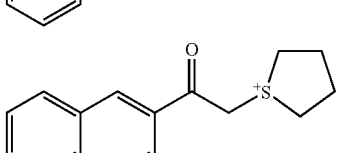
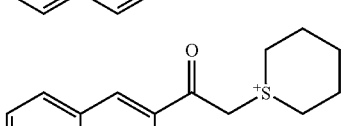
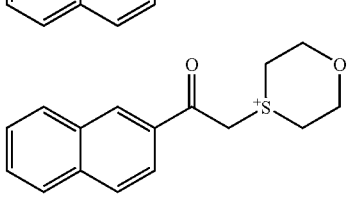

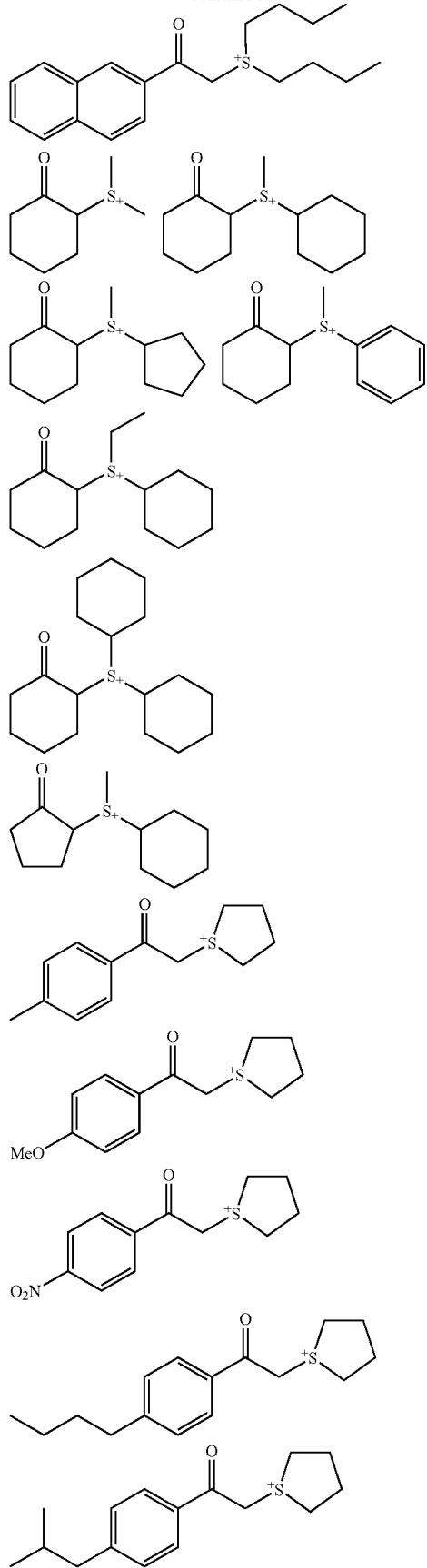
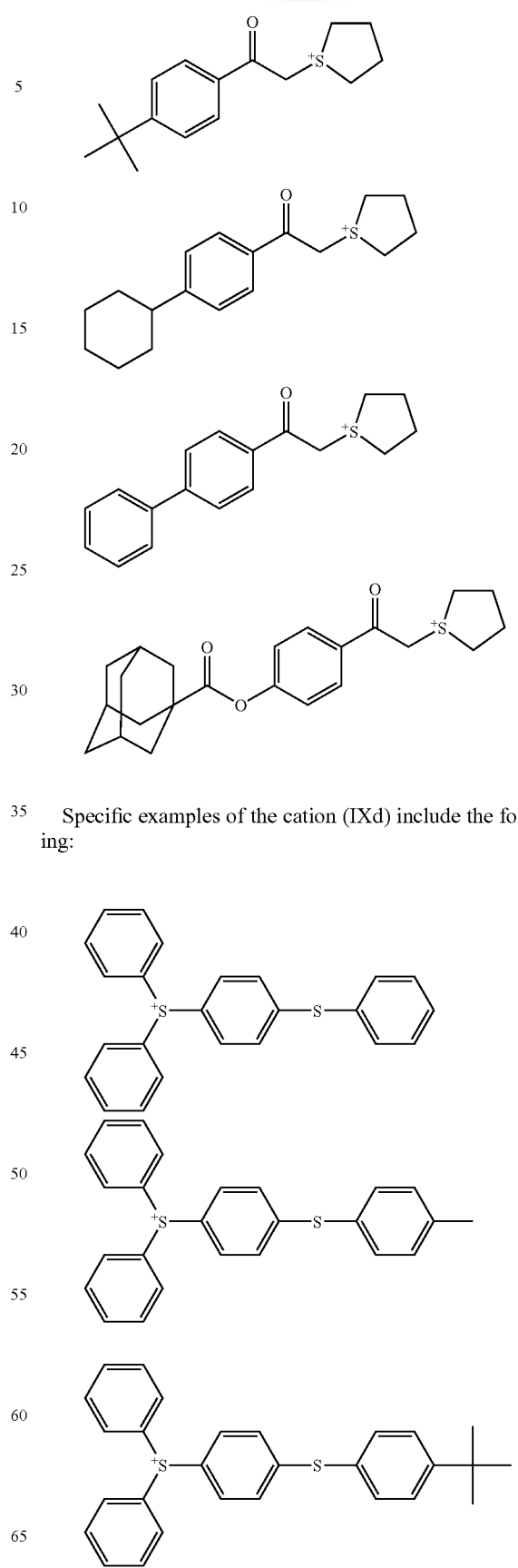
Specific examples of the cation (IXd) include the following:

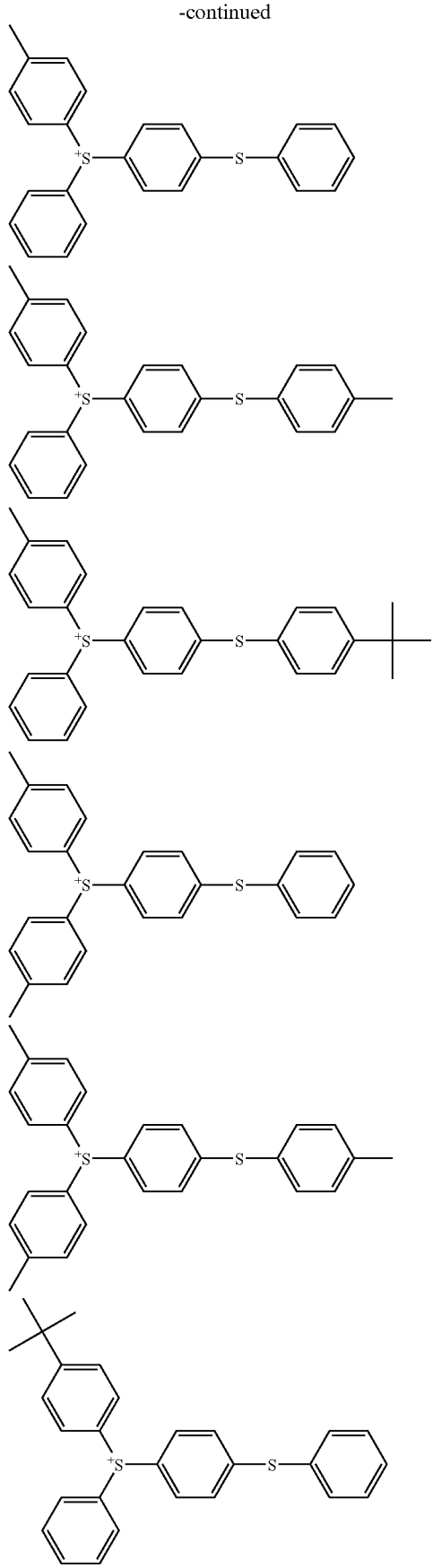
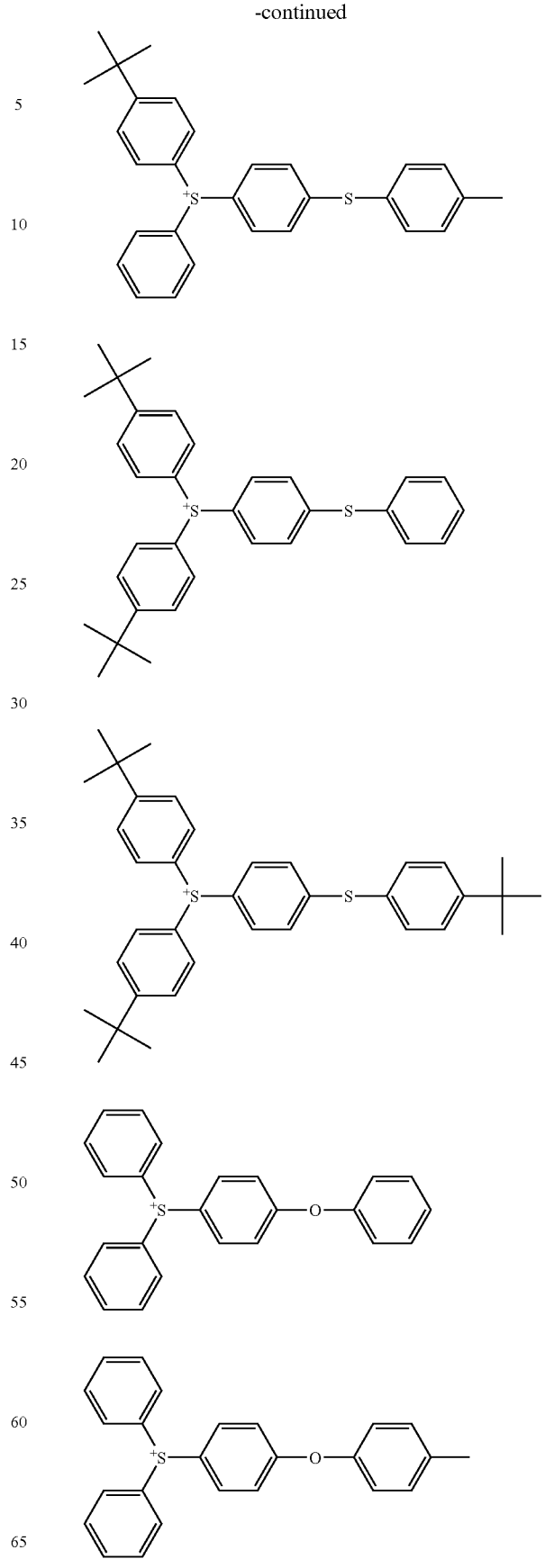

71
-continued
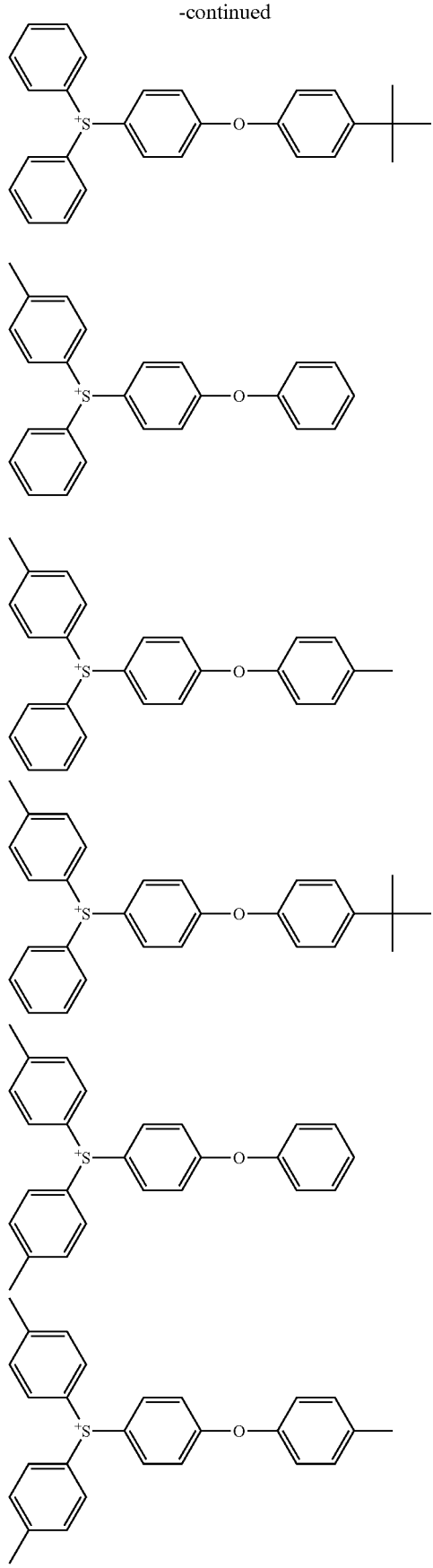
72
-continued
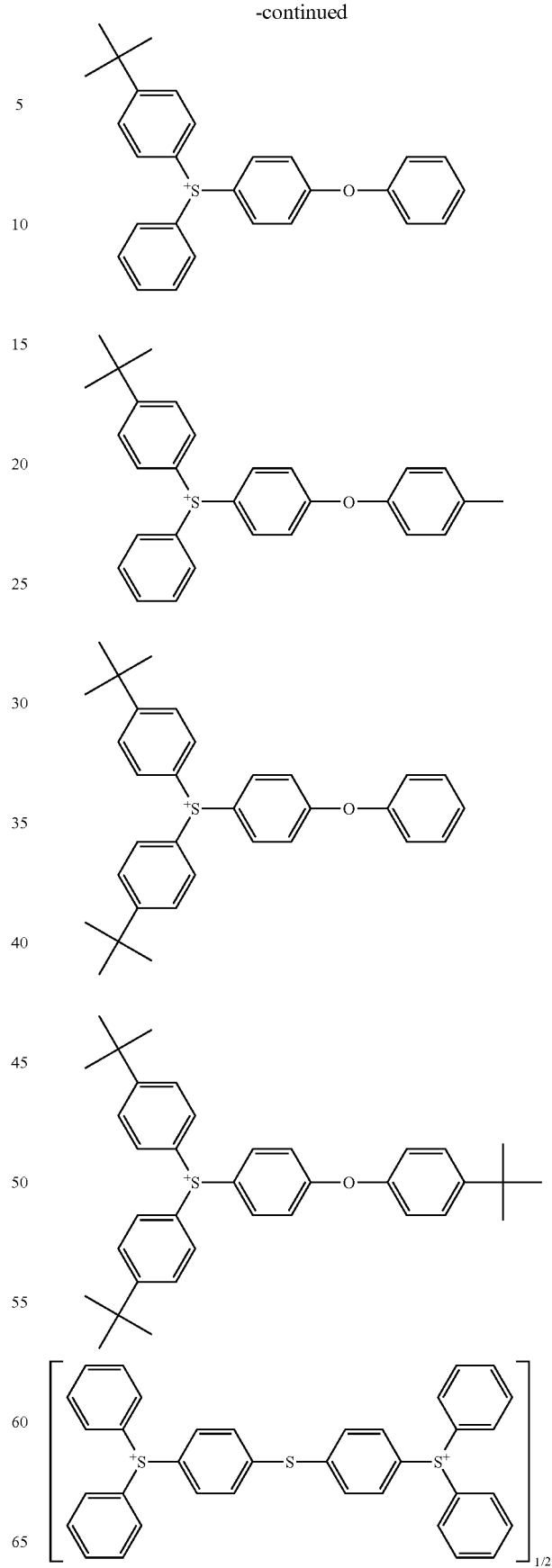

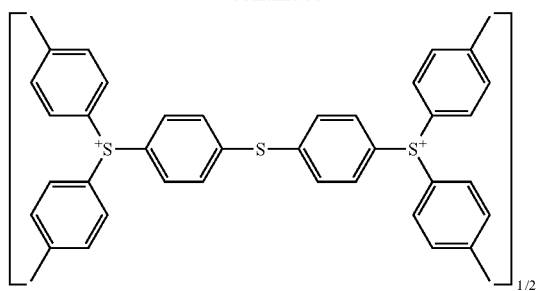
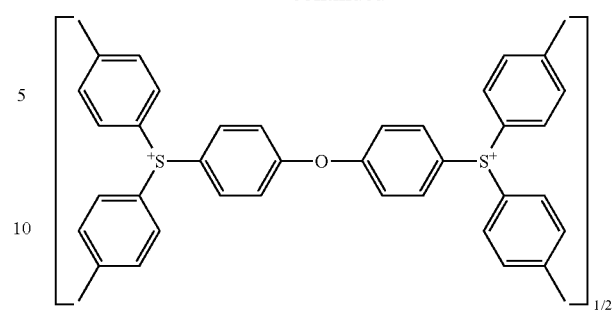
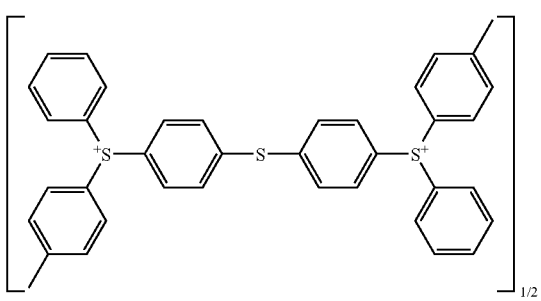
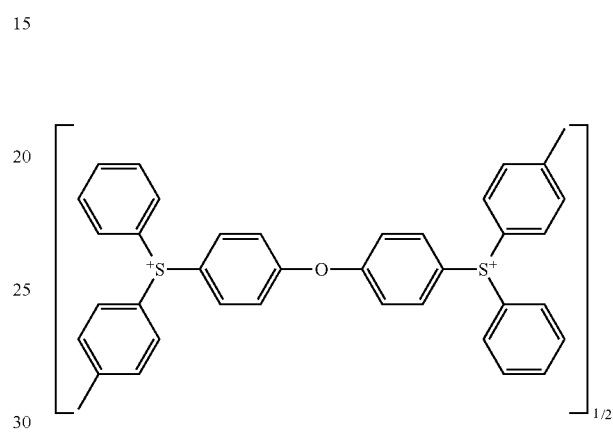
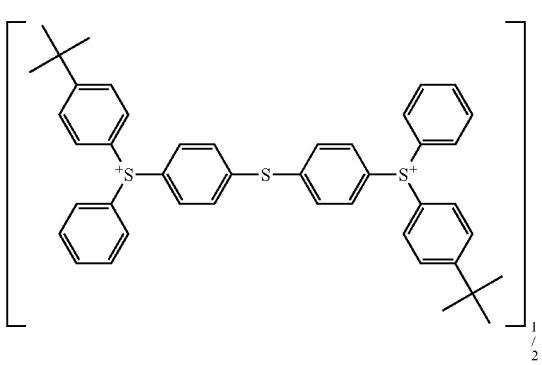
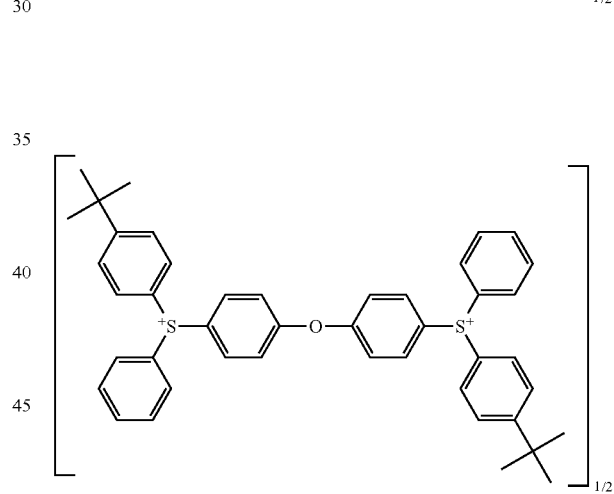
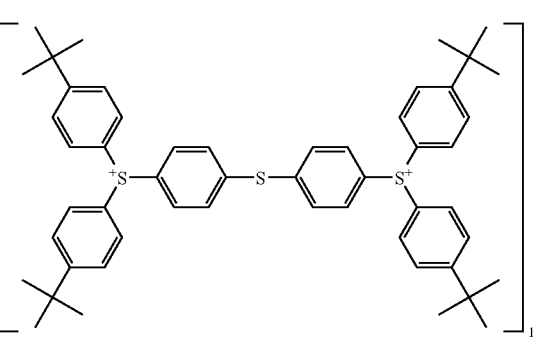
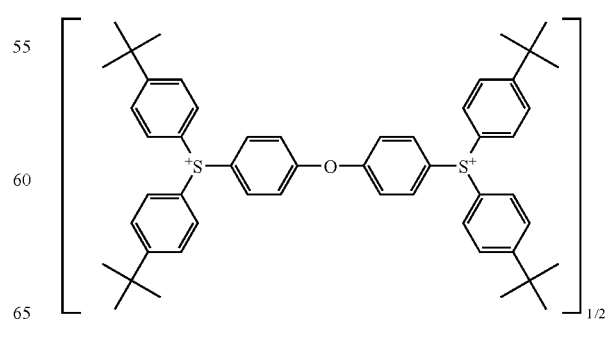
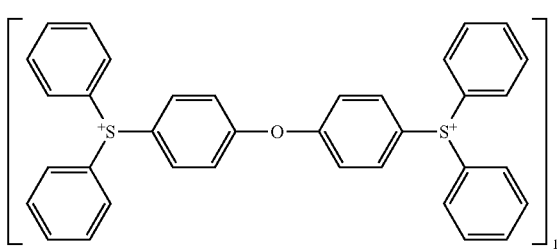

Among the cation (IXz), the cation represented by the formula (IXa):

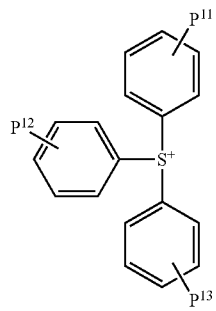

(IXa)

wherein $P^{11}$, $P^{12}$ and $P^{13}$ each independently represent a hydrogen atom, a hydroxyl group, a C1-C12 linear or branched chain alkyl group or a C1-C12 linear or branched chain alkoxy group, is preferable. Examples of the C1-C12 linear or branched chain alkyl group and the C1-C12 linear or branched chain alkoxy group include the same as described above.

As the organic counter ion represented by $A^+$, a cation represented by the following formulae (IXe):

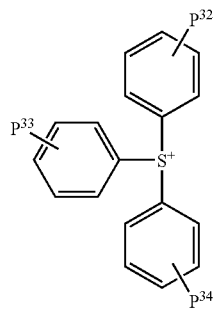

(IXe)

wherein $P^{32}$, $P^{33}$ and $P^{34}$ each independently represent a hydrogen atom or a C1-C4 alkyl group, is also preferable.

As the Salt (VI), a salt wherein $A^+$ is the cation represented by the following formulae (IXe) and the anion part is the following:

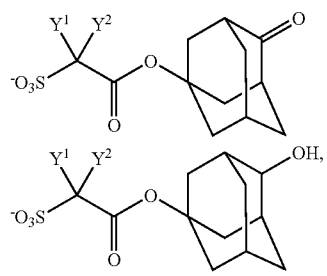

and
a salt wherein $A^+$ is the cation represented by the following formulae (IXc) and the anion part is the following:

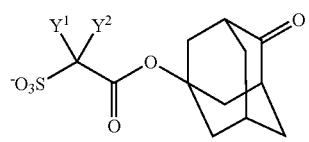

are preferable.

Salt (VI) can be produced according to known methods such as a method described in JP 2007-249192 A1.

The present resist composition preferably contains the compound (I) in an amount of about 80 to 99.9% by weight and the acid generator in an amount of 0.1 to 20% by weight on the total amount of the compound (I) and the acid generator.

The present resist composition may contain the compound (III).

In the present resist composition, performance deterioration caused by inactivation of acid which occurs due to post exposure delay can be diminished by adding an organic base compound, particularly a nitrogen-containing organic base compound as a quencher. The present resist composition may contain two or more kinds of organic base compounds.

Specific examples of the nitrogen-containing organic base compound include an amine compound represented by the following formulae:

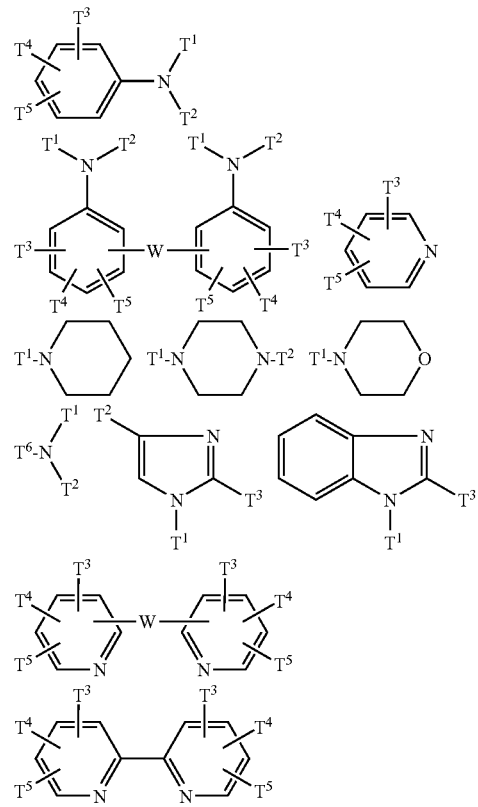

wherein $T^1$ and $T^2$ each independently represent a hydrogen atom, an alkyl group, a cycloalkyl group or an aryl group, and the alkyl, cycloalkyl and aryl groups may have one or more substituents selected from the group consisting of a hydroxyl group, an amino group which have one or two C1-C4 alkyl groups and a C1-C6 alkoxy group, $T^3$ and $T^4$ each independently represent a hydrogen atom, an alkyl group, a cycloalkyl group, an aryl group or an alkoxy group, and the alkyl, cycloalkyl, aryl and alkoxy groups may have one or more substituents selected from the group consisting of a hydroxyl group, an amino group which may have one or more C1-C4 alkyl groups and a C1-C6 alkoxy group, or $T^3$ and $T^4$ are bonded each other to form an aromatic ring together with the carbon atoms to which they are bonded, $T^5$ represents a hydrogen atom, an alkyl group, a cycloalkyl group, an aryl group, an alkoxy group or a nitro group, and the alkyl, cycloalkyl, aryl and alkoxy groups may have one or more substituents selected from the group consisting of a hydroxyl group, an amino group which may have one or two C1-C4 alkyl groups and a C1-C6 alkoxy group, $T^6$ represents an alkyl group or a cycloalkyl group, and the alkyl and cycloalkyl groups may have one or more substituents selected from the group consisting of a hydroxyl group, an amino group which may have one or two C1-C4 alkyl groups and a C1-C6 alkoxy group, and W represents —CO—, —NH—, —S—, —S—S—, an alkylene group of which one or more —CH$_2$— may be replaced by —O—, or an alkenylene group of which one or more —CH$_2$— may be replaced by —O—, and a quaternary ammonium hydroxide represented by the following formula:

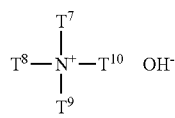

wherein $T^7$, $T^8$, $T^9$ and $T^{10}$ each independently represent an alkyl group, a cycloalkyl group or an aryl group, and the alkyl, cycloalkyl and aryl groups may have one or more substituents selected from the group consisting of a hydroxyl group, an amino group which may have one or two C1-C4 alkyl groups and a C1-C6 alkoxy group.

The alkyl group in $T^1$, $T^2$, $T^3$, $T^4$, $T^5$, $T^6$, $T^7$, $T^8$, $T^9$ and $T^{10}$ preferably has about 1 to 10 carbon atoms, and more preferably has about 1 to 6 carbon atoms.

Examples of the amino group which may have one or two C1-C4 alkyl groups include an amino group, a methylamino group, an ethylamino group, a butylamino group, a dimethylamino group and a diethylamino group. Examples of the C1-C6 alkoxy group which may be substituted with the C1-C6 alkoxy group or groups include a methoxy group, an ethoxy group, a propoxy group, an isopropoxy group, a butoxy group, a tert-butoxy group, a pentyloxy group, a hexyloxy group and a 2-methoxyethoxy group.

Specific examples of the alkyl group which may have one or more substituents selected from the group consisting of a hydroxyl group, an amino group which may have one or two C1-C4 alkyl groups, and a C1-C6 alkoxy group include a methyl group, an ethyl group, a propyl group, an isopropyl group, a butyl group, a tert-butyl group, a pentyl group, a hexyl group, an octyl group, a nonyl group, a decyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

The cycloalkyl group in $T^1$, $T^2$, $T^3$, $T^4$, $T^5$, $T^6$, $T^7$, $T^8$, $T^9$ and $T^{10}$ preferably has about 5 to 10 carbon atoms. Specific examples of the cycloalkyl group which may have one or more substituents selected from the group consisting of a hydroxyl group, an amino group which may have one or two C1-C4 alkyl groups and a C1-C6 alkoxy group include a cyclopentyl group, a cyclohexyl group, a cycloheptyl group and a cyclooctyl group.

The aryl group in $T^1$, $T^2$, $T^3$, $T^4$, $T^5$, $T^6$, $T^7$, $T^8$, $T^9$ and $T^{10}$ preferably has about 6 to 10 carbon atoms. Specific examples of the aryl group which may have one or more substituents selected from the group consisting of a hydroxyl group, an amino group which may have one or two C1-C4 alkyl groups and a C1-C6 alkoxy group include a phenyl group and a naphthyl group.

The alkoxy group in $T^3$, $T^4$ and $T^5$ preferably has about 1 to 6 carbon atoms and specific examples thereof include a methoxy group, an ethoxy group, a propoxy group, an isopropoxy group, a butoxy group, a tert-butoxy group, a pentyloxy group and a hexyloxy group.

The alkylene and alkenylene groups in W preferably have 2 to 6 carbon atoms. Specific examples of the alkylene group include an ethylene group, a trimethylene group, a tetramethylene group, a methylenedioxy group and an ethylene-1,2-dioxy group, and specific examples of the alkenylene group include an ethene-1,2-diyl group, a 1-propene-1,3-diyl group and a 2-butene-1,4-diyl group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

The amount of the quencher is usually 0.001 to 10 parts by weight, preferably 0.01 to 5 parts by weight relative to 100 parts by weight of the compound (I).

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted.

The analytical condition of liquid chromatography analysis was as followed:

Apparatus: LC-10 A manufactured by SHIMADZU CORPORATION
Column: L column ODS 4.6 mm φ×150 mm
Column temperature: 40° C.
Mobile phase: Liquid A: 5% aqueous acetonitrile solution
    Liquid B: acetonitrile
Gradient: 0 min.: Liquid A/Liquid B=70/30
    40 min.: Liquid A/Liquid B=0/100
    80 min.: Liquid A/Liquid B=0/100 (End of analysis)
Flow rate: 1.0 mL/min.
Injection volume: 10 μL
Detector: UV 235 nm The analytical condition of FD mass spectroscopy analysis was as followed:
Apparatus: JMS-SX102 manufactured by JEOL Ltd.
Accelerating voltage: 8 kV The analytical condition of the above-mentioned liquid chromatography mass spectroscopy analysis was as followed:
LC apparatus: Agilent 1100 manufactured by Agilent Technologies, Inc.
Column: L column ODS 2.1 mm φ×150 mm
Mobile phase: Liquid A: water
    Liquid B: acetonitrile
Gradient: 0 min.: Liquid A/Liquid B=90/10
    10 min.: Liquid A/Liquid B=90/10
    40 min.: Liquid A/Liquid B=0/100
    70 min.: Liquid A/Liquid B=0/100 (End of analysis)
Flow rate: 0.3 mL/min.
Injection volume: 2.5 μL
Detector: UV 210 nm, 254 nm, 220 nm
MS apparatus: HP LC-MSD Example 1

Ten grams of a compound represented by the formula (III-1):

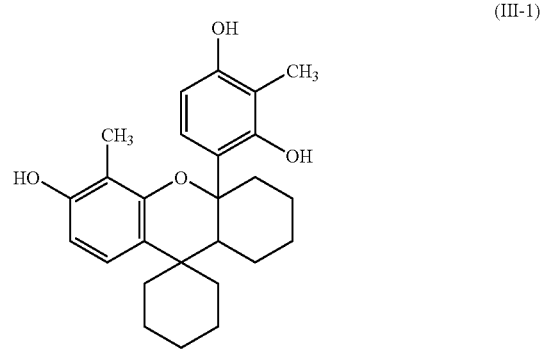

(hereinafter, simply referred to as B1) was dissolved in 90 g of N,N-dimethylformamide. To the resultant solution, 5.1 g of potassium carbonate was added. Into the obtained mixture, a solution obtained by mixing 6 g of 2-methyl-2-adamantyl chloroacetate with 30 g of N,N-dimethylformamide was charged at room temperature. To the obtained mixture, 0.4 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 11.55 g of a solid, which is called as A1.

A1 was analyzed by liquid chromatography to find out that B1, a compound represented by the formula (1):

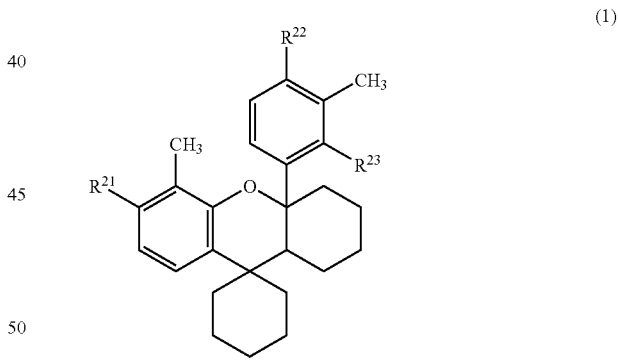

wherein any one of $R^{21}$, $R^{22}$ and $R^{23}$ is the group represented by the following formula (R-2):

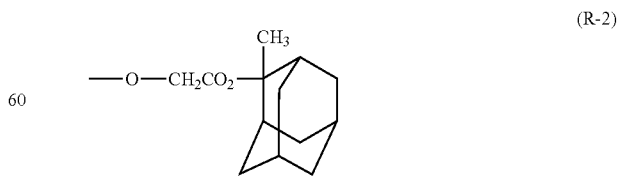

and the other two groups are hydroxyl groups (hereinafter, simply referred to as COMPOUND (1)), and a compound represented by the formula (2):

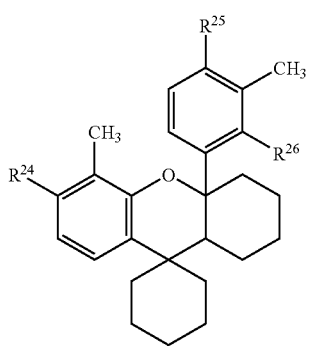

(2)

wherein any two of $R^{24}$, $R^{25}$ and $R^{26}$ are the groups represented by the above-mentioned formula (R-2) and the other one group is a hydroxyl group (hereinafter, simply referred to as COMPOUND (2)) were contained in A1.

The content ratio of COMPOUND (1), COMPOUND (2) and B1 in A1 (COMPOUND (1): COMPOUND (2): B1) was 40:13:47. Hereinafter, "the content ratio" means a ratio of values of each compounds calculated by a liquid chromatography area percentage method.

FD mass spectroscopy;
COMPOUND (1): $M^+=614$ ($M^+=614.81$)

Liquid chromatography mass spectroscopy;
COMPOUND (1): $[M+K]^+=653.2$ ($M^+=614.81$)
COMPOUND (2): $[M+K]^+=859.4$ ($M^+=821.09$)

Example 2

Ten grams of B1 was dissolved in 90 g of N,N-dimethylformamide. To the resultant solution, 10.2 g of potassium carbonate was added. Into the obtained mixture, a solution obtained by mixing 11.9 g of 2-methyl-2-adamantyl chloroacetate with 60 g of N,N-dimethylformamide was charged at room temperature. To the obtained mixture, 0.8 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 9.59 g of a solid, which is called as A2.

A2 was analyzed by liquid chromatography to find out that B1, COMPOUND (1), COMPOUND (2) and a compound represented by the formula (3):

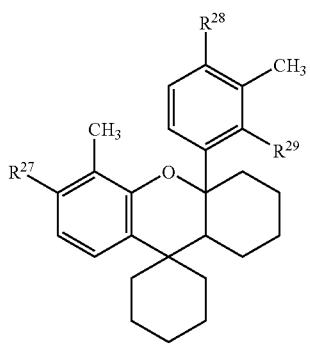

(3)

wherein $R^{27}$, $R^{28}$ and $R^{29}$ are the groups represented by the above-mentioned formula (R-2) (hereinafter, simply referred to as COMPOUND (3)) were contained in A2.

The content ratio of COMPOUND (1), COMPOUND (2), COMPOUND (3) and B1 in A2 (COMPOUND (1): COMPOUND (2): COMPOUND (3): B1) was 34:32:6:28.

Liquid chromatography mass spectroscopy;
COMPOUND (1): $[M+K]^+=653.2$ ($M^+=614.81$)
COMPOUND (2): $[M+K]^+=859.4$ ($M^+=821.09$)
COMPOUND (3): $[M+K]^+=1066.6$ ($M^+=1027.3$)

Example 3

Ten grams of a compound represented by the formula (III-3):

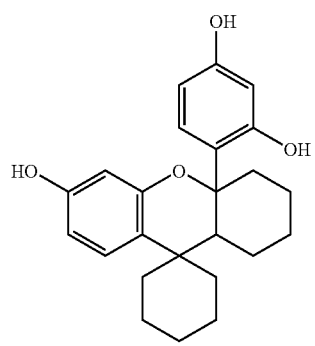

(III-3)

(hereinafter, simply referred to as B2) was dissolved in 100 g of N,N-dimethylformamide. To the resultant solution, 5.5 g of potassium carbonate was added. Into the obtained mixture, a solution obtained by mixing 6.4 g of 2-methyl-2-adamantyl chloroacetate with 40 g of N,N-dimethylformamide was charged at room temperature. To the obtained mixture, 0.5 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 11.20 g of a solid, which is called as A3.

A3 was analyzed by liquid chromatography to find out that B2, a compound represented by the formula (4):

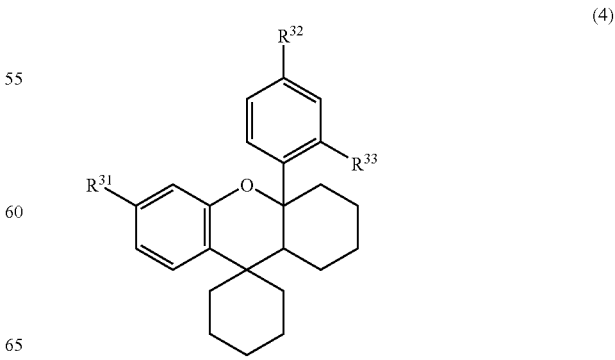

(4)

wherein any one of $R^{31}$, $R^{32}$ and $R^{33}$ is the group represented by the above-mentioned formula (R-2) and the other two groups are hydroxyl groups (hereinafter, simply referred to as COMPOUND (4)), a compound represented by the formula (5):

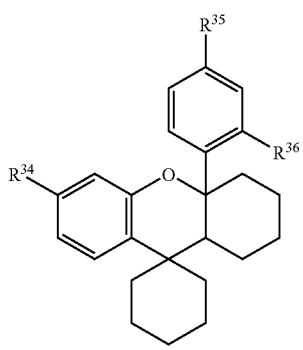

(5)

wherein any two of $R^{34}$, $R^{35}$ and $R^{36}$ are the groups represented by the above-mentioned formula (R-2) and the other one group is a hydroxyl group (hereinafter, simply referred to as COMPOUND (5)), and a compound represented by the formula (6):

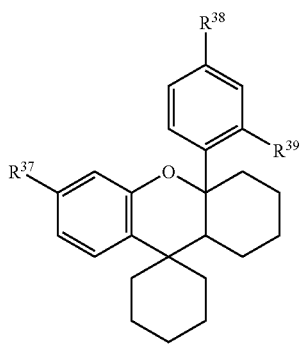

(6)

wherein $R^{37}$, $R^{38}$ and $R^{39}$ are the groups represented by the above-mentioned formula (R-2) (hereinafter, simply referred to as COMPOUND (6)) were contained in A3.

The content ratio of COMPOUND (4), COMPOUND (5), COMPOUND (6) and B2 in A3 (COMPOUND (4): COMPOUND (5): COMPOUND (6): B2) was 37:17:9:37.
FD mass spectroscopy;
  COMPOUND (4): $M^+=586$ ($M^+=586.76$)
Liquid chromatography mass spectroscopy;
  COMPOUND (4): $[M+K]^+=625.2$ ($M^+=586.76$)
  COMPOUND (5): $[M+K]^+=831.4$ ($M^+=793.04$)
  COMPOUND (6): $[M+K]^+=1037.4$ ($M^+=999.32$)

Example 4

Ten grams of B2 was dissolved in 100 g of N,N-dimethylformamide. To the resultant solution, 10.9 g of potassium carbonate was added. Into the obtained mixture, a solution obtained by mixing 12.8 g of 2-methyl-2-adamantyl chloroacetate with 80 g of N,N-dimethylformamide was charged at room temperature. To the obtained mixture, 1.0 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 11.20 g of a solid, which is called as A4.

A4 was analyzed by liquid chromatography to find out that B2, COMPOUND (4), COMPOUND (5) and COMPOUND (6) were contained in A4.

The content ratio of COMPOUND (4), COMPOUND (5), COMPOUND (6) and B2 in A4 (COMPOUND (4): COMPOUND (5): COMPOUND (6): B2) was 22:33:31:14.

Example 5

Ten grams of a compound represented by the formula (III-5):

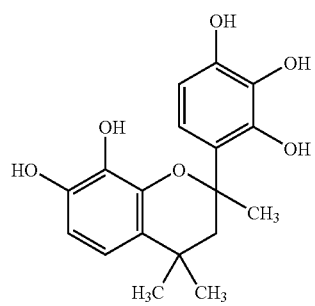

(III-5)

(hereinafter, simply referred to as B3) was dissolved in 90 g of N,N-dimethylformamide. To the resultant solution, 6.3 g of potassium carbonate was added. Into the obtained mixture, a solution obtained by mixing 7.3 g of 2-methyl-2-adamantyl chloroacetate with 35 g of N,N-dimethylformamide was charged at room temperature. To the obtained mixture, 0.5 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 12.76 g of a solid, which is called as A5.

A5 was analyzed by liquid chromatography to find out that a compound represented by the formula (7):

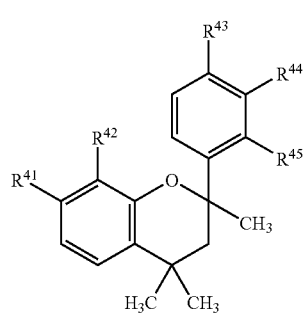

(7)

wherein any one of $R^{41}$, $R^{42}$, $R^{43}$, $R^{44}$ and $R^{45}$ is the group represented by the above-mentioned formula (R-2) and the other four groups are hydroxyl groups (hereinafter, simply referred to as COMPOUND (7)), a compound represented by the formula (8):

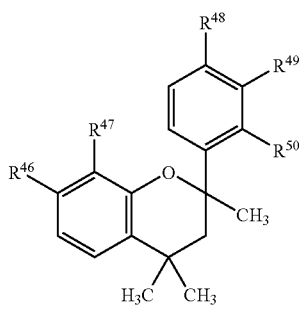

wherein any two of $R^{46}$, $R^{47}$, $R^{48}$, $R^{49}$ and $R^{50}$ are the groups represented by the above-mentioned formula (R-2) and the other three groups are hydroxyl groups (hereinafter, simply referred to as COMPOUND (8)), and a compound represented by the formula (9):

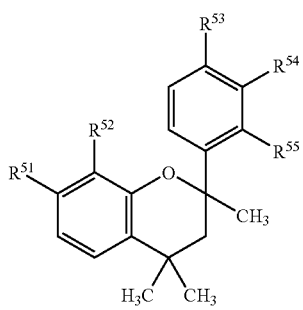

wherein any three of $R^{51}$, $R^{52}$, $R^{53}$, $R^{54}$ and $R^{55}$ are the groups represented by the above-mentioned formula (R-2) and the other two groups are hydroxyl groups (hereinafter, simply referred to as COMPOUND (9)) were contained in A5.

The content ratio of COMPOUND (7), COMPOUND (8) and COMPOUND (9) in A5 (COMPOUND (7): COMPOUND (8): COMPOUND (9)) was 75:23:2.

FD mass spectroscopy;
  COMPOUND (7): $M^+=538$ ($M^+=538.63$)
Liquid chromatography mass spectroscopy;
  COMPOUND (7): $[M+K]^+=577.2$ ($M^+=538.63$)
  COMPOUND (8): $[M+K]^+=783.2$ ($M^+=744.91$)
  COMPOUND (9): $[M+K]^+=989.4$ ($M^+=951.19$)

Example 6

Ten grams of B3 was dissolved in 90 g of N,N-dimethylformamide. To the resultant solution, 12.5 g of potassium carbonate was added. Into the obtained mixture, a solution obtained by mixing 14.6 g of 2-methyl-2-adamantyl chloroacetate with 70 g of N,N-dimethylformamide was charged at room temperature. To the obtained mixture, 1.0 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 12.98 g of a solid, which is called as A6.

A6 was analyzed by liquid chromatography to find out that COMPOUND (7), COMPOUND (8) and COMPOUND (9) were contained in A6.

The content ratio of COMPOUND (7), COMPOUND (8) and COMPOUND (9) in A6 (COMPOUND (7): COMPOUND (8): COMPOUND (9)) was 16:59:25.

Example 7

Ten grams of a compound represented by the formula (III-7):

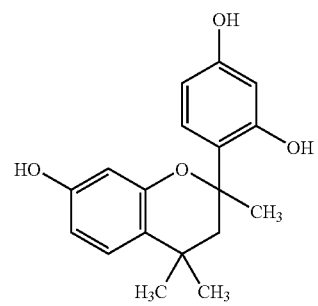

(hereinafter, simply referred to as B4) was dissolved in 100 g of N,N-dimethylformamide. To the resultant solution, 6.9 g of potassium carbonate was added. Into the obtained mixture, a solution obtained by mixing 8.1 g of 2-methyl-2-adamantyl chloroacetate with 40 g of N,N-dimethylformamide was charged at room temperature. To the obtained mixture, 0.6 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 9.45 g of a solid, which is called as A7.

A7 was analyzed by liquid chromatography to find out that B4, a compound represented by the formula (10):

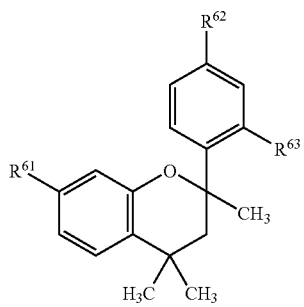

wherein any one of $R^{61}$, $R^{62}$ and $R^{63}$ is the group represented by the above-mentioned formula (R-2) and the other two groups are hydroxyl groups (hereinafter, simply referred to as COMPOUND (10)), a compound represented by the formula (11):

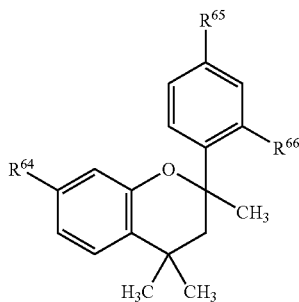

wherein any two of $R^{64}$, $R^{65}$ and $R^{66}$ are the groups represented by the above-mentioned formula (R-2) and the other one group is a hydroxyl group (hereinafter, simply referred to as COMPOUND (11)), and a compound represented by the formula (12):

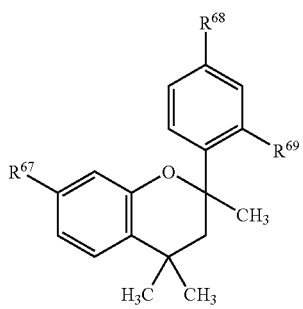

wherein any three of $R^{67}$, $R^{68}$ and $R^{69}$ are the groups represented by the above-mentioned formula (R-2) (hereinafter, simply referred to as COMPOUND (12)) were contained in A7.

The content ratio of COMPOUND (10), COMPOUND (11), COMPOUND (12) and B4 in A7 (COMPOUND (10): COMPOUND (11): COMPOUND (12): B4) was 36:26:9:29.
FD mass spectroscopy;
  COMPOUND (10): $M^+$=506 ($M^+$=506.63)
Liquid chromatography mass spectroscopy;
  COMPOUND (10): $[M+K]^+$=545.2 ($M^+$=506.63)
  COMPOUND (11): $[M+K]^+$=809.2 ($M^+$=770.95)
  COMPOUND (12): $[M+K]^+$=957.4 ($M^+$=919.19)

Example 8

Ten grams of B4 was dissolved in 100 g of N,N-dimethylformamide. To the resultant solution, 13.8 g of potassium carbonate was added. Into the obtained mixture, a solution obtained by mixing 16.2 g of 2-methyl-2-adamantyl chloroacetate with 80 g of N,N-dimethylformamide was charged at room temperature. To the obtained mixture, 1.1 g of potassium iodide was added and the resultant mixture was stirred at 50° C. for 5 hours. The reaction mixture was cooled, diluted with 1% aqueous oxalic acid solution to be acidified followed by conducting extraction with ethyl acetate. The organic layer was washed with pure water to adjust pH thereof to 5. The organic layer was mixed with activated carbon to be decolorized. The obtained mixture was filtrated and the filtrate was concentrated to obtain 14.16 g of a solid, which is called as A8.

A8 was analyzed by liquid chromatography to find out that B4, COMPOUND (10), COMPOUND (11) and COMPOUND (12) were contained in A8.

The content ratio of COMPOUND (10), COMPOUND (11), COMPOUND (12) and B4 in A8 (COMPOUND (10): COMPOUND (11): COMPOUND (12): B4) was 23:38:28:11.

Example 9

Fifteen grams of B1 was dissolved in 150 g of N,N-dimethylformamide. To the resultant solution, 15.3 g of potassium carbonate was added. Into the obtained mixture, a solution obtained by mixing 18.9 g of 2-ethyl-2-adamantyl chloroacetate with 50 g of N,N-dimethylformamide was charged at room temperature. To the obtained mixture, 1.2 g of potassium iodide was added and the resultant mixture was stirred at 70 to 75° C. for 5 hours. The reaction mixture was cooled, diluted with 3% aqueous oxalic acid solution to be acidified followed by conducting extraction with ethyl acetate. The organic layer was washed with pure water to adjust pH thereof to 7. The organic layer was mixed with activated carbon to be decolorized. The obtained mixture was filtrated and the filtrate was concentrated to obtain 32.00 g of a solid, which is called as A9.

A9 was analyzed by liquid chromatography to find out that B1, a compound represented by the formula (13):

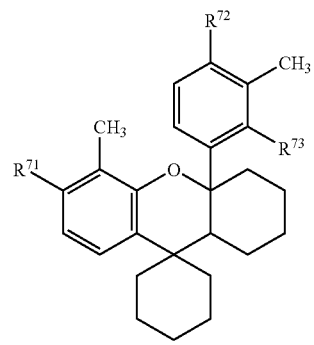

wherein any one of $R^{71}$, $R^{72}$ and $R^{73}$ is the group represented by the following formula (R-3):

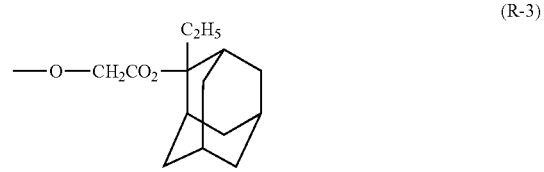

and the other two groups are hydroxyl groups (hereinafter, simply referred to as COMPOUND (13)), a compound represented by the formula (14):

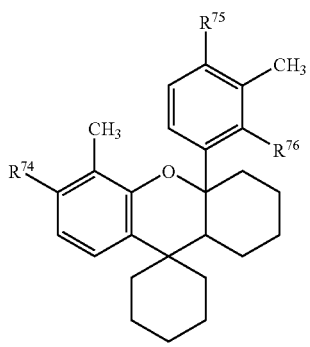

(14)

wherein any two of $R^{74}$, $R^{75}$ and $R^{76}$ are the groups represented by the above-mentioned formula (R-3) and the other one group is a hydroxyl group (hereinafter, simply referred to as COMPOUND (14)) and a compound represented by the formula (15):

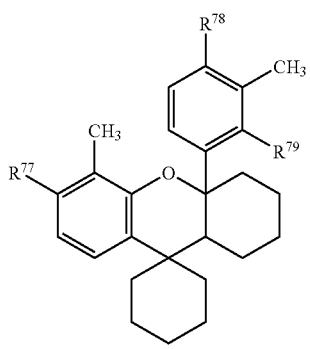

(15)

wherein $R^{77}$, $R^{78}$ and $R^{79}$ are the groups represented by the above-mentioned formula (R-3) were contained in A9.

The content ratio of COMPOUND (13), COMPOUND (14), COMPOUND (15) and B1 in A9 (COMPOUND (13): COMPOUND (14): COMPOUND (15): B1) was 19:26:42:13.

Liquid chromatography mass spectroscopy;
COMPOUND (13): $[M+Na]^+$=651.4 ($M^+$=628.84)
COMPOUND (14): $[M+Na]^+$=871.5 ($M^+$=849.14)
COMPOUND (15): $[M+Na]^+$=1091.7 ($M^+$=1069.45)

The liquid chromatography mass spectroscopy analysis in Example 9 was conducted under the following conditions.
LC apparatus: Agilent 1100 manufactured by Agilent Technologies, Inc.
Column: L column ODS 2.1 mm φ×150 mm
Mobile phase: Liquid A: water
Liquid B: acetonitrile
Liquid C: tetrahydrofuran
Gradient: 0 min.: Liquid A/Liquid B/Liquid C=80/10/10
25 min.: Liquid A/Liquid B/Liquid C=30/60/10
45 min.: Liquid A/Liquid B/Liquid C=0/30/70
50 min.: Liquid A/Liquid B/Liquid C=0/30/70 (End of analysis)
Flow rate: 0.4 mL/min.
Injection volume: 2.5 μL
Detector: UV 210 nm, 254 nm, 280 nm
MS apparatus: HP LC-MSD Twenty point five grams of A9 was purified by silica gel chromatography using 200 g of silica gel and a mixed solvent of hexane and ethyl acetate as an eluent. The obtained solutions were concentrated respectively to obtain 3.4 g of COMPOUND (13) (purity: 77%), 6.2 g of COMPOUND (14) (purity: 98%), 7.7 g of COMPOUND (15) (purity: 95%) and 1.1 g of B1. Herein, "purity" means an area percentage value of each of the compounds calculated by a liquid chromatography area percentage method.

The compound (I), Acid generators, quenchers and solvents used in the following Examples are followings.
<The Compound (I)>
A1
A6
<Acid Generator>
Acid generator P1: triphenylsulfonium 4-oxo-1-adamantyloxycarbonyldifluoromethanesulfonate
<Quencher>
Quencher Q1: 2,6-diisopropylaniline
<Solvent>

| Solvent S1: | propylene glycol monomethyl ether | 170 parts |
|---|---|---|
| | 2-heptanone | 30 parts |
| | propylene glycol monomethyl ether acetate | 40 parts |
| | γ-butyrolactone | 5 parts |

Examples 10 and 11

The following components were mixed to give a solution, and the solution was further filtrated through a fluorine resin filter having a pore diameter of 0.2 μm, to prepare a resist composition.
The compound (I) (kind and amount are described in Table 1)
Acid generator (kind and amount are described in Table 1)
Quencher (kind and amount are described in Table 1)
Solvent (kind are described in Table 1)

TABLE 1

| Ex. No. | The compound (I) (kind/amount (part)) | Acid generator (kind/amount (part)) | Quencher (kind/amount (part)) | Solvent |
|---|---|---|---|---|
| Ex. 10 | A1/10 | P1/0.8 | Q1/0.03 | S1 |
| Ex. 11 | A6/10 | P1/0.8 | Q1/0.03 | S1 |

Silicon wafers were each contacted with hexamethyldisilazane at 90° C. for 60 seconds and each of the resist compositions prepared as above was spin-coated over the silicon wafer to give a film thickness after drying of 0.06 μm. After application of each of the resist compositions, the silicon wafers thus coated with the respective resist compositions were each prebaked on a direct hotplate at 110° C. for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at 100° C. for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 2.

Effective Sensitivity (ES): It is expressed as the amount of exposure that the line pattern and the space pattern become 1:1 after exposure through 0.10 μm line and space pattern mask and development.

Resolution: It is expressed as the minimum size of space pattern which gave the space pattern split by the line pattern at the exposure amount of the effective sensitivity. The smaller the value is, the higher the Resolution is.

Line Width Roughness: Each of a wall surface of 0.10 μm line and space pattern obtained at the exposure amount of the effective sensitivity was observed with a scanning electron microscope. When the wall surface is smooth, line width roughness is very good and its evaluation is marked by "○", and when the wall surface is not smooth, line width roughness is bad and its evaluation is marked by "X".

TABLE 2

| Ex. No. | ES (μC) | Resolution (nm) | Line Width Roughness |
|---|---|---|---|
| Ex. 10 | 50 | 80 | ○ |
| Ex. 11 | 35 | 80 | ○ |

Apparent from the results shown in Table 2, the resist compositions obtained by Examples corresponding to the present invention show good resolution and line width roughness.

Example 12

A resist pattern can be obtained according to the same manner as described in Example 10, except that a resist composition containing A2 are used in place of the resist composition containing A1.

Example 12

A resist pattern can be obtained according to the same manner as described in Example 10, except that a resist composition containing A2 are used in place of the resist composition containing A1.

Example 13

A resist pattern can be obtained according to the same manner as described in Example 10, except that a resist composition containing A3 are used in place of the resist composition containing A1.

Example 14

A resist pattern can be obtained according to the same manner as described in Example 10, except that a resist composition containing A4 are used in place of the resist composition containing A1.

Example 15

A resist pattern can be obtained according to the same manner as described in Example 10, except that a resist composition containing A5 are used in place of the resist composition containing A1.

Example 16

A resist pattern can be obtained according to the same manner as described in Example 10, except that a resist composition containing A7 are used in place of the resist composition containing A1.

Example 17

A resist pattern can be obtained according to the same manner as described in Example 10, except that a resist composition containing A8 are used in place of the resist composition containing A1.

Example 18

A resist pattern can be obtained according to the same manner as described in Example 10, except that a resist composition containing A9 are used in place of the resist composition containing A1.

The present resist composition provides excellent resist pattern in resolution and line width roughness and is suitable for extreme ultraviolet (EUV) lithography and electron lithography.

What is claimed is:

1. A compound represented by the formula (I):

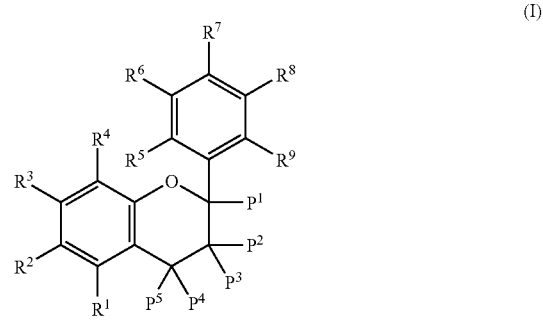

(I)

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and least one selected from the group consisting of $R^1$, $R^2$, $R^3$, $R^4$, $R^5$, $R^6$, $R^7$, $R^8$ and $R^9$ is the group represented by the formula (II):

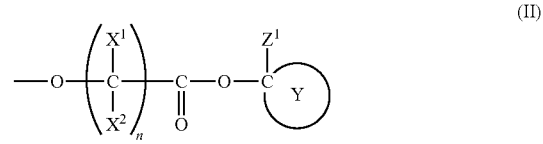

(II)

wherein $X^1$ and $X^2$ each independently represent a hydrogen atom or a C1-C4 alkyl group, n represents an integer of 1 to 4, $Z^1$ represents a C1-C6 alkyl group or a C3-C12 cycloalkyl group, and ring Y represents an alicyclic hydrocarbon group, and the others each independently represent a hydrogen atom, a C1-C6 alkyl group or a hydroxyl group.

2. The compound according to claim 1, wherein $X^1$ and $X^2$ are hydrogen atoms and n is 1.

3. The compound according to claim 1, wherein the molecular weight of the compound represented by the formula (I) is 500 to 5,000.

4. A chemically amplified resist composition comprising a compound represented by the formula (I):

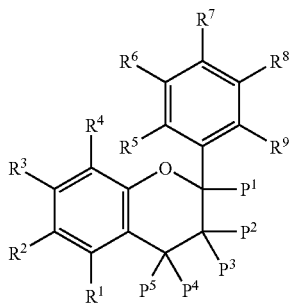

(I)

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and $R^1$, $R^2$, $R^3$, $R^4$, $R^5$, $R^6$, $R^7$, $R^8$ and $R^9$ each independently represent a hydrogen atom, a C1-C6 alkyl group, a hydroxyl group or a group represented by the formula (II):

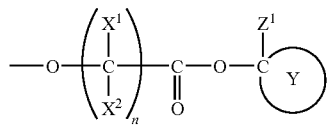

(II)

wherein $X^1$ and $X^2$ each independently represent a hydrogen atom or a C1-C4 alkyl group, n represents an integer of 1 to 4, $Z^1$ represents a C1-C6 alkyl group or a C3-C12 cycloalkyl group, and ring Y represents an alicyclic hydrocarbon group, and at least one selected from the group consisting of $R^1$, $R^2$, $R^3$, $R^4$, $R^5$, $R^6$, $R^7$, $R^8$ and $R^9$ is the group represented by the formula (II), and an acid generator.

5. The chemically amplified resist composition according to claim 4, wherein the composition contains at least two kinds of the compound represented by the formula (I).

6. The chemically amplified resist composition according to claim 4, wherein the composition further contains at least one compound selected from a compound represented by the formula (III):

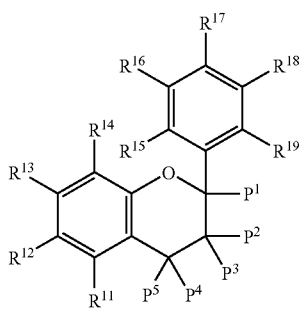

(III)

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and $R^{11}$, $R^{12}$, $R^{13}$, $R^{14}$, $R^{15}$, $R^{16}$, $R^{17}$, $R^{18}$ and $R^{19}$ each independently represent a hydrogen atom, a C1-C6 alkyl group or a hydroxyl group, and at least one selected from the group consisting of $R^{11}$, $R^{12}$, $R^{13}$, $R^{14}$, $R^{15}$, $R^{16}$, $R^{17}$, $R^{18}$ and $R^{19}$ is a hydroxyl group.

7. The chemically amplified resist composition according to claim 4, wherein the acid generator is a salt represented by the formula (V):

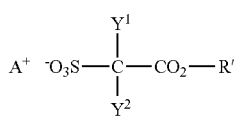

(V)

wherein $A^+$ represents an organic counter ion, $Y^1$ and $Y^2$ each independently represent a fluorine atom or a C1-C6 perfluoroalkyl group, R' represents a C1-C30 hydrocarbon group which may have one or more substituents selected from the group consisting of a C1-C6 alkoxy group, a C1-C4 perfluoroalkyl group, a C1-C6 hydroxyalkyl group, a hydroxyl group and a cyano group, and in which one or more —$CH_2$— may be replaced by —CO— or —O—.

8. A process for production of a compound represented by the formula (I):

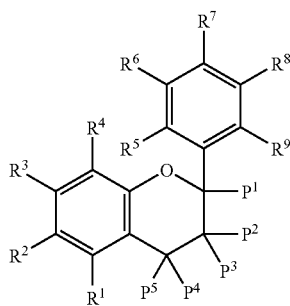

(I)

wherein $P^1$, $P^2$, $P^3$, $P^4$ and $P^5$ each independently represents a hydrogen atom, a C1-C4 alkyl group, a C2-C4 alkenyl group, a C2-C4 alkynyl group, a C3-C8 cycloalkyl group, a C6-C12 aryl group or a C7-C12 aralkyl group, and $P^1$ and $P^2$ may be bonded each other to form a C3-C12 divalent acyclic hydrocarbon group which forms a ring together with the carbon atoms to which they are bonded, and $P^4$ and $P^5$ may be bonded each other to form a C3-C12 divalent acyclic hydrocarbon group which forms a ring together with the carbon atom to which they are bonded, and $R^1$, $R^2$, $R^3$, $R^4$, $R^5$, $R^6$, $R^7$, $R^8$ and $R^9$ each independently represent a hydrogen atom, a C1-C6 alkyl group, a hydroxyl group or a group represented by the formula (II):

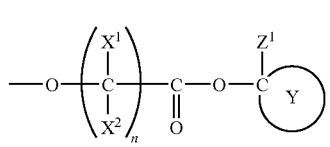

(II)

wherein $X^1$ and $X^2$ each independently represent a hydrogen atom or a C1-C4 alkyl group, n represents an integer of 1 to 4, $Z^1$ represents a C1-C6 alkyl group or a C3-C12 cycloalkyl group, and ring Y represents an alicyclic hydrocarbon group, and at least one selected from the group consisting of $R^1$, $R^2$, $R^3$, $R^4$, $R^5$, $R^6$, $R^7$, $R^8$ and $R^9$ is the group represented by the formula (II), which comprises reacting a compound represented by the formula (III):

(III)

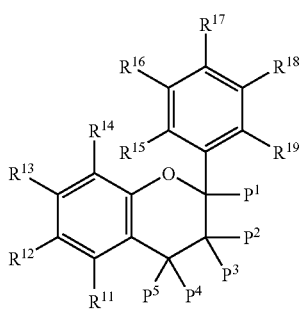

wherein $P^1$, $P^2$, $P^3$, $P^4$ and $P^5$ are the same as defined above, and at least one selected from the group consisting of $R^{11}$, $R^{12}$, $R^{13}$, $R^{14}$, $R^{15}$, $R^{16}$, $R^{17}$, $R^{18}$ and $R^{19}$ is a hydroxyl group and the others each independently represent a hydrogen atom, a C1-C6 alkyl group or a hydroxyl group, with a compound represented by the formula (IV):

(IV)

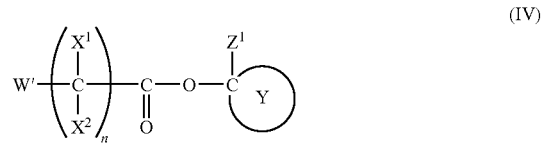

wherein $X^1$, $X^2$, n, $Z^1$ and Y are the same as defined above, and W' represents a chlorine atom, a bromine atom, an iodine atom, a methanesulfonyloxy group or a p-toluenesulfonyloxy group.

\* \* \* \* \*